US010233256B2

(12) United States Patent
Mazor et al.

(10) Patent No.: US 10,233,256 B2
(45) **Date of Patent: *Mar. 19, 2019**

(54) ANTIBODIES DIRECTED TO RICIN TOXIN

(71) Applicant: The Israel Institute of Biological Research (IIBR), Ness-Ziona (IL)

(72) Inventors: Ohad Mazor, Ness-Ziona (IL); Ronit Rosenfeld, Ness Ziona (IL); Arie Ordentlich, Ness-Ziona (IL); Tal Noy-Porat, Ness-Ziona (IL)

(73) Assignee: THE ISRAEL INSTITUTE OF BIOLOGICAL RESEARCH (IIBR), Ness-Ziona (IL)

( * ) Notice: Subject to any disclaimer, the term of this patent is extended or adjusted under 35 U.S.C. 154(b) by 58 days.

This patent is subject to a terminal disclaimer.

(21) Appl. No.: 14/952,283

(22) Filed: Nov. 25, 2015

(65) Prior Publication Data

US 2016/0152732 A1 Jun. 2, 2016

Related U.S. Application Data

(60) Provisional application No. 62/085,417, filed on Nov. 28, 2014.

(51) Int. Cl.

| | |
|---|---|
| ***A61K 39/00*** | (2006.01) |
| ***A61K 45/06*** | (2006.01) |
| ***C07K 16/40*** | (2006.01) |
| ***G01N 33/53*** | (2006.01) |
| ***G01N 33/68*** | (2006.01) |

(52) U.S. Cl.

CPC .............. *C07K 16/40* (2013.01); *A61K 45/06* (2013.01); *G01N 33/5308* (2013.01); *G01N 33/6854* (2013.01); *A61K 2039/505* (2013.01); *C07K 2317/24* (2013.01); *C07K 2317/76* (2013.01); *G01N 2333/924* (2013.01)

(58) Field of Classification Search

None

See application file for complete search history.

(56) References Cited

U.S. PATENT DOCUMENTS

| | | | | |
|---|---|---|---|---|
| 5,626,844 A | 5/1997 | Lemley et al. | | |
| 6,407,213 B1 * | 6/2002 | Carter | C07K 16/28 | 424/133.1 |
| 6,639,055 B1 * | 10/2003 | Carter | C07K 16/28 | 424/130.1 |
| 6,780,413 B2 * | 8/2004 | Hott | A61K 47/48446 | 424/143.1 |
| 7,175,845 B2 * | 2/2007 | Dertzbaugh | A61K 36/47 | 424/141.1 |
| 8,247,186 B2 * | 8/2012 | Grompe | C07K 16/28 | 424/152.1 |
| 8,344,109 B2 | 1/2013 | Thullier et al. | | |
| 8,535,668 B2 * | 9/2013 | Thullier | C07K 16/16 | 424/133.1 |
| 9,309,305 B2 * | 4/2016 | Hu | C07K 16/16 | |
| 2002/0081303 A1 * | 6/2002 | Hott | A61K 47/48446 | 424/178.1 |
| 2005/0266010 A1 * | 12/2005 | Hott | A61K 47/48446 | 424/178.1 |
| 2007/0009510 A1 * | 1/2007 | Dertzbaugh | A61K 36/47 | 424/133.1 |
| 2010/0240597 A1 * | 9/2010 | Cramer | A61K 36/47 | 514/21.2 |
| 2012/0121512 A1 * | 5/2012 | Grompe | G01N 33/56966 | 424/9.1 |
| 2012/0258100 A1 * | 10/2012 | Thullier | C07K 16/16 | 424/133.1 |
| 2014/0050722 A1 * | 2/2014 | Thullier | C07K 16/16 | 424/133.1 |
| 2014/0093504 A1 * | 4/2014 | Hu | C07K 16/16 | 424/133.1 |
| 2016/0152732 A1 * | 6/2016 | Mazor | C07K 16/40 | 424/146.1 |
| 2016/0207998 A1 * | 7/2016 | Hu | C07K 16/16 | |
| 2016/0280773 A1 * | 9/2016 | Hu | C07K 16/16 | |
| 2017/0174752 A1 * | 6/2017 | Mazor | C07K 16/16 | |

FOREIGN PATENT DOCUMENTS

| | | | |
|---|---|---|---|
| FR | 2922212 A1 * | 4/2009 | C07K 16/16 |
| FR | 2952059 A1 * | 5/2011 | C07K 16/16 |

(Continued)

OTHER PUBLICATIONS

Cohen et al, Clinical and Vaccine Immunology p. 1534-1540, Nov. 2014, vol. 21, No. 11.*

Gal et al, Toxicology Reports, 2014, 1:496-504.*

Gal et al, Journal of Immunological Methods 424 (2015) 136-139.*

Maddaloni et al, J Immunol 2004; 172:6221-6228.*

McGuinness et al, Infection and Immunity, Jun. 2006, 74/6:3463-3470.*

Noy-Porat et al, Toxins, Mar. 3, 2016, 8, 64, 15 pages.*

Noy-Porat et al, Toxicon 127 (2017) 100-105.*

(Continued)

*Primary Examiner* — Nita M. Minnifield

(74) *Attorney, Agent, or Firm* — Browdy and Neimark, PLLC

(57) ABSTRACT

An isolated monoclonal antibody or any antigen-binding fragment thereof which binds to ricin toxin, an expression vector including the isolated nucleic acid molecule and a host cell transfected with said isolated nucleic acid molecule or with the expression vector, a pharmaceutical composition including as an active ingredient the isolated monoclonal antibody or any antigen-binding fragment thereof, the bispecific molecule or the immunoconjugate and a pharmaceutically acceptable carrier, excipient or diluent, and a method of prophylaxis, treatment or amelioration of ricin toxin poisoning including administering to a subject in need thereof a therapeutically effective amount of the isolated monoclonal antibody or any antigen-binding fragment thereof, the bispecific molecule, the immunoconjugate or the pharmaceutical composition.

17 Claims, 7 Drawing Sheets

Specification includes a Sequence Listing.

(56) References Cited

FOREIGN PATENT DOCUMENTS

| | | | |
|---|---|---|---|
| WO | 03/072018 A2 | | 9/2003 |
| WO | 2012167346 A1 | | 12/2012 |
| WO | WO 2016/069627 A1 | * | 5/2016 |

OTHER PUBLICATIONS

Sabo et al, Toxicology Letters 237 (2015) 72-78.*
Sabo et al, "Ricin-Holotoxin-Based Vaccines: Induction of Potent Ricin-Neutralizing Antibodies" In: Sunil Thomas (ed.), Vaccine Design: Methods and Protocols: vol. 1: Vaccines for Human Diseases, Methods in Molecular Biology, vol. 1403:683-694.*
Yermakova et al, Vaccine 29, Aug. 26, 2011, pp. 7925-7935.*
Sandvig, K. and van Deurs, B. (1996) Physiol Rev 76:949-966.
Hu, W. G., et al. "Humanization and Characterization of an Anti-Ricin Neutralization Monoclonal Antibody" Plos One 7 (9): e45595 1-9 (2012).
Luker, G. D., et al. "Imaging 26S proteasome activity and inhibition in living mice" Nature Med 9:969-973 (2003).

* cited by examiner

Figure 1

```
                1                                                          60
MH74 VH         GAGGTGCAGCTGGTGCAATCTGGAGCAGAGGTGAAAAGGCCCGGGGAGTCACTGAAGATC
MH73 VH         CAGGTGCAGCTGCAGGAGTCGGGCCCAGGACTGGTGAAGCCTTCGGAGACCCTGTCCCTC
MH77 VH         CAGGTGCAGCTGCTCGAGTCGGGCCCAGGACTGGTGAAGCCTTCAGAGACCCTGTCCCTC
MH1  VH         CAGCTGCAGCTGCAGGAGTCGGGCCCAGGACTGGTGAAGCCTTCAGAGACCCTGTCCCTC
MH49 VH         GAGGCGCAGCTCGAGGAGTCGGGCCCAGGACTGGTGAAGCCTTCGGAGACCCTGTCCCTC
MH67 VH         CAGGTGCAGCTCGAGCAGTCGGGCCCAGGACTGGTGAAGCCTTCGGAGACCCTGTCCCTC
MH36 VH         GAAGTGCAGCTGGTGGAGTCTGGGGGAGGCTTGGTCCAGCCTGGGGGGTCCCTGAGGCTC
MH76 VH         CAGGTGCAGCTGCAGGAGTCTGGGGGCGGCTTGGCAAAGCCTGGGGGGTCCCTGAGACTC
MH2  VH         GAGGTTCAGTTGGTGGAATCTGGGGGCGGCTTGGCAAAGCCTGGGGGGTCCCTGAGACTC
MH75 VH         CAGGAGCAGCTGGTGCAGTCTGGGGGCGGCTTGGCAAAGCCTGGGGGGTCCCTGAGACTC
                61                                                        120
MH74 VH         TCCTGTAAGACTTCTGGATACAGCTTTA...CCAGCTACTGGATCAGCTGGGTGCGCCAG
MH73 VH         ACCTGCGCTGTCTCTGGTGGCTCCCTCA...GCAGTAACTACTGGAGCTGGATCCGCCAG
MH77 VH         ACCTGCACTGTCTCTGGTGGCTCTTTCAGTAGTAGTCATTGGTGGAACTGGATCCGCCAG
MH1  VH         ACTTGCGCTGTCTCTGGTGGCTCCATCAGCGGTGGTTATGGCTGGGGCTGGATCCGCCAG
MH49 VH         AGTTGCGCTGTCTCTGGTGGCTCCTTCA...GGAGTTACTGGTGGGGCTGGATCCGCCAG
MH67 VH         AGTTGCGCTGTCTCTGGTGGCTCCTTCA...GGAGTTACTGGTGGGGCTGGATCCGCCAG
MH36 VH         TCCTGTGCAGCCTCTGGATTCACCTTCA...GTAACGTCTGGATGAACTGGGTCCGCCAG
MH76 VH         TCCTGCGCAGCCTCCGGATTCACCTTCA...GTGACTACTACATGGACTGGGTCCGCCAG
MH2  VH         TCCTGCGCAGCCTCCGGATTCACCTTCA...GTGACTACTACATGGACTGGGTCCGCCAG
MH75 VH         TCCTGCGCAGACTCCGGATTCACCTTCA...GTGACCACTACATGGACTGGGTCCGCCAG
                121                                                       180
MH74 VH         ATGCCCGGGAAAGGCCTGGAGTGGATGGGGGCGA......TTGATCCTACTGATTCTGAT
MH73 VH         GCCCCAGGGAAGGGACTGGAGTGGATTGGACATA......TCTTTGGTGGTGGTGGGGGC
MH77 VH         GCCCCAGGGAAAGGGCTGGAGTGGATTGGCTATA......TCACCACTAGTAATGGTGCC
MH1  VH         CCCCCAGGGAAGGGGCTGGAGTGGGTTGGGAGTA......TCTATGGTAGTACTGGGAAC
MH49 VH         CCCCCAGGGAAGGGCCTGGAGTGGATTGGGAGTA......TCTATGGCAGTAGTGGGAGC
MH67 VH         CCCCCAGGGAAGGGCCTGGAGTGGATTGGGAGTA......TCTATGGCAGTAGTGGGAGC
MH36 VH         ACTCCAGGGAAGGGGCTAGAGTGGGTTGCCCGTATTAAAGTCAAAGCTGACGGTGGAACA
MH76 VH         GCTCCAGGGAAGGGGCTGGATTGGGTCTCACGCA......TTAGTAATGGTGGTGGTACC
MH2  VH         GCTCCAGGGAAGGGGCTGGAGTGGGTCTCACGTA......TTAGTAATGGTGGTGGTAGT
MH75 VH         GCTCCAGGGAAGGGGCTGGAGTGGGTCTCACGTA......TTAGTACTGGTGGTGGAACC
                181                                                       240
MH74 VH         ACCAGATACAACCCGTCCTTCCAAGGCCAGGTCACCATCTCCGCCGACAAGTCCATCAGC
MH73 VH         ACCGACTACAACCCCTCCCTCAAGAGTCGAGTCACCATTTCAACAGACACGTCCAAGAAC
MH77 VH         ACCTACTACAACCCCTCCCTCAAGAGTCGAGTCACCATTTCAACAGACACGTCCAAGAAC
MH1  VH         ACCTACTACAACCCCTCCCTCAAGAGTCGAGTCACCATTTCAACAGACACGTCCAAGAAC
MH49 VH         ACCGAATACAACCCCTCCCTCAAAAGTCGAGCCACCATTTCAAGAGACACGTCCAAGAAC
MH67 VH         ACCGAATACAACCCCTCCCTCAAAAGTCGAGCCACCATTTCAAGAGACACGTCCAAGAAC
MH36 VH         GCAGATTACGCCGCGTCTGTGAAAGGCAGATTCACCATCTCAAGAGACGATTCAAAGAAC
MH76 VH         ACATGGTACGCAGACTCCGTGAAGGGCAGATTCACCATCTCCAGAGAGAACGCCAAGAAC
MH2  VH         AAATGGTACGCAGACTCCGTGAAGGGCAGATTCACCATCTCCAGAGAGAACGCCAAGAAC
MH75 VH         ACATGGTACGCAGACTCCGTGAAGGGCAGATTCACCATCTCCAGAGAGAACGCCAACAAC
                241                                                       300
MH74 VH         ACCGCCTACCTGCAGTGGAGCAGGCTGAAGGCCTCGGACACCGCCACGTATTACTGTGCG
MH73 VH         CAGTTCTCCCTGAAGCTGAGCTCTCTGGCCGCCGCGGACACGGCCGTGTATTACTGTGCG
MH77 VH         CAGTTCTCCCTGAAACTGAGCTCTGTGACCGCCGCGGACTCGGCCGTGTATTTCTGTGCG
MH1  VH         CAGCTCTCCCTGAAGGTGAGCTCTGTGACCGCCGCGGACACGGCCATCTACTACTGTGCG
MH49 VH         CAGTTCTCCCTGAAGCTGAGCTCTGTGACCGCCGCGGACACGGCCGTCTATTACTGTGCG
MH67 VH         CAGTTCTCCCTGAAGCTGAGCTCTGTGACCGCCGCGGACACGGCCGTCTATTACTGTGCG
MH36 VH         ACACTGTATCTGCAAATGAACAGTCTGAAAACCGAGGACACGGCCGTGTATTACTGCAC.
MH76 VH         ACACTGTATCTTCAAATGAACAGCCTGAGACCTGAGGACACGGCTGTCTATTACTGTGCG
MH2  VH         ACACTGTATCTTCAAATGAACAGCCTGAGAGCTGAGGACACGGCTGTATATTACTGTGCG
MH75 VH         ACACTGTATCTTCAAATGAACAGCCTGAGAGGTGAGGACACGGCTGTCTATTACTGTGCG

                301                                                       360
MH74 VH         AAATCAGACTGGAGTGATTATTATGGCAACTCATTGGATGTCTGGGGCCGGGGAGTTCTG
MH73 VH         AGAGCT.GCAATAATGT.....ACCCCAACCGGTTCGATGTCTGGGGCCCGGGAGTCCTG
```

Figure 1 (continued)

```
MH77 VH        AGGGGATACAGTAACT......GGGACAACTGGTTCGATGTCTGGGGCCCGGGAGTCCTG
MH1  VH        AGAGCCCGCAGTGGTACTTTG.TGGTT.....CCTCGAGTTCTGGGGCCAGGGCGCCCCG
MH49 VH        AG.....GCAGATACAATTTT.TGACTGATGCTTTTGATTTCTGGGGCCAAGGGCTCAGG
MH67 VH        AG.....GCAGATACAATTTT.TGACTGATGCTTTTGATTTCTGGGGCCAAGGGCTCAGG
MH36 VH        ......CACAGAGGAGATTA..CAGTGGCCCGTTATGACTACTGGGGCCAGGGAGTCCTG
MH76 VH        ACGGTGCCCACAG.........CGACATCTGGAATAGGCAACTGGGGCCAGGGAGTCCTG
MH2  VH        GAAGTTCCCA............CGGGATACAGTCAAGGTGTCTGGGGCCCGGGAGTCCTG
MH75 VH        AAAGTTCCCA............CGGGATACAGTCAAGGGGTCTGGGGGCCGGGAGTCCTG
               361           375
MH74 VH        GTCACAGCCTCTTCA
MH73 VH        GTCACAGCCTCTAGC
MH77 VH        GTCACAGTCTCCTCA
MH1  VH        GTCACAGCATCCTCA
MH49 VH        GTCACAGTCTCCTCA
MH67 VH        GTCACAGCCTCCTCA
MH36 VH        GTCACAGTCTCCTCA
MH76 VH        GTCACAGCCTCCTCA
MH2  VH        TTCACAGTCTCCTCA
MH75 VH        GTCACAGCCTCCTCA
```

Figure 2

```
            1                                                          60
MH67 VK     GACATTCAGCTGACCCAGTCTCCATCCTCCGTGTCTGCTTCTGTGGGAGACAGAGTCACC
MH73 VK     GAGCTCCTGATGACACAGTCTCCATCCTCCCTGTCTGCATCTGTAGGAGACAGAGTCACC
MH77 VK     GACATTCAGATGTCCCAGTCTCCTTCCTCCCTGTCTGCATCTGTGGGAGACAAAGTCACC
MH2  VL     CAGTCTGTGTTGACTCAG...CCACAATCGGTGTCGGTGTCCCCAGGACAGACGGCCAGG
MH75 VL     CAGTCTGTGTTGACTCAG...CCACAATCGGTGTCGGTGTCCCCAGGACAGACGGCCAGG
MH1  VL     CAGCCTGTGCTGACTCAG...CCACGCTCAGTGTCCGTGTCCCCAGGACAGACGGCCAGG
MH76 VL     CAGCCAGGGCTGACTCAG...CCACACTCGGTGTCGGTGTCCCCAGGACAGACGGCCAGG
MH74 VL     CAGTCTGTGTTGACTCAG...CCGCCCTCAGTGTCTGGGGCGCCAGGACAGAGGGTCACC
MH36 VL     CAGTCTGTGTTGACTCAG...CCACCCTCAGCGTCTGGGGCTCCCGGGCAGAGTGTCACC
MH49 VL     CAGCCAGGGCTGACTCAG...CCTCCCTCAGCGTCTGGGGCTCCCGGGCAGAGTGTCACC

            61                                                        120
MH67 VK     ATCACTTGTCGGGCGAGTC......AGGCCAT...CAGTACTTATTTAGCCTGGTATCTA
MH73 VK     ATCTCTTGCCGGGCAAGTC...AGAACATTTA......TAGTAATTTAGCGTGGTATCAG
MH77 VK     ATCACTTGCCAGGCAAGTC......AGAGTGT...TAGCAGCTGGTTAGCCTGGTATCGG
MH2  VL     ATCTCCTGTGGGGGAGACA......ACATTGG...AAGTAAAAATGTGCACTGGTACCAG
MH75 VL     ATCACCTGTGGGGGAGACA......ACATTGG...AAGTAAAAATGTGCACTGGTACCAG
MH1  VL     ATCACCTGTGGGGGAGACA......ACATTGG...AAGTAAAAGTGTGCAGTGGTACCAG
MH76 VL     ATCACCTGTGGGGGAGACA......ACATTGG...AAGTAAAAATGTGCACTGGTACCAG
MH74 VL     ATCTCCTGCACTGGGAGTAATTCCAACATCGGGGCGGGTTATTATGTGCAGTGGTACCAG
MH36 VL     ATCTCTTGCTCTGGAAGCAGCTCCAACATCAG...AGGTAATGGTGTACACTGGTACCAG
MH49 VL     ATCTCTTGCTCTGGAAGCAGCTCTGACATTGG...AAGTCATGACGTCTACTGGTACCAG

            121                                                       180
MH67 VK     CAGAGGCCGGGGAAAGCCCCTGAACTCCTGATCTATTATGCAACCACTTTACACACTGGG
MH73 VK     CAGAAACCAGGGAAAACTCCTAAGCTCCTGATCTATGCTGCATCCATCTTGCAGAGTGGG
MH77 VK     CAGAAACCAGGGAAGGCCCCTAAGCCCCTGATCTATAAGGCATCCAGTTTGGAAGGTGGG
MH2  VL     CAGAAGCCACCGCAGGCCCCTGTGCTGGTCATCTATGCTGGAACCGAACGGCCCTCAGGG
MH75 VL     CAGAAGCCACCGCAGGCCCCTGTGCTGGTCATCTATGCTGAAACCGAGCGGCCCTCAGGG
MH1  VL     CAGAAGCCACCGCAGGCCCCTGTGCTGGTCATCTATGCTGATAGCGAACGGCCCTCAGGA
MH76 VL     CAGAAGCCACCGCAGGCCCCTGTGCTGGTCATCTATGCTGATAGCGAACGGCCCTCAGGG
MH74 VL     CAGCTTCCAGGAACGGCCCCCAAACTCCTCATCTATGAAAATAATAAGCGACCCTCAGGG
MH36 VL     CAGCTCTCAGGAATGGCCCCCAAACTCCTCATCTATAATAATAATCAGCGACCCTCAGGG
MH49 VL     CAGCTCCCAGGGACGGCCCCCAAGCTCCTCATCTACTACAGTAATCAGCGACCCTCAGGG

            181                                                       240
MH67 VK     GTCGCTTCAGGTCTCACTGGCAGTGGATCTGGGACGGATTTCACTCTCACCCTCAGTGCC
MH73 VK     ATTCCCTCTCGGTTCAGCGGCAGCGGATCTGGGACAGATTACACTCTCACCATCACCAAC
MH77 VK     GTCCCCTCAAGGTTCAGCGGCAGTGGATCTGGGACAGATTTCACTCTCACCATCAACAGC
MH2  VL     ATCCCTGAGCGATTCTCTGGCTCCAACTCCGGGAACACGGCCACCCTGACCATCAGCGGG
MH75 VL     ATCCCTGAGCGATTCTCTGGCTCCAACTCCGGGAACACGGCCACCCTGACCATCAGCGGA
MH1  VL     ATCCCTGAGCGATTCTCTGGCTCCAACTCAGGGAACACCGCCACCCTGACCGTCAGCGGG
MH76 VL     ATCCCTGAGCGATTCTCTGGCTCCAACTCCGGGAACACGGCCACCCTGACCATCAGCGGG
MH74 VL     GTTTCTGATCGATTCTCTGGCTCCAAGTCTGGTACCTCAGCCTCCCTGACCATCACTGGA
MH36 VL     GTCCCTGACCGATTCTCTGGCTCCAAGTCTGGCACGTCAGCCTCCCTGGCCATCACTGGT
MH49 VL     GTCCCTGACCGAATCTCTGGCTCCAAGTCTGGCACGTCAGCCTCCCTGACCATCAGCGGT

            241                                                       300
MH67 VK     CTGCAACCTGTAGATGTTGGAACTTACTACTGTCAACAGTTTAAAA.....CTTTACCGT
MH73 VK     CTGCAGCCTGAAGATTTTGGAACTTATTACTGTCAGCAAGGTTTTGGTATCCCCTACACT
MH77 VK     CTGCAGCCTGAAGATTTTGCAACTTATTACTGTCAACAGTATAACAGTGTGCCGTACAGT
MH2  VL     GTCGAGGCCGGGGATGAGGCGGACTATTACTGTCAGGTGTGGGACGGTACCCGTGAGCAT
MH75 VL     GTCGAGGCCGGGGATGAGGCGGACTATTACTGTCAGGTGTGGGACGGTAGCAGTGCACAT
MH1  VL     GTCGAGGCCGGGGATGAGGCTGACTATTACTGTCAGGTGTGGGACAGTAGTAGTGATCAT
MH76 VL     GTCGAGGCCGGGGATGAGGCTGACTATTACTGTCAGGTGTGGGACAGTAGCAGTAATCAT
MH74 VL     CTTCAGTCTGAGGATGAGGCTGACTATTACTGCCAGTCCTATGACAGCAGCCTGAGTGTT
MH36 VL     CTCCAGTCTGAGGATGAGGCCGATTATTACTGCGAGGCATGGGATAACAGCCTGAGCGGT
MH49 VL     CTCCGGTCCGAGGATGAGGCTGATTATTACTGTGAAACATGGGAAAACAGCCTGAGCGGT
```

Figure 2 (continued)

```
            301                                 336
MH67 VK     ACACT.TTTGGCCAGGGGACCAAAGTGGACATCAAA
MH73 VK     ......TTTGGCCAGGGGACCAAAGTGGAGTTCAAA
MH77 VK     ......TTTGGCCACGGGACCAAGGTGGACATCAAG
MH2  VL     GTATTATTCGGAGGAGGGACCCGGCTCACCGTCCTA
MH75 VL     GTATTATTCGCAGGAGGGACCCGGCTGACCGTCCTA
MH1  VL     GTGTTATTCGGAGGAGGGACCCGGCTGACCGTCCTA
MH76 VL     GTGTTATTCGGAGGAGGGACCCGGCTCACCGTACTA
MH74 VL     GTGTTATTCGGAGGAGGGACCCGGCTCACCGTCCTA
MH36 VL     GGCTTATTCGGAGGAGGGACCCGGCTGACCGTCCTA
MH49 VL     CCGGTCTTCGGCGGAGGGACCCGGCTCACCGTCCTA
```

Figure 3

MH1- QLQLQESGPGLVKPSETLSLTCAVSGGSISGGYGWGWIRQPPGKGLEWVGSIYGSTGNTYYNPSLKSRVTISTDT

MH2- EVQLVESGGGLAKPGGSLRLSCAASGFTFSDYYMDWVRQAPGKGLEWVSRISNGGSKWYADSVKGRFTISRE

MH36- EVQLVESGGGLVQPGGSLRLSCAASGFTFSNYWMNWVRQTPGKGLEWVARIKVKADGGTADYAASVKGRFTI

MH49- EAQLEESGPGLVKPSETLSLSCAVSGGSFRSYWWGWIRQPPGKGLEWIGSIYGSSGSTEYNPSLKSRATISRDTS

MH67- QVQLEQSGPGLVKPSETLSLSCAVSGGSFRSYWWGWIRQPPGKGLEWIGSIYGSSGSTEYNPSLKSRATISRDTS

MH73- QVQLQESGPGLVKPSETLSLTCAVSGGSLSSNYWSWIRQAPGKGLEWIGHIEGLGGTDYNPSLKSRVTISTDTS

MH74- EVQLVQSGAEVKRPGESLKISCKTSGYSFTSYWISWVRQMPGKGLEWMGAIDPTDSDTRYNPSFQGQVTISAD

MH75- QEQLVQSGGGLAKPGGSLRLSCADSGFTFSDHYMDWVRQAPGKGLEWVSRISTGGGTTWYADSVKGRFTISR

MH76- QVQLQESGGGLAKPGGSLRLSCAASGFTFSDYYMDWVRQAPGKGLDWVSRISNGGGTTWYADSVKGRFTISR

MH77- QVQLLESGPGLVKPSETLSLTCTVSGGSFSSHWWNWIRQAPGKGLEWIGYITTSNGATYYNPSLKSRVTISTDT

MH1- SKNQLSLKVSSVTAADTAIYYCARARSGTLWFLEFWGQGAPVTASS

MH2- NAKNTLYLQMNSLRAEDTAVYYCAEVPTGYSQGVWGPGVLFTVSS

MH36- SRDDSKNTLYLQMNSLKTEDTAVYYCTTEEITYARSDYWGQGVLVTVSS

MH49- KNQFSLKLSSVTAADTAVYYCARQIQFLTDAFDFWGQGLRVTVSS

MH67- KNQFSLKLSSVTAADTAVYYCARQIQFLTDAFDFWGQGLRVTASS

MH73- KNQFSLKLSSLAAADTAVYYCARAAIMYTNRFDYWGPGVLVTASS

MH74- KSISTAYLQWSRLKASDTATYYCAKSDWSDYYGNSLDYWGRGVLVTASS

MH75- ENANNTLYLQMNSLRGEDTAVYYCAKVPTGYSQGVWGPGVLVTASS

MH76- ENAKNTLYLQMNSLRPEDTAVYYCATVPTATSGIGYWGQGVLVTASS

MH77- SKNQFSLKLSSVTAADSAVYFCARGYSNWDNWFDYWGPGVLVTVSS

Figure 4

MH1- QPVLTQPRSVSVSPGQTARITCGGNNIGSKSVQWYQQKPPQAPVLVIYKDSERPSGIPERFSGSNSGNTATLTVS

MH2- QSVLTQPQSVSVSPGQTARISCGGNNIGSKNVHWYQQKPPQAPVLVIYSDTERPSGIPERFSGSNSGNTATLTISG

MH36- QSVLTQPPSASGAPGQSVTISCSGSSSNIRGNGVHWYQQLSGMAPKLLIYNNNQRPSGVPDRFSGSKSGTSASLAI

MH49- QPGLTQPPSASGAPGQSVTISCSGSSSDIGSHDVYWYQQLPGTAPKLLIYSSNQRPSGVPDRISGSKSGTSASLTIS

MH67- DIQLTQSPSSVSASVGDRVTITCRASQAISTYLAWYLQRPGKAPELLIYYATTLHTGVASGLTGSGSGTDFTLTLS

MH73- ELLMTQSPSSLSASVGDRVTISCRASQNIYSNLAWYQQKPGKTPKLLIYAASILQSGIPSRFSGSGSGTDYTLTITN

MH74- QSVLTQPPSVSGAPGQRVTISCTGSNSNIGAGYYVQWYQQLPGTAPKLLIYNNNKRPSGVSDRFSGSKSGTSASL

MH75- QSVLTQPQSVSVSPGQTARITCGGDNIGSKNVHWYQQKPPQAPVLVIYAETERPSGIPERFSGSNSGNTATLTIS

MH76- QPGLTQPHSVSVSPGQTARITCGGNNIGSKNVHWYQQKPPQAPVLVIYADSERPSGIPERFSGSNSGNTATLTIS

MH77- DIQMSQSPSSLSASVGDKVTITCQASQSVSSWLAWYRQKPGKAPKPLIYKASSLEGGVPSRFSGSGSGTDFTLTIN

MH1- GVEAGDEADYYCQVWDSSSDHVLFGGGTRLTVLA

MH2- VEAGDEADYYCQVWDGTREHVLFGGGTRLTVLA

MH36- TGLQSEDEADYYCEAWDNSLSGGLFGGGTRLTVLA

MH49- GLRSEDEADYYCETWENSLSGPVFGGGTRLTVLA

MH67- ALQPVDVGTYYCQQFKTLPYTFGQGTKVDIKA

MH73- LQPEDFGTYYCQQGFGIPYTFGQGTKVEFKA

MH74- TITGLQSEDEADYYCQSYDSSLSVVLFGGGTRLTVLA

MH75- GVEAGDEADYYCQVWDGSSAHVLFAGGTRLTVLA

MH76- GVEAGDEADYYCQVWDSSSNHVLFGGGTRLTVL

MH77- SLQPEDFATYYCQQYNSVPYSFGHGTKVDIKA

SEQUENCE LISTING

<160> NUMBER OF SEQ ID NOS: 152

<210> SEQ ID NO 1
<211> LENGTH: 20
<212> TYPE: DNA
<213> ORGANISM: Artificial Sequence
<220> FEATURE:
<223> OTHER INFORMATION: Primer - Lib-H1 F

<400> SEQUENCE: 1
caggagcagc tggtgcagtc 20

<210> SEQ ID NO 2
<211> LENGTH: 20
<212> TYPE: DNA
<213> ORGANISM: Artificial Sequence
<220> FEATURE:
<223> OTHER INFORMATION: Primer - Lib-H2 F

<400> SEQUENCE: 2
caggtccagc tggtgsagwc 20

<210> SEQ ID NO 3
<211> LENGTH: 20
<212> TYPE: DNA
<213> ORGANISM: Artificial Sequence
<220> FEATURE:
<223> OTHER INFORMATION: Primer - Lib-H3 F

<400> SEQUENCE: 3
caggtscagc tcgagsagtc 20

<210> SEQ ID NO 4
<211> LENGTH: 20
<212> TYPE: DNA
<213> ORGANISM: Artificial Sequence
<220> FEATURE:
<223> OTHER INFORMATION: Primer - Lib-H4 F

<400> SEQUENCE: 4
caggtgcagc tgcaggagtc 20

<210> SEQ ID NO 5
<211> LENGTH: 20
<212> TYPE: DNA
<213> ORGANISM: Artificial Sequence
<220> FEATURE:
<223> OTHER INFORMATION: Primer - Lib-H5 F

<400> SEQUENCE: 5
cagctgcagc tgcagsagtc 20

<210> SEQ ID NO 6
<211> LENGTH: 20
<212> TYPE: DNA
<213> ORGANISM: Artificial Sequence
<220> FEATURE:
<223> OTHER INFORMATION: Primer - Lib-H6 F

<400> SEQUENCE: 6
caggtgcagc trctcgagts 20

<210> SEQ ID NO 7
<211> LENGTH: 20
<212> TYPE: DNA
<213> ORGANISM: Artificial Sequence
<220> FEATURE:
<223> OTHER INFORMATION: Primer - Lib-H7 F

<400> SEQUENCE: 7
caggtscagc tggtgcagty 20

<210> SEQ ID NO 8
<211> LENGTH: 20

<212> TYPE: DNA
<213> ORGANISM: Artificial Sequence
<220> FEATURE:
<223> OTHER INFORMATION: Primer - Lib-H8 F

<400> SEQUENCE: 8
caggtsacct tgaaggagtc 20

<210> SEQ ID NO 9
<211> LENGTH: 20
<212> TYPE: DNA
<213> ORGANISM: Artificial Sequence
<220> FEATURE:
<223> OTHER INFORMATION: Primer - Lib-H9 F

<400> SEQUENCE: 9
caggtccagc tgcaggaaag 20

<210> SEQ ID NO 10
<211> LENGTH: 20
<212> TYPE: DNA
<213> ORGANISM: Artificial Sequence
<220> FEATURE:
<223> OTHER INFORMATION: Primer - Lib-H10 F

<400> SEQUENCE: 10
gaggtgcagy tggtggagwc 20

<210> SEQ ID NO 11
<211> LENGTH: 20
<212> TYPE: DNA
<213> ORGANISM: Artificial Sequence
<220> FEATURE:
<223> OTHER INFORMATION: Primer - Lib-H11 F

<400> SEQUENCE: 11
gaggttcagy tggtkgaatc 20

<210> SEQ ID NO 12
<211> LENGTH: 20
<212> TYPE: DNA
<213> ORGANISM: Artificial Sequence
<220> FEATURE:
<223> OTHER INFORMATION: Primer - Lib-H12 F

<400> SEQUENCE: 12
gaggtgcagc tggtgsartc 20

<210> SEQ ID NO 13
<211> LENGTH: 20
<212> TYPE: DNA
<213> ORGANISM: Artificial Sequence
<220> FEATURE:
<223> OTHER INFORMATION: Primer - Lib-H13 F

<400> SEQUENCE: 13
gaggtgcagc tggyrgagtc 20

<210> SEQ ID NO 14
<211> LENGTH: 20
<212> TYPE: DNA
<213> ORGANISM: Artificial Sequence
<220> FEATURE:
<223> OTHER INFORMATION: Primer - Lib-H14 F

<400> SEQUENCE: 14
gaagtgcagy tggtggagtc 20

<210> SEQ ID NO 15
<211> LENGTH: 20
<212> TYPE: DNA
<213> ORGANISM: Artificial Sequence
<220> FEATURE:
<223> OTHER INFORMATION: Primer - Lib-H15 F

<400> SEQUENCE: 15
gaggtgcagc tcgaggagtc 20

<210> SEQ ID NO 16
<211> LENGTH: 20
<212> TYPE: DNA
<213> ORGANISM: Artificial Sequence
<220> FEATURE:
<223> OTHER INFORMATION: Primer - Lib-H16 F

<400> SEQUENCE: 16
gaggtgcagc tgctcgagtc 20

<210> SEQ ID NO 17
<211> LENGTH: 17
<212> TYPE: DNA
<213> ORGANISM: Artificial Sequence
<220> FEATURE:
<223> OTHER INFORMATION: Primer - VH Rev1

<400> SEQUENCE: 17
ctgargagrc tgtgacc 17

<210> SEQ ID NO 18
<211> LENGTH: 17
<212> TYPE: DNA
<213> ORGANISM: Artificial Sequence
<220> FEATURE:
<223> OTHER INFORMATION: Primer - VH Rev2

<400> SEQUENCE: 18
ctgaggacac ggcaacc 17

<210> SEQ ID NO 19
<211> LENGTH: 20
<212> TYPE: DNA
<213> ORGANISM: Artificial Sequence
<220> FEATURE:
<223> OTHER INFORMATION: Primer - Lib-K1 F

<400> SEQUENCE: 19
gatattgtga tgayccagac 20

<210> SEQ ID NO 20
<211> LENGTH: 20
<212> TYPE: DNA
<213> ORGANISM: Artificial Sequence
<220> FEATURE:
<223> OTHER INFORMATION: Primer - Lib-K2 F

<400> SEQUENCE: 20
gatactgtga tgacccagac 20

<210> SEQ ID NO 21
<211> LENGTH: 20
<212> TYPE: DNA
<213> ORGANISM: Artificial Sequence
<220> FEATURE:
<223> OTHER INFORMATION: Primer - Lib-K3 F

<400> SEQUENCE: 21
gatatygagc tcacbcagtc 20

<210> SEQ ID NO 22
<211> LENGTH: 20
<212> TYPE: DNA
<213> ORGANISM: Artificial Sequence
<220> FEATURE:
<223> OTHER INFORMATION: Primer - Lib-K4 F

<400> SEQUENCE: 22
gatgttgyra tgactcagtc 20

<210> SEQ ID NO 23
<211> LENGTH: 20
<212> TYPE: DNA
<213> ORGANISM: Artificial Sequence
<220> FEATURE:
<223> OTHER INFORMATION: Primer - Lib-K5 F

<400> SEQUENCE: 23
gacattcagm tgwcccagtc 20

<210> SEQ ID NO 24
<211> LENGTH: 20
<212> TYPE: DNA
<213> ORGANISM: Artificial Sequence
<220> FEATURE:
<223> OTHER INFORMATION: Primer - Lib-K6 F

<400> SEQUENCE: 24
gacgttcaga tgacccagtc 20

<210> SEQ ID NO 25
<211> LENGTH: 20
<212> TYPE: DNA
<213> ORGANISM: Artificial Sequence
<220> FEATURE:
<223> OTHER INFORMATION: Primer - Lib-K7 F

<400> SEQUENCE: 25
gacatccaga tgacccagtc 20

<210> SEQ ID NO 26
<211> LENGTH: 20
<212> TYPE: DNA
<213> ORGANISM: Artificial Sequence
<220> FEATURE:
<223> OTHER INFORMATION: Primer - Lib-K8 F

<400> SEQUENCE: 26
gagctccwga tgacmcagtc 20

<210> SEQ ID NO 27
<211> LENGTH: 20
<212> TYPE: DNA
<213> ORGANISM: Artificial Sequence
<220> FEATURE:
<223> OTHER INFORMATION: Primer - Lib-K9 F

<400> SEQUENCE: 27
gaaatwgtra tgacgcagtc 20

<210> SEQ ID NO 28
<211> LENGTH: 20
<212> TYPE: DNA
<213> ORGANISM: Artificial Sequence
<220> FEATURE:
<223> OTHER INFORMATION: Primer - Lib-K10 F

<400> SEQUENCE: 28
gaaatcgagc tcacrcagtc 20

<210> SEQ ID NO 29
<211> LENGTH: 20
<212> TYPE: DNA
<213> ORGANISM: Artificial Sequence
<220> FEATURE:
<223> OTHER INFORMATION: Primer - Lib-K11 F

<400> SEQUENCE: 29
caagttatat tgactcagtc 20

<210> SEQ ID NO 30
<211> LENGTH: 20
<212> TYPE: DNA
<213> ORGANISM: Artificial Sequence
<220> FEATURE:
<223> OTHER INFORMATION: Primer - Lib-K12 F

<400> SEQUENCE: 30
gacatcgagc tcacccagtc 20

<210> SEQ ID NO 31
<211> LENGTH: 20
<212> TYPE: DNA
<213> ORGANISM: Artificial Sequence
<220> FEATURE:
<223> OTHER INFORMATION: Primer - Lib-K13 F

<400> SEQUENCE: 31
gagctcgtgt tgacacagtc 20

<210> SEQ ID NO 32
<211> LENGTH: 24
<212> TYPE: DNA
<213> ORGANISM: Artificial Sequence
<220> FEATURE:
<223> OTHER INFORMATION: Primer - Lib-K1 Rev

<400> SEQUENCE: 32
yttgakatcc agtttggtcc cggg 24

<210> SEQ ID NO 33
<211> LENGTH: 24
<212> TYPE: DNA
<213> ORGANISM: Artificial Sequence
<220> FEATURE:
<223> OTHER INFORMATION: Primor - Lib-K2 Rev

<400> SEQUENCE: 33
tttgayctcc accytggtcc ctcc 24

<210> SEQ ID NO 34
<211> LENGTH: 24
<212> TYPE: DNA
<213> ORGANISM: Artificial Sequence
<220> FEATURE:
<223> OTHER INFORMATION: Primer - Lib-K3 Rev

<400> SEQUENCE: 34
tttgatstcc actttggtcc cctg 24

<210> SEQ ID NO 35
<211> LENGTH: 24
<212> TYPE: DNA
<213> ORGANISM: Artificial Sequence
<220> FEATURE:
<223> OTHER INFORMATION: Primer - Lib-K4 Rev

<400> SEQUENCE: 35
tytgatttcc accytggtcc cttg 24

<210> SEQ ID NO 36
<211> LENGTH: 24
<212> TYPE: DNA
<213> ORGANISM: Artificial Sequence
<220> FEATURE:
<223> OTHER INFORMATION: Primer - Lib-K5 Rev

<400> SEQUENCE: 36
cttgatgtcc accttggtcc cgtg 24

<210> SEQ ID NO 37
<211> LENGTH: 24
<212> TYPE: DNA
<213> ORGANISM: Macaca mulatta

<400> SEQUENCE: 37
ttttagtacc accttggtcc cttg 24

<210> SEQ ID NO 38
<211> LENGTH: 20
<212> TYPE: DNA
<213> ORGANISM: Artificial Sequence
<220> FEATURE:
<223> OTHER INFORMATION: Primer - Lib-L1 F

<400> SEQUENCE: 38
cagccagkgc tgactcagcc 20

<210> SEQ ID NO 39
<211> LENGTH: 20
<212> TYPE: DNA
<213> ORGANISM: Artificial Sequence
<220> FEATURE:
<223> OTHER INFORMATION: Primer - Lib-L2 F

<400> SEQUENCE: 39
cagcctgkgc tgactcagyc 20

<210> SEQ ID NO 40
<211> LENGTH: 20
<212> TYPE: DNA
<213> ORGANISM: Artificial Sequence
<220> FEATURE:
<223> OTHER INFORMATION: Primer - Lib-L3 F

<400> SEQUENCE: 40
cagtctgtgy tgackcagcc 20

<210> SEQ ID NO 41
<211> LENGTH: 20
<212> TYPE: DNA

<213> ORGANISM: Artificial Sequence
<220> FEATURE:
<223> OTHER INFORMATION: Primer - Lib-L4 F

<400> SEQUENCE: 41
cagtctgccc tgactcagcc 20

<210> SEQ ID NO 42
<211> LENGTH: 20
<212> TYPE: DNA
<213> ORGANISM: Artificial Sequence
<220> FEATURE:
<223> OTHER INFORMATION: Primer - Lib-L5 F

<400> SEQUENCE: 42
cagtctgccc cgaytcagyc 20

<210> SEQ ID NO 43
<211> LENGTH: 20
<212> TYPE: DNA
<213> ORGANISM: Artificial Sequence
<220> FEATURE:
<223> OTHER INFORMATION: Primer - Lib-L6 F

<400> SEQUENCE: 43
caggctgccc ygactcagyc 20

<210> SEQ ID NO 44
<211> LENGTH: 20
<212> TYPE: DNA
<213> ORGANISM: Artificial Sequence
<220> FEATURE:
<223> OTHER INFORMATION: Primer - Lib-L7 F

<400> SEQUENCE: 44
caggcagggc tgactcagcc 20

<210> SEQ ID NO 45
<211> LENGTH: 20
<212> TYPE: DNA
<213> ORGANISM: Artificial Sequence
<220> FEATURE:
<223> OTHER INFORMATION: Primer - Lib-L8 F

<400> SEQUENCE: 45
cagactgtgg tgacccagga 20

<210> SEQ ID NO 46
<211> LENGTH: 20
<212> TYPE: DNA
<213> ORGANISM: Artificial Sequence
<220> FEATURE:
<223> OTHER INFORMATION: Primer - Lib-L9 F

<400> SEQUENCE: 46
aagcctatgc tgactcagcc 20

<210> SEQ ID NO 47
<211> LENGTH: 20
<212> TYPE: DNA
<213> ORGANISM: Artificial Sequence
<220> FEATURE:
<223> OTHER INFORMATION: Primer - Lib-L10 F

<400> SEQUENCE: 47
tcttctgrgc tgactcagga 20

<210> SEQ ID NO 48
<211> LENGTH: 20
<212> TYPE: DNA
<213> ORGANISM: Artificial Sequence
<220> FEATURE:
<223> OTHER INFORMATION: Primer - Lib-L11 F

<400> SEQUENCE: 48
tcctatgagc tgacwcagcc 20

<210> SEQ ID NO 49
<211> LENGTH: 20
<212> TYPE: DNA
<213> ORGANISM: Artificial Sequence
<220> FEATURE:
<223> OTHER INFORMATION: Primer - Lib-L12 F

<400> SEQUENCE: 49
cagsctgtgc tgactcagcc 20

<210> SEQ ID NO 50
<211> LENGTH: 20
<212> TYPE: DNA
<213> ORGANISM: Artificial Sequence
<220> FEATURE:
<223> OTHER INFORMATION: Primer - Lib-L13 F

<400> SEQUENCE: 50
cwgcctgtgc tgactcaryc 20

<210> SEQ ID NO 51
<211> LENGTH: 19
<212> TYPE: DNA
<213> ORGANISM: Artificial Sequence
<220> FEATURE:
<223> OTHER INFORMATION: Primer - Lib-L1 Rev

<400> SEQUENCE: 51
tagracggts agccgggtc 19

<210> SEQ ID NO 52
<211> LENGTH: 19
<212> TYPE: DNA
<213> ORGANISM: Artificial Sequence
<220> FEATURE:
<223> OTHER INFORMATION: Primer - Lib-L2 Rev

<400> SEQUENCE: 52
gaggayggtc aayttggtg 19

<210> SEQ ID NO 53
<211> LENGTH: 360
<212> TYPE: DNA
<213> ORGANISM: Macaca mulatta

<400> SEQUENCE: 53
gaggcgcagc tcgaggagtc gggcccagga ctggtgaagc cttcggagac cctgtccctc 60
agttgcgctg tctctggtgg ctccttcagg agttactggt ggggctggat ccgccagccc 120
ccagggaagg gcctggagtg gattgggagt atctatggca gtagtgggag caccgaatac 180
aacccctccc tcaaaagtcg agccaccatt tcaagagaca cgtccaagaa ccagttctcc 240
ctgaagctga gctctgtgac cgccgcggac acggccgtct attactgtgc gaggcagata 300
caatttttga ctgatgcttt tgatttctgg ggccaagggc tcagggtcac agtctcctca 360

<210> SEQ ID NO 54
<211> LENGTH: 360
<212> TYPE: DNA
<213> ORGANISM: Macaca mulatta

<400> SEQUENCE: 54
caggtgcagc tcgagcagtc gggcccagga ctggtgaagc cttcggagac cctgtccctc 60
agttgcgctg tctctggtgg ctccttcagg agttactggt ggggctggat ccgccagccc 120
ccagggaagg gcctggagtg gattgggagt atctatggca gtagtgggag caccgaatac 180
aacccctccc tcaaaagtcg agccaccatt tcaagagaca cgtccaagaa ccagttctcc 240
ctgaagctga gctctgtgac cgccgcggac acggccgtct attactgtgc gaggcagata 300
caatttttga ctgatgcttt tgatttctgg ggccaagggc tcagggtcac agcctcctca 360

<210> SEQ ID NO 55
<211> LENGTH: 360
<212> TYPE: DNA
<213> ORGANISM: Macaca mulatta

<400> SEQUENCE: 55
caggtgcagc tgcaggagtc gggcccagga ctggtgaagc cttcggagac cctgtccctc 60
acctgcgctg tctctggtgg ctccctcagc agtaactact ggagctggat ccgccaggcc 120
ccagggaagg gactggagtg gattggacat atctttggtg gtggtggggg caccgactac 180
aacccctccc tcaagagtcg agtcaccatt tcaacagaca cgtccaagaa ccagttctcc 240
ctgaagctga gctctctggc cgccgcggac acggccgtgt attactgtgc gagagctgca 300
ataatgtacc ccaaccggtt cgatgtctgg ggcccgggag tcctggtcac agcctctagc 360

<210> SEQ ID NO 56
<211> LENGTH: 366
<212> TYPE: DNA
<213> ORGANISM: Macaca mulatta

<400> SEQUENCE: 56
gaggtgcagc tggtgcaatc tggagcagag gtgaaaaggc ccggggagtc actgaagatc 60
tcctgtaaga cttctggata cagctttacc agctactgga tcagctgggt gcgccagatg 120
cccgggaaag gcctggagtg gatgggggcg attgatccta ctgattctga taccagatac 180
aacccgtcct tccaaggcca ggtcaccatc tccgccgaca agtccatcag caccgcctac 240
ctgcagtgga gcaggctgaa ggcctcggac accgccacgt attactgtgc gaaatcagac 300
tggagtgatt attatggcaa ctcattggat gtctggggcc ggggagttct ggtcacagcc 360
tcttca 366

<210> SEQ ID NO 57
<211> LENGTH: 354
<212> TYPE: DNA
<213> ORGANISM: Macaca mulatta

<400> SEQUENCE: 57
caggagcagc tggtgcagtc tgggggcggc ttggcaaagc ctgggggggtc cctgagactc 60 tcctgcgcag actccggatt caccttcagt gaccactaca tggactgggt ccgccaggct 120
ccagggaagg ggctggagtg ggtctcacgt attagtactg gtggtggaac cacatggtac 180
gcagactccg tgaagggcag attcaccatc tccagagaga acgccaacaa cacactgtat 240

-continued

```
cttcaaatga acagcctgag aggtgaggac acggctgtct attactgtgc gaaagttccc    300

acgggataca gtcaaggggt ctgggggccg ggagtcctgg tcacagcctc ctca          354


<210> SEQ ID NO 58
<211> LENGTH: 357
<212> TYPE: DNA
<213> ORGANISM: Macaca mulatta

<400> SEQUENCE: 58

caggtgcagc tgcaggagtc tgggggcggc ttggcaaagc ctgggggggtc cctgagactc     60

tcctgcgcag cctccggatt caccttcagt gactactaca tggactgggt ccgccaggct    120

ccagggaagg ggctggattg ggtctcacgc attagtaatg gtggtggtac cacatggtac    180

gcagactccg tgaagggcag attcaccatc tccagagaga acgccaagaa cacactgtat    240

cttcaaatga acagcctgag acctgaggac acggctgtct attactgtgc gacggtgccc    300

acagcgacat ctggaatagg caactggggc cagggagtcc tggtcacagc ctcctca       357


<210> SEQ ID NO 59
<211> LENGTH: 363
<212> TYPE: DNA
<213> ORGANISM: Macaca mulatta

<400> SEQUENCE: 59

caggtgcagc tgctcgagtc gggcccagga ctggtgaagc cttcagagac cctgtccctc     60

acctgcactg tctctggtgg ctctttcagt agtagtcatt ggtggaactg gatccgccag    120

gccccaggga aagggctgga gtggattggc tatatcacca ctagtaatgg tgccacctac    180

tacaacccct ccctcaagag tcgagtcacc atttcaacag acacgtccaa gaaccagttc    240

tccctgaaac tgagctctgt gaccgccgcg gactcggccg tgtatttctg tgcgagggga    300

tacagtaact gggacaactg gttcgatgtc tggggcccgg gagtcctggt cacagtctcc    360

tca                                                                  363


<210> SEQ ID NO 60
<211> LENGTH: 363
<212> TYPE: DNA
<213> ORGANISM: Macaca mulatta

<400> SEQUENCE: 60

cagctgcagc tgcaggagtc gggcccagga ctggtgaagc cttcagagac cctgtccctc     60

acttgcgctg tctctggtgg ctccatcagc ggtggttatg gctggggctg gatccgccag    120

cccccaggga aggggctgga gtgggttggg agtatctatg gtagtactgg gaacacctac    180

tacaacccct ccctcaagag tcgagtcacc atttcaacag acacgtccaa gaaccagctc    240

tccctgaagg tgagctctgt gaccgccgcg gacacggcca tctactactg tgcgagagcc    300

cgcagtggta ctttgtggtt cctcgagttc tggggccagg gcgccccggt cacagcatcc    360

tca                                                                  363


<210> SEQ ID NO 61
<211> LENGTH: 354
<212> TYPE: DNA
<213> ORGANISM: Macaca mulatta

<400> SEQUENCE: 61

gaggttcagt tggtggaatc tgggggcggc ttggcaaagc ctgggggggtc cctgagactc     60
```

-continued

```
tcctgcgcag cctccggatt caccttcagt gactactaca tggactgggt ccgccaggct    120

ccagggaagg ggctggagtg ggtctcacgt attagtaatg gtggtggtag taaatggtac    180

gcagactccg tgaagggcag attcaccatc tccagagaga acgccaagaa cacactgtat    240

cttcaaatga acagcctgag agctgaggac acggctgtat attactgtgc ggaagttccc    300

acgggataca gtcaaggtgt ctggggcccg ggagtcctgt tcacagtctc ctca          354
```

<210> SEQ ID NO 62
<211> LENGTH: 363
<212> TYPE: DNA
<213> ORGANISM: Macaca mulatta

<400> SEQUENCE: 62

```
gaagtgcagc tggtggagtc tgggggaggc ttggtccagc ctggggggtc cctgaggctc     60

tcctgtgcag cctctggatt caccttcagt aacgtctgga tgaactgggt ccgccagact    120

ccagggaagg ggctagagtg ggttgcccgt attaaagtca aagctgacgg tggaacagca    180

gattacgccg cgtctgtgaa aggcagattc accatctcaa gagacgattc aaagaacaca    240

ctgtatctgc aaatgaacag tctgaaaacc gaggacacgg ccgtgtatta ctgcaccaca    300

gaggagatta cagtggcccg ttatgactac tggggccagg gagtcctggt cacagtctcc    360

tca                                                                  363
```

<210> SEQ ID NO 63
<211> LENGTH: 324
<212> TYPE: DNA
<213> ORGANISM: Macaca mulatta

<400> SEQUENCE: 63

```
cagcctgtgc tgactcagcc acgctcagtg tccgtgtccc caggacagac ggccaggatc     60

acctgtgggg gagacaacat tggaagtaaa agtgtgcagt ggtaccagca gaagccaccg    120

caggcccctg tgctggtcat ctatgctgat agcgaacggc cctcaggaat ccctgagcga    180

ttctctggct ccaactcagg gaacaccgcc accctgaccg tcagcggggt cgaggccggg    240

gatgaggctg actattactg tcaggtgtgg gacagtagta gtgatcatgt gttattcgga    300

ggagggaccc ggctgaccgt ccta                                           324
```

<210> SEQ ID NO 64
<211> LENGTH: 324
<212> TYPE: DNA
<213> ORGANISM: Macaca mulatta

<400> SEQUENCE: 64

```
cagtctgtgt tgactcagcc acaatcggtg tcggtgtccc caggacagac ggccaggatc     60

tcctgtgggg gagacaacat tggaagtaaa aatgtgcact ggtaccagca gaagccaccg    120

caggcccctg tgctggtcat ctatgctgga accgaacggc cctcagggat ccctgagcga    180

ttctctggct ccaactccgg gaacacggcc accctgacca tcagcggggt cgaggccggg    240

gatgaggcgg actattactg tcaggtgtgg gacggtaccc gtgagcatgt attattcgga    300

ggagggaccc ggctcaccgt ccta                                           324
```

<210> SEQ ID NO 65
<211> LENGTH: 330
<212> TYPE: DNA
<213> ORGANISM: Macaca mulatta

<400> SEQUENCE: 65

```
cagtctgtgt tgactcagcc accctcagcg tctggggctc ccgggcagag tgtcaccatc     60

tcttgctctg gaagcagctc caacatcaga ggtaatggtg tacactggta ccagcagctc    120

tcaggaatgg cccccaaact cctcatctat aataataatc agcgaccctc aggggtccct    180

gaccgattct ctggctccaa gtctggcacg tcagcctccc tggccatcac tggtctccag    240

tctgaggatg aggccgatta ttactgcgag gcatgggata acagcctgag cggtggctta    300

ttcggaggag ggacccggct gaccgtccta                                      330


<210> SEQ ID NO 66
<211> LENGTH: 330
<212> TYPE: DNA
<213> ORGANISM: Macaca mulatta

<400> SEQUENCE: 66

cagccagggc tgactcagcc tccctcagcg tctggggctc ccgggcagag tgtcaccatc     60

tcttgctctg gaagcagctc tgacattgga agtcatgacg tctactggta ccagcagctc    120

ccagggacgg cccccaagct cctcatctac tacagtaatc agcgaccctc aggggtccct    180

gaccgaatct ctggctccaa gtctggcacg tcagcctccc tgaccatcag cggtctccgg    240

tccgaggatg aggctgatta ttactgtgaa acatgggaaa acagcctgag cggtccggtc    300

ttcggcggag ggacccggct caccgtccta                                      330


<210> SEQ ID NO 67
<211> LENGTH: 321
<212> TYPE: DNA
<213> ORGANISM: Macaca mulatta

<400> SEQUENCE: 67

gacattcagc tgacccagtc tccatcctcc gtgtctgctt ctgtgggaga cagagtcacc     60

atcacttgtc gggcgagtca ggccatcagt acttatttag cctggtatct acagaggccg    120

gggaaagccc ctgaactcct gatctattat gcaaccactt tacacactgg ggtcgcttca    180

ggtctcactg gcagtggatc tgggacggat ttcactctca ccctcagtgc cctgcaacct    240

gtagatgttg gaacttacta ctgtcaacag tttaaaactt taccgtacac ttttggccag    300

gggaccaaag tggacatcaa a                                               321


<210> SEQ ID NO 68
<211> LENGTH: 321
<212> TYPE: DNA
<213> ORGANISM: Macaca mulatta

<400> SEQUENCE: 68

gagctcctga tgacacagtc tccatcctcc ctgtctgcat ctgtaggaga cagagtcacc     60

atctcttgcc gggcaagtca gaacatttat agtaatttag cgtggtatca gcagaaacca    120

gggaaaactc ctaagctcct gatctatgct gcatccatct tgcagagtgg gattccctct    180

cggttcagcg gcagcggatc tgggacagat tacactctca ccatcaccaa cctgcagcct    240

gaagattttg gaacttatta ctgtcagcaa ggttttggta tcccctacac ttttggccag    300

gggaccaaag tggagttcaa a                                               321


<210> SEQ ID NO 69
<211> LENGTH: 333
<212> TYPE: DNA
<213> ORGANISM: Macaca mulatta
```

<400> SEQUENCE: 69
cagtctgtgt tgactcagcc gccctcagtg tctggggcgc caggacagag ggtcaccatc 60
tcctgcactg ggagtaattc caacatcggg gcgggttatt atgtgcagtg gtaccagcag 120
cttccaggaa cggcccccaa actcctcatc tatgaaaata ataagcgacc ctcaggggtt 180
tctgatcgat tctctggctc caagtctggt acctcagcct ccctgaccat cactggactt 240
cagtctgagg atgaggctga ctattactgc cagtcctatg acagcagcct gagtgttgtg 300
ttattcggag gagggacccg gctcaccgtc cta 333

<210> SEQ ID NO 70
<211> LENGTH: 324
<212> TYPE: DNA
<213> ORGANISM: Macaca mulatta

<400> SEQUENCE: 70
cagtctgtgt tgactcagcc acaatcggtg tcggtgtccc caggacagac ggccaggatc 60
acctgtgggg gagacaacat tggaagtaaa aatgtgcact ggtaccagca gaagccaccg 120
caggcccctg tgctggtcat ctatgctgaa accgagcggc cctcagggat ccctgagcga 180
ttctctggct ccaactccgg gaacacggcc accctgacca tcagcggagt cgaggccggg 240
gatgaggcgg actattactg tcaggtgtgg gacggtagca gtgcacatgt attattcgca 300
ggagggaccc ggctgaccgt ccta 324

<210> SEQ ID NO 71
<211> LENGTH: 324
<212> TYPE: DNA
<213> ORGANISM: Macaca mulatta

<400> SEQUENCE: 71
cagccagggc tgactcagcc acactcggtg tcggtgtccc caggacagac ggccaggatc 60
acctgtgggg gagacaacat tggaagtaaa aatgtgcact ggtaccagca gaagccaccg 120
caggcccctg tgctggtcat ctatgctgat agcgaacggc cctcagggat ccctgagcga 180
ttctctggct ccaactccgg gaacacggcc accctgacca tcagcggggt cgaggccggg 240
gatgaggctg actattactg tcaggtgtgg gacagtagca gtaatcatgt gttattcgga 300
ggagggaccc ggctcaccgt acta 324

<210> SEQ ID NO 72
<211> LENGTH: 321
<212> TYPE: DNA
<213> ORGANISM: Macaca mulatta

<400> SEQUENCE: 72
gacattcaga tgtcccagtc tccttcctcc ctgtctgcat ctgtgggaga caaagtcacc 60
atcacttgcc aggcaagtca gagtgttagc agctggttag cctggtatcg gcagaaacca 120
gggaaggccc ctaagcccct gatctataag gcatccagtt tggaaggtgg ggtcccctca 180
aggttcagcg gcagtggatc tgggacagat ttcactctca ccatcaacag cctgcagcct 240
gaagattttg caacttatta ctgtcaacag tataacagtg tgccgtacag ttttggccac 300
gggaccaagg tggacatcaa g 321

<210> SEQ ID NO 73
<211> LENGTH: 121
<212> TYPE: PRT
<213> ORGANISM: Macaca mulatta

<400> SEQUENCE: 73

Gln Leu Gln Leu Gln Glu Ser Gly Pro Gly Leu Val Lys Pro Ser Glu
1 5 10 15

Thr Leu Ser Leu Thr Cys Ala Val Ser Gly Gly Ser Ile Ser Gly Gly
20 25 30

Tyr Gly Trp Gly Trp Ile Arg Gln Pro Pro Gly Lys Gly Leu Glu Trp
35 40 45

Val Gly Ser Ile Tyr Gly Ser Thr Gly Asn Thr Tyr Tyr Asn Pro Ser
50 55 60

Leu Lys Ser Arg Val Thr Ile Ser Thr Asp Thr Ser Lys Asn Gln Leu
65 70 75 80

Ser Leu Lys Val Ser Ser Val Thr Ala Ala Asp Thr Ala Ile Tyr Tyr
85 90 95

Cys Ala Arg Ala Arg Ser Gly Thr Leu Trp Phe Leu Glu Phe Trp Gly
100 105 110

Gln Gly Ala Pro Val Thr Ala Ser Ser
115 120

<210> SEQ ID NO 74
<211> LENGTH: 118
<212> TYPE: PRT
<213> ORGANISM: Macaca mulatta

<400> SEQUENCE: 74

Glu Val Gln Leu Val Glu Ser Gly Gly Gly Leu Ala Lys Pro Gly Gly
1 5 10 15

Ser Leu Arg Leu Ser Cys Ala Ala Ser Gly Phe Thr Phe Ser Asp Tyr
20 25 30

Tyr Met Asp Trp Val Arg Gln Ala Pro Gly Lys Gly Leu Glu Trp Val
35 40 45

Ser Arg Ile Ser Asn Gly Gly Gly Ser Lys Trp Tyr Ala Asp Ser Val
50 55 60

Lys Gly Arg Phe Thr Ile Ser Arg Glu Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Glu Val Pro Thr Gly Tyr Ser Gln Gly Val Trp Gly Pro Gly Val
100 105 110

Leu Phe Thr Val Ser Ser
115

<210> SEQ ID NO 75
<211> LENGTH: 121
<212> TYPE: PRT
<213> ORGANISM: Macaca mulatta

<400> SEQUENCE: 75

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Val
20 25 30

Trp Met Asn Trp Val Arg Gln Thr Pro Gly Lys Gly Leu Glu Trp Val
35 40 45

Ala Arg Ile Lys Val Lys Ala Asp Gly Gly Thr Ala Asp Tyr Ala Ala
50 55 60

-continued

```
Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Glu Glu Ile Thr Val Ala Arg Tyr Asp Tyr Trp Gly
            100                 105                 110

Gln Gly Val Leu Val Thr Val Ser Ser
        115                 120


<210> SEQ ID NO 76
<211> LENGTH: 120
<212> TYPE: PRT
<213> ORGANISM: Macaca mulatta

<400> SEQUENCE: 76

Glu Ala Gln Leu Glu Glu Ser Gly Pro Gly Leu Val Lys Pro Ser Glu
1               5                   10                  15

Thr Leu Ser Leu Ser Cys Ala Val Ser Gly Gly Ser Phe Arg Ser Tyr
            20                  25                  30

Trp Trp Gly Trp Ile Arg Gln Pro Pro Gly Lys Gly Leu Glu Trp Ile
        35                  40                  45

Gly Ser Ile Tyr Gly Ser Ser Gly Ser Thr Glu Tyr Asn Pro Ser Leu
    50                  55                  60

Lys Ser Arg Ala Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Ile Gln Phe Leu Thr Asp Ala Phe Asp Phe Trp Gly Gln
            100                 105                 110

Gly Leu Arg Val Thr Val Ser Ser
        115                 120


<210> SEQ ID NO 77
<211> LENGTH: 120
<212> TYPE: PRT
<213> ORGANISM: Macaca mulatta

<400> SEQUENCE: 77

Gln Val Gln Leu Glu Gln Ser Gly Pro Gly Leu Val Lys Pro Ser Glu
1               5                   10                  15

Thr Leu Ser Leu Ser Cys Ala Val Ser Gly Gly Ser Phe Arg Ser Tyr
            20                  25                  30

Trp Trp Gly Trp Ile Arg Gln Pro Pro Gly Lys Gly Leu Glu Trp Ile
        35                  40                  45

Gly Ser Ile Tyr Gly Ser Ser Gly Ser Thr Glu Tyr Asn Pro Ser Leu
    50                  55                  60

Lys Ser Arg Ala Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Ile Gln Phe Leu Thr Asp Ala Phe Asp Phe Trp Gly Gln
            100                 105                 110

Gly Leu Arg Val Thr Ala Ser Ser
        115                 120


<210> SEQ ID NO 78
<211> LENGTH: 120
```

<212> TYPE: PRT
<213> ORGANISM: Macaca mulatta

<400> SEQUENCE: 78

Gln Val Gln Leu Gln Glu Ser Gly Pro Gly Leu Val Lys Pro Ser Glu
1               5                   10                  15

Thr Leu Ser Leu Thr Cys Ala Val Ser Gly Gly Ser Leu Ser Ser Asn
            20                  25                  30

Tyr Trp Ser Trp Ile Arg Gln Ala Pro Gly Lys Gly Leu Glu Trp Ile
        35                  40                  45

Gly His Ile Phe Gly Gly Gly Gly Gly Thr Asp Tyr Asn Pro Ser Leu
    50                  55                  60

Lys Ser Arg Val Thr Ile Ser Thr Asp Thr Ser Lys Asn Gln Phe Ser
65                  70                  75                  80

Leu Lys Leu Ser Ser Leu Ala Ala Ala Asp Thr Ala Val Tyr Tyr Cys
                85                  90                  95

Ala Arg Ala Ala Ile Met Tyr Pro Asn Arg Phe Asp Val Trp Gly Pro
            100                 105                 110

Gly Val Leu Val Thr Ala Ser Ser
        115                 120

<210> SEQ ID NO 79
<211> LENGTH: 122
<212> TYPE: PRT
<213> ORGANISM: Macaca mulatta

<400> SEQUENCE: 79

Glu Val Gln Leu Val Gln Ser Gly Ala Glu Val Lys Arg Pro Gly Glu
1               5                   10                  15

Ser Leu Lys Ile Ser Cys Lys Thr Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Ala Ile Asp Pro Thr Asp Ser Asp Thr Arg Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Arg Leu Lys Ala Ser Asp Thr Ala Thr Tyr Tyr Cys
                85                  90                  95

Ala Lys Ser Asp Trp Ser Asp Tyr Tyr Gly Asn Ser Leu Asp Val Trp
            100                 105                 110

Gly Arg Gly Val Leu Val Thr Ala Ser Ser
        115                 120

<210> SEQ ID NO 80
<211> LENGTH: 118
<212> TYPE: PRT
<213> ORGANISM: Macaca mulatta

<400> SEQUENCE: 80

Gln Glu Gln Leu Val Gln Ser Gly Gly Gly Leu Ala Lys Pro Gly Gly
1               5                   10                  15

Ser Leu Arg Leu Ser Cys Ala Asp Ser Gly Phe Thr Phe Ser Asp His
            20                  25                  30

Tyr Met Asp Trp Val Arg Gln Ala Pro Gly Lys Gly Leu Glu Trp Val
        35                  40                  45

Ser Arg Ile Ser Thr Gly Gly Gly Thr Thr Trp Tyr Ala Asp Ser Val

```
    50                  55                  60

Lys Gly Arg Phe Thr Ile Ser Arg Glu Asn Ala Asn Asn Thr Leu Tyr
65                  70                  75                  80

Leu Gln Met Asn Ser Leu Arg Gly Glu Asp Thr Ala Val Tyr Tyr Cys
                85                  90                  95

Ala Lys Val Pro Thr Gly Tyr Ser Gln Gly Val Trp Gly Gln Gly Val
            100                 105                 110

Leu Val Thr Ala Ser Ser
        115


<210> SEQ ID NO 81
<211> LENGTH: 119
<212> TYPE: PRT
<213> ORGANISM: Macaca mulatta

<400> SEQUENCE: 81

Gln Val Gln Leu Gln Glu Ser Gly Gly Gly Leu Ala Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asp Trp Val Arg Gln Ala Pro Gly Lys Gly Leu Asp Trp Val
        35                  40                  45

Ser Arg Ile Ser Asn Gly Gly Gly Thr Thr Trp Tyr Ala Asp Ser Val
    50                  55                  60

Lys Gly Arg Phe Thr Ile Ser Arg Glu Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Thr Val Pro Thr Ala Thr Ser Gly Ile Gly Asn Trp Gly Gln Gly
            100                 105                 110

Val Leu Val Thr Ala Ser Ser
        115


<210> SEQ ID NO 82
<211> LENGTH: 121
<212> TYPE: PRT
<213> ORGANISM: Macaca mulatta

<400> SEQUENCE: 82

Gln Val Gln Leu Leu Glu Ser Gly Pro Gly Leu Val Lys Pro Ser Glu
1               5                   10                  15

Thr Leu Ser Leu Thr Cys Thr Val Ser Gly Gly Ser Phe Ser Ser Ser
            20                  25                  30

His Trp Trp Asn Trp Ile Arg Gln Ala Pro Gly Lys Gly Leu Glu Trp
        35                  40                  45

Ile Gly Tyr Ile Thr Thr Ser Asn Gly Ala Thr Tyr Tyr Asn Pro Ser
    50                  55                  60

Leu Lys Ser Arg Val Thr Ile Ser Thr Asp Thr Ser Lys Asn Gln Phe
65                  70                  75                  80

Ser Leu Lys Leu Ser Ser Val Thr Ala Ala Asp Ser Ala Val Tyr Phe
                85                  90                  95

Cys Ala Arg Gly Tyr Ser Asn Trp Asp Asn Trp Phe Asp Val Trp Gly
            100                 105                 110

Pro Gly Val Leu Val Thr Val Ser Ser
        115                 120
```

<210> SEQ ID NO 83
<211> LENGTH: 109
<212> TYPE: PRT
<213> ORGANISM: Macaca mulatta

<400> SEQUENCE: 83

```
Gln Pro Val Leu Thr Gln Pro Arg Ser Val Ser Val Ser Pro Gly Gln
1               5                   10                  15

Thr Ala Arg Ile Thr Cys Gly Gly Asp Asn Ile Gly Ser Lys Ser Val
            20                  25                  30

Gln Trp Tyr Gln Gln Lys Pro Pro Gln Ala Pro Val Leu Val Ile Tyr
        35                  40                  45

Ala Asp Ser Glu Arg Pro Ser Gly Ile Pro Glu Arg Phe Ser Gly Ser
    50                  55                  60

Asn Ser Gly Asn Thr Ala Thr Leu Thr Val Ser Gly Val Glu Ala Gly
65                  70                  75                  80

Asp Glu Ala Asp Tyr Tyr Cys Gln Val Trp Asp Ser Ser Ser Asp His
                85                  90                  95

Val Leu Phe Gly Gly Gly Thr Arg Leu Thr Val Leu Ala
            100                 105
```

<210> SEQ ID NO 84
<211> LENGTH: 109
<212> TYPE: PRT
<213> ORGANISM: Macaca mulatta

<400> SEQUENCE: 84

```
Gln Ser Val Leu Thr Gln Pro Gln Ser Val Ser Val Ser Pro Gly Gln
1               5                   10                  15

Thr Ala Arg Ile Ser Cys Gly Gly Asp Asn Ile Gly Ser Lys Asn Val
            20                  25                  30

His Trp Tyr Gln Gln Lys Pro Pro Gln Ala Pro Val Leu Val Ile Tyr
        35                  40                  45

Ala Gly Thr Glu Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Gly Thr Arg Glu His
                85                  90                  95

Val Leu Phe Gly Gly Gly Thr Arg Leu Thr Val Leu Ala
            100                 105
```

<210> SEQ ID NO 85
<211> LENGTH: 111
<212> TYPE: PRT
<213> ORGANISM: Macaca mulatta

<400> SEQUENCE: 85

```
Gln Ser Val Leu Thr Gln Pro Pro Ser Ala Ser Gly Ala Pro Gly Gln
1               5                   10                  15

Ser Val Thr Ile Ser Cys Ser Gly Ser Ser Ser Asn Ile Arg Gly Asn
            20                  25                  30

Gly Val His Trp Tyr Gln Gln Leu Ser Gly Met Ala Pro Lys Leu Leu
        35                  40                  45

Ile Tyr Asn Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80
```

Ser Glu Asp Glu Ala Asp Tyr Tyr Cys Glu Ala Trp Asp Asn Ser Leu
85 90 95

Ser Gly Gly Leu Phe Gly Gly Gly Thr Arg Leu Thr Val Leu Ala
100 105 110

<210> SEQ ID NO 86
<211> LENGTH: 111
<212> TYPE: PRT
<213> ORGANISM: Macaca mulatta

<400> SEQUENCE: 86

Gln Pro Gly Leu Thr Gln Pro Pro Ser Ala Ser Gly Ala Pro Gly Gln
1 5 10 15

Ser Val Thr Ile Ser Cys Ser Gly Ser Ser Ser Asp Ile Gly Ser His
20 25 30

Asp Val Tyr Trp Tyr Gln Gln Leu Pro Gly Thr Ala Pro Lys Leu Leu
35 40 45

Ile Tyr Tyr Ser Asn Gln Arg Pro Ser Gly Val Pro Asp Arg Ile Ser
50 55 60

Gly Ser Lys Ser Gly Thr Ser Ala Ser Leu Thr Ile Ser Gly Leu Arg
65 70 75 80

Ser Glu Asp Glu Ala Asp Tyr Tyr Cys Glu Thr Trp Glu Asn Ser Leu
85 90 95

Ser Gly Pro Val Phe Gly Gly Gly Thr Arg Leu Thr Val Leu Ala
100 105 110

<210> SEQ ID NO 87
<211> LENGTH: 108
<212> TYPE: PRT
<213> ORGANISM: Macaca mulatta

<400> SEQUENCE: 87

Asp Ile Gln Leu Thr Gln Ser Pro Ser Ser Val Ser Ala Ser Val Gly
1 5 10 15

Asp Arg Val Thr Ile Thr Cys Arg Ala Ser Gln Ala Ile Ser Thr Tyr
20 25 30

Leu Ala Trp Tyr Leu Gln Arg Pro Gly Lys Ala Pro Glu Leu Leu Ile
35 40 45

Tyr Tyr Ala Thr Thr Leu His Thr Gly Val Ala Ser Gly Leu Thr Gly
50 55 60

Ser Gly Ser Gly Thr Asp Phe Thr Leu Thr Leu Ser Ala Leu Gln Pro
65 70 75 80

Val Asp Val Gly Thr Tyr Tyr Cys Gln Gln Phe Lys Thr Leu Pro Tyr
85 90 95

Thr Phe Gly Gln Gly Thr Lys Val Asp Ile Lys Ala
100 105

<210> SEQ ID NO 88
<211> LENGTH: 108
<212> TYPE: PRT
<213> ORGANISM: Macaca mulatta

<400> SEQUENCE: 88

Glu Leu Leu Met Thr Gln Ser Pro Ser Ser Leu Ser Ala Ser Val Gly
1 5 10 15

Asp Arg Val Thr Ile Ser Cys Arg Ala Ser Gln Asn Ile Tyr Ser Asn
20 25 30

```
Leu Ala Trp Tyr Gln Gln Lys Pro Gly Lys Thr Pro Lys Leu Leu Ile
        35                  40                  45

Tyr Ala Ala Ser Ile Leu Gln Ser Gly Ile Pro Ser Arg Phe Ser Gly
    50                  55                  60

Ser Gly Ser Gly Thr Asp Tyr Thr Leu Thr Ile Thr Asn Leu Gln Pro
65                  70                  75                  80

Glu Asp Phe Gly Thr Tyr Tyr Cys Gln Gln Gly Phe Gly Ile Pro Tyr
                85                  90                  95

Thr Phe Gly Gln Gly Thr Lys Val Glu Phe Lys Ala
            100                 105


<210> SEQ ID NO 89
<211> LENGTH: 112
<212> TYPE: PRT
<213> ORGANISM: Macaca mulatta

<400> SEQUENCE: 89

Gln Ser Val Leu Thr Gln Pro Pro Ser Val Ser Gly Ala Pro Gly Gln
1               5                   10                  15

Arg Val Thr Ile Ser Cys Thr Gly Ser Asn Ser Asn Ile Gly Ala Gly
            20                  25                  30

Tyr Tyr Val Gln Trp Tyr Gln Gln Leu Pro Gly Thr Ala Pro Lys Leu
        35                  40                  45

Leu Ile Tyr Glu Asn Asn Lys Arg Pro Ser Gly Val Ser Asp Arg Phe
    50                  55                  60

Ser Gly Ser Lys Ser Gly Thr Ser Ala Ser Leu Thr Ile Thr Gly Leu
65                  70                  75                  80

Gln Ser Glu Asp Glu Ala Asp Tyr Tyr Cys Gln Ser Tyr Asp Ser Ser
                85                  90                  95

Leu Ser Val Val Leu Phe Gly Gly Gly Thr Arg Leu Thr Val Leu Ala
            100                 105                 110


<210> SEQ ID NO 90
<211> LENGTH: 109
<212> TYPE: PRT
<213> ORGANISM: Macaca mulatta

<400> SEQUENCE: 90

Gln Ser Val Leu Thr Gln Pro Gln Ser Val Ser Val Ser Pro Gly Gln
1               5                   10                  15

Thr Ala Arg Ile Thr Cys Gly Gly Asp Asn Ile Gly Ser Lys Asn Val
            20                  25                  30

His Trp Tyr Gln Gln Lys Pro Pro Gln Ala Pro Val Leu Val Ile Tyr
        35                  40                  45

Ala Glu Thr Glu Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Gly Ser Ser Ala His
                85                  90                  95

Val Leu Phe Ala Gly Gly Thr Arg Leu Thr Val Leu Ala
            100                 105


<210> SEQ ID NO 91
<211> LENGTH: 107
<212> TYPE: PRT
<213> ORGANISM: Macaca mulatta
```

<400> SEQUENCE: 91

```
Gln Pro Gly Leu Thr Gln Pro His Ser Val Ser Val Ser Pro Gly Gln
1               5                   10                  15

Thr Ala Arg Ile Thr Cys Gly Gly Asp Asn Ile Gly Ser Lys Asn Val
            20                  25                  30

His Trp Tyr Gln Gln Lys Pro Pro Gln Ala Pro Val Leu Val Ile Tyr
        35                  40                  45

Ala Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Asp Ser Ser Ser Asn His
                85                  90                  95

Val Leu Phe Gly Gly Gly Thr Arg Leu Thr Val
            100                 105
```

<210> SEQ ID NO 92
<211> LENGTH: 108
<212> TYPE: PRT
<213> ORGANISM: Macaca mulatta

<400> SEQUENCE: 92

```
Asp Ile Gln Met Ser Gln Ser Pro Ser Ser Leu Ser Ala Ser Val Gly
1               5                   10                  15

Asp Lys Val Thr Ile Thr Cys Gln Ala Ser Gln Ser Val Ser Ser Trp
            20                  25                  30

Leu Ala Trp Tyr Arg Gln Lys Pro Gly Lys Ala Pro Lys Pro Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Tyr Asn Ser Val Pro Tyr
                85                  90                  95

Ser Phe Gly His Gly Thr Lys Val Asp Ile Lys Ala
            100                 105
```

<210> SEQ ID NO 93
<211> LENGTH: 7
<212> TYPE: PRT
<213> ORGANISM: Macaca mulatta

<400> SEQUENCE: 93

```
Ser Gly Gly Tyr Gly Trp Gly
1               5
```

<210> SEQ ID NO 94
<211> LENGTH: 17
<212> TYPE: PRT
<213> ORGANISM: Macaca mulatta

<400> SEQUENCE: 94

```
Ser Ile Tyr Gly Ser Thr Gly Asn Thr Tyr Tyr Asn Pro Ser Leu Lys
1               5                   10                  15

Ser
```

<210> SEQ ID NO 95
<211> LENGTH: 11

<212> TYPE: PRT
<213> ORGANISM: Macaca mulatta

<400> SEQUENCE: 95

Ala Arg Ser Gly Thr Leu Trp Phe Leu Glu Phe
1 5 10

<210> SEQ ID NO 96
<211> LENGTH: 6
<212> TYPE: PRT
<213> ORGANISM: Macaca mulatta

<400> SEQUENCE: 96

Ser Asp Tyr Tyr Met Asp
1 5

<210> SEQ ID NO 97
<211> LENGTH: 17
<212> TYPE: PRT
<213> ORGANISM: Macaca mulatta

<400> SEQUENCE: 97

Arg Ile Ser Asn Gly Gly Gly Ser Lys Trp Tyr Ala Asp Ser Val Lys
1 5 10 15

Gly

<210> SEQ ID NO 98
<211> LENGTH: 9
<212> TYPE: PRT
<213> ORGANISM: Macaca mulatta

<400> SEQUENCE: 98

Val Pro Thr Gly Tyr Ser Gln Gly Val
1 5

<210> SEQ ID NO 99
<211> LENGTH: 6
<212> TYPE: PRT
<213> ORGANISM: Macaca mulatta

<400> SEQUENCE: 99

Ser Asn Val Trp Met Asn
1 5

<210> SEQ ID NO 100
<211> LENGTH: 19
<212> TYPE: PRT
<213> ORGANISM: Macaca mulatta

<400> SEQUENCE: 100

Arg Ile Lys Val Lys Ala Asp Gly Gly Thr Ala Asp Tyr Ala Ala Ser
1 5 10 15

Val Lys Gly

<210> SEQ ID NO 101
<211> LENGTH: 10
<212> TYPE: PRT
<213> ORGANISM: Macaca mulatta

<400> SEQUENCE: 101

Glu Glu Ile Thr Val Ala Arg Tyr Asp Tyr
1 5 10

<210> SEQ ID NO 102
<211> LENGTH: 6
<212> TYPE: PRT
<213> ORGANISM: Macaca mulatta

<400> SEQUENCE: 102

Arg Ser Tyr Trp Trp Gly
1 5

<210> SEQ ID NO 103
<211> LENGTH: 17
<212> TYPE: PRT
<213> ORGANISM: Macaca mulatta

<400> SEQUENCE: 103

Ser Ile Tyr Gly Ser Ser Gly Ser Thr Glu Tyr Asn Pro Ser Leu Lys
1 5 10 15

Ser

<210> SEQ ID NO 104
<211> LENGTH: 11
<212> TYPE: PRT
<213> ORGANISM: Macaca mulatta

<400> SEQUENCE: 104

Gln Ile Gln Phe Leu Thr Asp Ala Phe Asp Phe
1 5 10

<210> SEQ ID NO 105
<211> LENGTH: 6
<212> TYPE: PRT
<213> ORGANISM: Macaca mulatta

<400> SEQUENCE: 105

Arg Ser Tyr Trp Trp Gly
1 5

<210> SEQ ID NO 106
<211> LENGTH: 17
<212> TYPE: PRT
<213> ORGANISM: Macaca mulatta

<400> SEQUENCE: 106

Ser Ile Tyr Gly Ser Ser Gly Ser Thr Glu Tyr Asn Pro Ser Leu Lys
1 5 10 15

Ser

<210> SEQ ID NO 107
<211> LENGTH: 11
<212> TYPE: PRT
<213> ORGANISM: Macaca mulatta

<400> SEQUENCE: 107

Gln Ile Gln Phe Leu Thr Asp Ala Phe Asp Phe
1 5 10

<210> SEQ ID NO 108
<211> LENGTH: 6
<212> TYPE: PRT
<213> ORGANISM: Macaca mulatta

<400> SEQUENCE: 108

Ser Ser Asn Tyr Trp Ser
1 5

<210> SEQ ID NO 109
<211> LENGTH: 17
<212> TYPE: PRT
<213> ORGANISM: Macaca mulatta

<400> SEQUENCE: 109

His Ile Phe Gly Gly Gly Gly Gly Thr Asp Tyr Asn Pro Ser Leu Lys
1 5 10 15

Ser

<210> SEQ ID NO 110
<211> LENGTH: 11
<212> TYPE: PRT
<213> ORGANISM: Macaca mulatta

<400> SEQUENCE: 110

Ala Ala Ile Met Tyr Pro Asn Arg Phe Asp Val
1 5 10

<210> SEQ ID NO 111
<211> LENGTH: 6
<212> TYPE: PRT
<213> ORGANISM: Macaca mulatta

<400> SEQUENCE: 111

Thr Ser Tyr Trp Ile Ser
1 5

<210> SEQ ID NO 112
<211> LENGTH: 17
<212> TYPE: PRT
<213> ORGANISM: Macaca mulatta

<400> SEQUENCE: 112

Ala Ile Asp Pro Thr Asp Ser Asp Thr Arg Tyr Asn Pro Ser Phe Gln
1 5 10 15

Gly

<210> SEQ ID NO 113
<211> LENGTH: 13
<212> TYPE: PRT
<213> ORGANISM: Macaca mulatta

<400> SEQUENCE: 113

Ser Asp Trp Ser Asp Tyr Tyr Gly Asn Ser Leu Asp Val
1 5 10

<210> SEQ ID NO 114
<211> LENGTH: 6
<212> TYPE: PRT
<213> ORGANISM: Macaca mulatta

<400> SEQUENCE: 114

Ser Asp His Tyr Met Asp
1 5

<210> SEQ ID NO 115
<211> LENGTH: 17
<212> TYPE: PRT
<213> ORGANISM: Macaca mulatta

<400> SEQUENCE: 115

Arg Ile Ser Thr Gly Gly Gly Thr Thr Trp Tyr Ala Asp Ser Val Lys
1 5 10 15

Gly

<210> SEQ ID NO 116
<211> LENGTH: 9
<212> TYPE: PRT
<213> ORGANISM: Macaca mulatta

<400> SEQUENCE: 116

Val Pro Thr Gly Tyr Ser Gln Gly Val
1 5

<210> SEQ ID NO 117
<211> LENGTH: 6
<212> TYPE: PRT
<213> ORGANISM: Macaca mulatta

<400> SEQUENCE: 117

Ser Asp Tyr Tyr Met Asp
1 5

<210> SEQ ID NO 118
<211> LENGTH: 17
<212> TYPE: PRT
<213> ORGANISM: Macaca mulatta

<400> SEQUENCE: 118

Arg Ile Ser Asn Gly Gly Gly Thr Thr Trp Tyr Ala Asp Ser Val Lys
1 5 10 15

Gly

<210> SEQ ID NO 119
<211> LENGTH: 10
<212> TYPE: PRT
<213> ORGANISM: Macaca mulatta

<400> SEQUENCE: 119

Val Pro Thr Ala Thr Ser Gly Ile Gly Asn
1 5 10

<210> SEQ ID NO 120
<211> LENGTH: 7
<212> TYPE: PRT
<213> ORGANISM: Macaca mulatta

<400> SEQUENCE: 120

Ser Ser Ser His Trp Trp Asn
1 5

<210> SEQ ID NO 121
<211> LENGTH: 17
<212> TYPE: PRT
<213> ORGANISM: Macaca mulatta

<400> SEQUENCE: 121

Tyr Ile Thr Thr Ser Asn Gly Ala Thr Tyr Tyr Asn Pro Ser Leu Lys
1 5 10 15

Ser

<210> SEQ ID NO 122
<211> LENGTH: 11
<212> TYPE: PRT

<213> ORGANISM: Macaca mulatta

<400> SEQUENCE: 122

Gly Tyr Ser Asn Trp Asp Asn Trp Phe Asp Val
1 5 10

<210> SEQ ID NO 123
<211> LENGTH: 10
<212> TYPE: PRT
<213> ORGANISM: Macaca mulatta

<400> SEQUENCE: 123

Gly Asp Asn Ile Gly Ser Lys Ser Val Gln
1 5 10

<210> SEQ ID NO 124
<211> LENGTH: 7
<212> TYPE: PRT
<213> ORGANISM: Macaca mulatta

<400> SEQUENCE: 124

Ala Asp Ser Glu Arg Pro Ser
1 5

<210> SEQ ID NO 125
<211> LENGTH: 14
<212> TYPE: PRT
<213> ORGANISM: Macaca mulatta

<400> SEQUENCE: 125

Gln Val Trp Asp Ser Ser Ser Asp His Val Leu Phe Gly Gly
1 5 10

<210> SEQ ID NO 126
<211> LENGTH: 10
<212> TYPE: PRT
<213> ORGANISM: Macaca mulatta

<400> SEQUENCE: 126

Gly Asp Asn Ile Gly Ser Lys Asn Val His
1 5 10

<210> SEQ ID NO 127
<211> LENGTH: 7
<212> TYPE: PRT
<213> ORGANISM: Macaca mulatta

<400> SEQUENCE: 127

Ala Gly Thr Glu Arg Pro Ser
1 5

<210> SEQ ID NO 128
<211> LENGTH: 14
<212> TYPE: PRT
<213> ORGANISM: Macaca mulatta

<400> SEQUENCE: 128

Gln Val Trp Asp Gly Thr Arg Glu His Val Leu Phe Gly Gly
1 5 10

<210> SEQ ID NO 129
<211> LENGTH: 12
<212> TYPE: PRT
<213> ORGANISM: Macaca mulatta

<400> SEQUENCE: 129

Gly Ser Ser Ser Asn Ile Arg Gly Asn Gly Val His
1 5 10

<210> SEQ ID NO 130
<211> LENGTH: 7
<212> TYPE: PRT
<213> ORGANISM: Macaca mulatta

<400> SEQUENCE: 130

Asn Asn Asn Gln Arg Pro Ser
1 5

<210> SEQ ID NO 131
<211> LENGTH: 14
<212> TYPE: PRT
<213> ORGANISM: Macaca mulatta

<400> SEQUENCE: 131

Glu Ala Trp Asp Asn Ser Leu Ser Gly Gly Leu Phe Gly Gly
1 5 10

<210> SEQ ID NO 132
<211> LENGTH: 12
<212> TYPE: PRT
<213> ORGANISM: Macaca mulatta

<400> SEQUENCE: 132

Gly Ser Ser Ser Asp Ile Gly Ser His Asp Val Tyr
1 5 10

<210> SEQ ID NO 133
<211> LENGTH: 7
<212> TYPE: PRT
<213> ORGANISM: Macaca mulatta

<400> SEQUENCE: 133

Tyr Ser Asn Gln Arg Pro Ser
1 5

<210> SEQ ID NO 134
<211> LENGTH: 14
<212> TYPE: PRT
<213> ORGANISM: Macaca mulatta

<400> SEQUENCE: 134

Glu Thr Trp Glu Asn Ser Leu Ser Gly Pro Val Phe Gly Gly
1 5 10

<210> SEQ ID NO 135
<211> LENGTH: 10
<212> TYPE: PRT
<213> ORGANISM: Macaca mulatta

<400> SEQUENCE: 135

Ala Ser Gln Ala Ile Ser Thr Tyr Leu Ala
1 5 10

<210> SEQ ID NO 136
<211> LENGTH: 7
<212> TYPE: PRT
<213> ORGANISM: Macaca mulatta

<400> SEQUENCE: 136

Tyr Ala Thr Thr Leu His Thr
1 5

<210> SEQ ID NO 137
<211> LENGTH: 12
<212> TYPE: PRT
<213> ORGANISM: Macaca mulatta

<400> SEQUENCE: 137

Gln Gln Phe Lys Thr Leu Pro Tyr Thr Phe Gly Gln
1 5 10

<210> SEQ ID NO 138
<211> LENGTH: 10
<212> TYPE: PRT
<213> ORGANISM: Macaca mulatta

<400> SEQUENCE: 138

Ala Ser Gln Asn Ile Tyr Ser Asn Leu Ala
1 5 10

<210> SEQ ID NO 139
<211> LENGTH: 7
<212> TYPE: PRT
<213> ORGANISM: Macaca mulatta

<400> SEQUENCE: 139

Ala Ala Ser Ile Leu Gln Ser
1 5

<210> SEQ ID NO 140
<211> LENGTH: 12
<212> TYPE: PRT
<213> ORGANISM: Macaca mulatta

<400> SEQUENCE: 140

Gln Gln Gly Phe Gly Ile Pro Tyr Thr Phe Gly Gln
1 5 10

<210> SEQ ID NO 141
<211> LENGTH: 13
<212> TYPE: PRT
<213> ORGANISM: Macaca mulatta

<400> SEQUENCE: 141

Gly Ser Asn Ser Asn Ile Gly Ala Gly Tyr Tyr Val Gln
1 5 10

<210> SEQ ID NO 142
<211> LENGTH: 7
<212> TYPE: PRT
<213> ORGANISM: Macaca mulatta

<400> SEQUENCE: 142

Glu Asn Asn Lys Arg Pro Ser
1 5

<210> SEQ ID NO 143
<211> LENGTH: 14
<212> TYPE: PRT
<213> ORGANISM: Macaca mulatta

<400> SEQUENCE: 143

Gln Ser Tyr Asp Ser Ser Leu Ser Val Val Leu Phe Gly Gly
1 5 10

<210> SEQ ID NO 144
<211> LENGTH: 10
<212> TYPE: PRT
<213> ORGANISM: Macaca mulatta

<400> SEQUENCE: 144

Gly Asp Asn Ile Gly Ser Lys Asn Val His
1 5 10

<210> SEQ ID NO 145
<211> LENGTH: 7
<212> TYPE: PRT
<213> ORGANISM: Macaca mulatta

<400> SEQUENCE: 145

Ala Glu Thr Glu Arg Pro Ser
1 5

<210> SEQ ID NO 146
<211> LENGTH: 14
<212> TYPE: PRT
<213> ORGANISM: Macaca mulatta

<400> SEQUENCE: 146

Gln Val Trp Asp Gly Ser Ser Ala His Val Leu Phe Ala Gly
1 5 10

<210> SEQ ID NO 147
<211> LENGTH: 10
<212> TYPE: PRT
<213> ORGANISM: Macaca mulatta

<400> SEQUENCE: 147

Gly Asp Asn Ile Gly Ser Lys Asn Val His
1 5 10

<210> SEQ ID NO 148
<211> LENGTH: 7
<212> TYPE: PRT
<213> ORGANISM: Macaca mulatta

<400> SEQUENCE: 148

Ala Asp Ser Glu Arg Pro Ser
1 5

<210> SEQ ID NO 149
<211> LENGTH: 14
<212> TYPE: PRT
<213> ORGANISM: Macaca mulatta

<400> SEQUENCE: 149

Gln Val Trp Asp Ser Ser Ser Asn His Val Leu Phe Gly Gly
1 5 10

<210> SEQ ID NO 150
<211> LENGTH: 10
<212> TYPE: PRT
<213> ORGANISM: Macaca mulatta

<400> SEQUENCE: 150

Ala Ser Gln Ser Val Ser Ser Trp Leu Ala
1 5 10

-continued

```
<210> SEQ ID NO 151
<211> LENGTH: 7
<212> TYPE: PRT
<213> ORGANISM: Macaca mulatta

<400> SEQUENCE: 151

Lys Ala Ser Ser Leu Glu Gly
1               5


<210> SEQ ID NO 152
<211> LENGTH: 12
<212> TYPE: PRT
<213> ORGANISM: Macaca mulatta

<400> SEQUENCE: 152

Gln Gln Tyr Asn Ser Val Pro Tyr Ser Phe Gly His
1               5                   10
```

ANTIBODIES DIRECTED TO RICIN TOXIN

TECHNOLOGICAL FIELD

This invention generally relates to therapeutic antibodies for treating ricin toxin poisoning.

BACKGROUND ART

References considered to be relevant as background to the presently disclosed subject matter are listed below:

[1] Sandvig, K. and van Deurs, B. (1996) Physiol Rev 76:949-966

[2] U.S. Pat. No. 5,626,844

[3] U.S. Pat. No. 8,344,109

[4] U.S. Pat. No. 8,535,668

[5] WO 2012/167346

[6] Hu, W. G., et al. (2012) Plos One 7(9): e45595

[7] Luker, G. D., et al. (2003) Nature Med 9:969-973

Acknowledgement of the above references herein is not to be inferred as meaning that these are in any way relevant to the patentability of the presently disclosed subject matter.

BACKGROUND

Ricin is a toxic glycoprotein found in the seeds of *Ricinus communis* and is composed of two polypeptide chains, A and B, joined together by a disulfide bond. Ricin was shown to inhibit protein translation in vitro by damaging the ribosome and was named "Type II ribosome inactivating protein" (Type II RIP).

The B-chain of ricin (RTB) is approximately 33 kDa and is a galactose specific lectin that is responsible for binding ricin to glycoproteins or glycolipids on the surface of cells, facilitating the entry of ricin into the cytosol. The A chain of ricin (RTA), which is the catalytic subunit of ricin, is approximately 30 kDa in size and inhibits protein synthesis irreversibly by inactivating the 28S ribosomal subunit.

Ricin comprising both A and B chains (ricin "holotoxin") is enzymatically inactive and is activated only after reduction of the disulfide bond, which allows release of the catalytically active A chain into the cytoplasm (1).

Ricin is very poisonous if inhaled, injected, or ingested and is considered as a powerful agent of bioterrorism. Ricin toxicity varies according to its penetration route, where inhalation or injection of ricin toxin is more deleterious than ingestion thereof. After ingestion and inhalation, the clinical course typically progresses over 4-36 hours. In humans, the estimated lethal dose of inhaled ricin is in the range of 1 to 10 μg/kg.

Currently, there is no specific treatment for ricin poisoning. Following exposure to ricin, treatment is mainly supportive and may include administering analogues of sugar that prevent ricin binding to its target or inhibitors of the catalytic subunit, such as azidothymidine.

In addition, various antibodies directed against ricin toxin were developed (2-6).

GENERAL DESCRIPTION

By one of its aspects the present invention provides an isolated monoclonal antibody or any antigen-binding fragment thereof which binds to ricin toxin, wherein said antibody is selected from a group consisting of:

a. a monoclonal antibody comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125, or a variant thereof;

b. a monoclonal antibody comprising a CDRH1 denoted by SEQ ID NO. 96, CDRH2 denoted by SEQ ID NO. 97, CDRH3 denoted by SEQ ID NO. 98, and a CDRL1 denoted by SEQ ID NO. 126, a CDRL2 denoted by SEQ ID NO. 127, and a CDRL3 denoted by SEQ ID NO. 128, or a variant thereof;

c. a monoclonal antibody comprising the CDRH1 denoted by SEQ ID NO. 99, CDRH2 denoted by SEQ ID NO. 100, CDRH3 denoted by SEQ ID NO. 101, and a CDRL1 denoted by SEQ ID NO. 129, a CDRL2 denoted by SEQ ID NO. 130, and a CDRL3 denoted by SEQ ID NO. 131, or a variant thereof;

d. a monoclonal antibody comprising the CDRH1 denoted by SEQ ID NO. 102, CDRH2 denoted by SEQ ID NO. 103, CDRH3 denoted by SEQ ID NO. 104, and a CDRL1 denoted by SEQ ID NO. 132, a CDRL2 denoted by SEQ ID NO. 133, and a CDRL3 denoted by SEQ ID NO. 134, or a variant thereof;

e. a monoclonal antibody comprising the CDRH1 denoted by SEQ ID NO. 105, CDRH2 denoted by SEQ ID NO. 106, CDRH3 denoted by SEQ ID NO. 107, and a CDRL1 denoted by SEQ ID NO. 135, a CDRL2 denoted by SEQ ID NO. 136, and a CDRL3 denoted by SEQ ID NO. 137, or a variant thereof;

f. a monoclonal antibody comprising the CDRH1 denoted by SEQ ID NO. 108, CDRH2 denoted by SEQ ID NO. 109, CDRH3 denoted by SEQ ID NO. 110, and a CDRL1 denoted by SEQ ID NO. 138, a CDRL2 denoted by SEQ ID NO. 139, and a CDRL3 denoted by SEQ ID NO. 140, or a variant thereof;

g. a monoclonal antibody comprising the CDRH1 denoted by SEQ ID NO. 111, CDRH2 denoted by SEQ ID NO. 112, CDRH3 denoted by SEQ ID NO. 113, and a CDRL1 denoted by SEQ ID NO. 141, a CDRL2 denoted by SEQ ID NO. 142, and a CDRL3 denoted by SEQ ID NO. 143, or a variant thereof;

h. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146, or a variant thereof;

i. a monoclonal antibody comprising the CDRH1 denoted by SEQ ID NO. 117, CDRH2 denoted by SEQ ID NO. 118, CDRH3 denoted by SEQ ID NO. 119, and a CDRL1 denoted by SEQ ID NO. 147, a CDRL2 denoted by SEQ ID NO. 148, and a CDRL3 denoted by SEQ ID NO. 149, or a variant thereof; and j. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152, or a variant thereof.

By another one of its aspects the present invention provides an isolated monoclonal antibody or any antigen-binding fragment thereof which binds to ricin toxin, wherein said antibody comprises a heavy chain variable region and a light chain variable region, wherein said heavy chain variable region is encoded by a nucleic acid sequence which is at least 70% identical to the nucleic acid sequence denoted by SEQ ID NO. 60, SEQ ID NO. 61, SEQ ID NO. 62, SEQ ID NO. 53, SEQ ID NO. 54, SEQ ID NO. 55, SEQ ID NO. 56, SEQ ID NO. 57, SEQ ID NO. 58, or SEQ ID NO. 59 and wherein said light chain variable region is encoded by a nucleic acid sequence which is at least 70% identical to SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, or SEQ ID NO. 72.

In some embodiments the isolated monoclonal antibody according to the invention comprises a heavy chain variable region comprising the amino acid sequence denoted by SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82 or a variant thereof and a light chain variable region comprising the amino acid sequence denoted by SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, or a variant thereof.

In other embodiments the isolated monoclonal antibody according to the invention is selected from a group consisting of:

a. a monoclonal antibody comprising a heavy chain variable region comprising the amino acid sequence denoted by SEQ ID NO. 73 or a variant thereof and a light chain variable region comprising the amino acid sequence denoted by SEQ ID NO. 83 or a variant thereof;

b. a monoclonal antibody comprising a heavy chain variable region comprising the amino acid sequence denoted by SEQ ID NO. 74 or a variant thereof and a light chain variable region comprising the amino acid sequence denoted by SEQ ID NO. 84 or a variant thereof;

c. a monoclonal antibody comprising a heavy chain variable region comprising the amino acid sequence denoted by SEQ ID NO. 75 or a variant thereof and a light chain variable region comprising the amino acid sequence denoted by SEQ ID NO. 85 or a variant thereof;

d. a monoclonal antibody comprising a heavy chain variable region comprising the amino acid sequence denoted by SEQ ID NO. 76 or a variant thereof and a light chain variable region comprising the amino acid sequence denoted by SEQ ID NO. 86 or a variant thereof;

e. a monoclonal antibody comprising a heavy chain variable region comprising the amino acid sequence denoted by SEQ ID NO. 77 or a variant thereof and a light chain variable region comprising the amino acid sequence denoted by SEQ ID NO. 87 or a variant thereof;

f. a monoclonal antibody comprising a heavy chain variable region comprising the amino acid sequence denoted by SEQ ID NO. 78 or a variant thereof and a light chain variable region comprising the amino acid sequence denoted by SEQ ID NO. 88 or a variant thereof;

g. a monoclonal antibody comprising a heavy chain variable region comprising the amino acid sequence denoted by SEQ ID NO. 79 or a variant thereof and a light chain variable region comprising the amino acid sequence denoted by SEQ ID NO. 89 or a variant thereof;

h. a monoclonal antibody comprising a heavy chain variable region comprising the amino acid sequence denoted by SEQ ID NO. 80 or a variant thereof and a light chain variable region comprising the amino acid sequence denoted by SEQ ID NO. 90 or a variant thereof;

i. a monoclonal antibody comprising a heavy chain variable region comprising the amino acid sequence denoted by SEQ ID NO. 81 or a variant thereof and a light chain variable region comprising the amino acid sequence denoted by SEQ ID NO. 91 or a variant thereof; and j. a monoclonal antibody comprising a heavy chain variable region comprising the amino acid sequence denoted by SEQ ID NO. 82 or a variant thereof and a light chain variable region comprising the amino acid sequence denoted by SEQ ID NO. 92 or a variant thereof.

In further embodiments the isolated monoclonal antibody according to the invention binds to ricin A chain.

In specific embodiments the isolated monoclonal antibody according to the invention comprises a heavy chain variable region comprising the amino acid sequence denoted by SEQ ID NO. 73, SEQ ID NO. 75, SEQ ID NO. 76, SEQ ID NO. 77 or SEQ ID NO. 79 and a light chain variable region denoted by SEQ ID NO. 83, SEQ ID NO. 85, SEQ ID NO. 86, SEQ ID NO. 87 or SEQ ID NO. 89.

In still further embodiments the isolated monoclonal antibody according to the invention binds to ricin B chain.

In further specific embodiments the isolated monoclonal antibody according to the invention comprises a heavy chain variable region comprising the amino acid sequence denoted by SEQ ID NO. 74, SEQ ID NO. 78, SEQ ID NO. 80, SEQ ID NO. 81 or SEQ ID NO. 82 and a light chain variable region denoted by SEQ ID NO. 84, SEQ ID NO. 88, SEQ ID NO. 90, SEQ ID NO. 91 or SEQ ID NO. 92.

In further specific embodiments the isolated monoclonal antibody according to the invention is a highly neutralizing anti ricin antibody selected from the group consisting of:

a. the monoclonal antibody denoted MH1 comprising a heavy chain variable region comprising the amino acid sequence denoted by SEQ ID NO. 73 and a light chain variable region denoted by SEQ ID NO. 83;

b. the monoclonal antibody denoted MH36 comprising a heavy chain variable region comprising the amino acid sequence denoted by SEQ ID NO. 75 and a light chain variable region denoted by SEQ ID NO. 85;

c. the monoclonal antibody denoted MH75 comprising a heavy chain variable region comprising the amino acid sequence denoted by SEQ ID NO. 80 and a light chain variable region denoted by SEQ ID NO. 90; and d. the monoclonal antibody denoted MH77 comprising a heavy chain variable region comprising the amino acid sequence denoted by SEQ ID NO. 82 and a light chain variable region denoted by SEQ ID NO. 92.

In some embodiments the isolated monoclonal antibody as herein defined is a chimeric, a humanized or a human antibody. In other embodiments, the isolated monoclonal antibody as herein defined is a chimeric antibody.

In other embodiments the isolated monoclonal antibody according to the invention is an antibody fragment selected from the group consisting of Fv, single chain Fv (scFv), heavy chain variable region, light chain variable region, Fab, $F(ab)_2$' and any combination thereof.

In further embodiments the isolated monoclonal antibody as herein defined is a neutralizing antibody.

By another one of its aspects the present invention provides a bispecific molecule comprising the antibody as herein defined.

By yet another one of its aspects the present invention provides an isolated nucleic acid molecule comprising a nucleotide sequence encoding an antibody or any antigen-binding fragment thereof according to the invention.

The present invention further provides an expression vector comprising the isolated nucleic acid molecule according to the invention and a host cell transfected with said isolated nucleic acid molecule or with the expression vector as herein defined.

By yet another one of its aspects the present invention provides an immunoconjugate comprising the antibody or any antigen-binding fragment thereof as herein defined and an additional anti-ricin agent.

In some embodiments the additional anti-ricin agent is selected from the group consisting of a sugar analogue, an inhibitor of the catalytic subunit of ricin toxin and an additional antibody.

By still another one of its aspects the present invention provides a pharmaceutical composition comprising as an active ingredient the isolated monoclonal antibody or any antigen-binding fragment thereof, the bispecific molecule or the immunoconjugate according to the invention and a pharmaceutically acceptable carrier, excipient or diluent.

In some embodiments the pharmaceutical composition according to the invention further comprises an adjuvant and/or an additional anti-ricin agent.

By yet another one of its aspects, the present invention provides the isolated monoclonal antibody or any antigen-binding fragment thereof, the bispecific molecule, the immunoconjugate or the pharmaceutical composition according to the invention for use in a method of prophylaxis, treatment or amelioration of ricin toxin poisoning.

The present invention further provides a method of prophylaxis, treatment or amelioration of ricin toxin poisoning comprising administering to a subject in need thereof a therapeutically effective amount of the isolated monoclonal antibody or any antigen-binding fragment thereof, the bispecific molecule, the immunoconjugate or the pharmaceutical composition according to the invention.

In some embodiments the method of prophylaxis, treatment or amelioration of ricin toxin poisoning as herein defined further comprises administering to a subject in need thereof an additional anti-ricin agent.

In the above and other embodiments the isolated monoclonal antibody or any antigen-binding fragment thereof, bispecific molecule, immunoconjugate or pharmaceutical composition is administered to said subject prior to or after exposure to ricin toxin.

In some embodiments the isolated monoclonal antibody or any antigen-binding fragment thereof, bispecific molecule, immunoconjugate or pharmaceutical composition according to the invention is administered to said subject immediately after exposure to ricin toxin or between about 1 to about 72 hours after exposure to ricin toxin.

In other embodiments the antibody as herein defined is administered at a therapeutically effective amount. The treating physician would be able to determine the appropriate therapeutic dosage depending on various clinical parameters of the patient as is well known in the art. A therapeutically effective amount of the antibody is for example between about 10 μg/kg to about 50 mg/kg. Non-limiting examples of dosage forms include 1 mg/kg, 2 mg/kg, 3 mg/kg, 3.3 mg/kg, 5 mg/kg, 10 mg/kg, 20 mg/kg, 30 mg/kg, 40 mg/kg and 50 mg/kg.

In further embodiments the isolated monoclonal antibody or any antigen-binding fragment thereof, bispecific molecule, immunoconjugate or pharmaceutical composition as herein defined is administered to said subject as a single dose or as multiple doses.

The present invention further provides a method of neutralizing ricin poisoning comprising administering to a subject in need thereof a therapeutically effective amount of the isolated monoclonal antibody or any antigen-binding fragment thereof, the bispecific molecule, the immunoconjugate or the pharmaceutical composition according to the invention.

By still another one of its aspects the present invention provides a method of detecting ricin toxin in a biological sample obtained from a subject, said method comprising:

(a) contacting said biological sample with the isolated monoclonal antibody or any antigen-binding fragment thereof according to the invention, wherein said monoclonal antibody is labeled with a detectable marker; and (b) detecting said isolated monoclonal antibody or any antigen-binding fragment thereof;

wherein the presence of said isolated monoclonal antibody or any antigen-binding fragment thereof indicates the presence of ricin toxin in said biological sample.

The present invention further provides a kit for detecting ricin toxin comprising:

(c) at least one labeled isolated monoclonal antibody or any antigen-binding fragment thereof according to the invention;

(d) means for detection of said labeled isolated monoclonal antibody; and optionally (e) instructions for use of said kit.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 Multiple Alignment of the heavy chain nucleic acid sequences of the antibodies MH1, MH2, MH36, MH49, MH67, MH73, MH74, MH75, MH76, and MH77. Nucleic acid sequences of the heavy chains of the indicated antibodies are shown as a multiple alignment.

FIG. 2 Multiple Alignment of the light chain nucleic acid sequences of the antibodies MH1, MH2, MH36, MH49, MH67, MH73, MH74, MH75, MH76, and MH77. Nucleic acid sequences of the light chains of the indicated antibodies are shown as a multiple alignment.

FIG. 3 Amino acid sequences of the heavy chain variable domains of the antibodies MH1, MH2, MH36, MH49, MH67, MH73, MH74, MH75, MH76, and MH77 Amino acid sequences of the heavy chains of the indicated antibodies are shown as a multiple alignment. The complementarity determining regions (CDRs) are shown in grey boxes.

FIG. 4 Amino acid sequences of the light chain variable domains of the antibodies MH1, MH2, MH36, MH49, MH67, MH73, MH74, MH75, MH76, and MH77 Amino acid sequences of the light chains of the indicated antibodies are shown as a multiple alignment. The CDRs are shown in grey boxes.

FIG. 5A shows a bar graph showing the binding of the indicated antibodies to Ricin, Ricin A chain (RTA) and Ricin B chain (RTB), using an ELISA assay. FIG. 5B shows a graph showing the binding of antibody MH73 to Ricin, RTA and RTB, using Biolayer Interferometry. Abbreviations: RTA, Ricin A chain; RTB, Ricin B chain; O.D., optical density.

DETAILED DESCRIPTION OF EMBODIMENTS

Figure 5A:
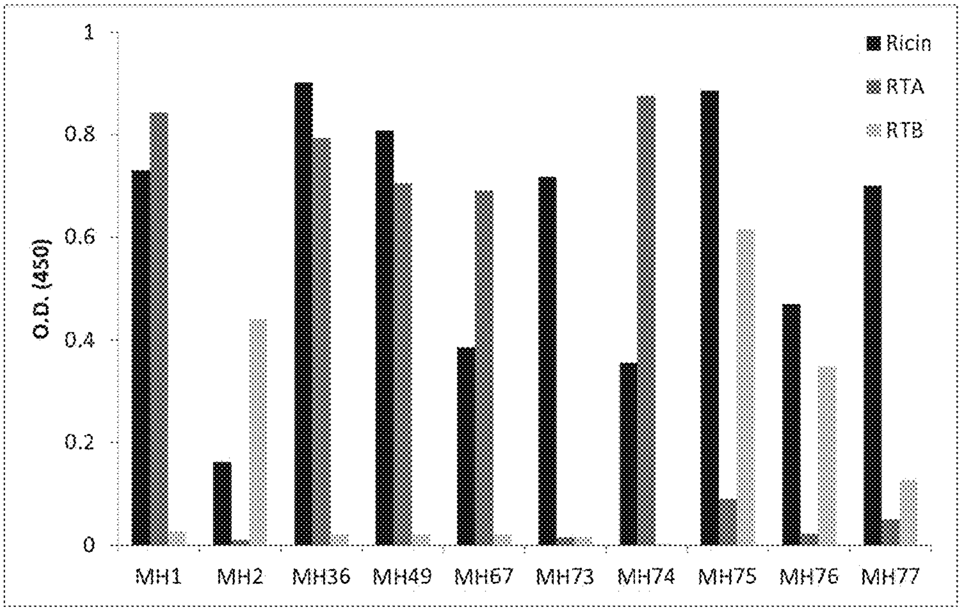
FIGS. 5A and 5B Screening the binding activity of antibodies MH1, MH2, MH36, MH49, MH67, MH73, MH74, MH75, MH76, and MH77 to Ricin.

The present disclosure is based on the preparation of monoclonal antibodies directed against the ricin toxin that are able to neutralize the activity of the toxin, as described below and demonstrated in the Examples.

Therefore the present disclosure provides an isolated monoclonal antibody or any antigen-binding fragment thereof which binds to ricin toxin, wherein said antibody is selected from a group consisting of:

a. a monoclonal antibody, comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125, or a variant thereof;

b. a monoclonal antibody comprising a CDRH1 denoted by SEQ ID NO. 96, CDRH2 denoted by SEQ ID NO. 97, CDRH3 denoted by SEQ ID NO. 98, and a CDRL1 denoted by SEQ ID NO. 126, a CDRL2 denoted by SEQ ID NO. 127, and a CDRL3 denoted by SEQ ID NO. 128, or a variant thereof;

c. a monoclonal antibody comprising the CDRH1 denoted by SEQ ID NO. 99, CDRH2 denoted by SEQ ID NO. 100, CDRH3 denoted by SEQ ID NO. 101, and a CDRL1 denoted by SEQ ID NO. 129, a CDRL2 denoted by SEQ ID NO. 130, and a CDRL3 denoted by SEQ ID NO. 131, or a variant thereof;

d. a monoclonal antibody comprising the CDRH1 denoted by SEQ ID NO. 102, CDRH2 denoted by SEQ ID NO. 103, CDRH3 denoted by SEQ ID NO. 104, and a CDRL1 denoted by SEQ ID NO. 132, a CDRL2 denoted by SEQ ID NO. 133, and a CDRL3 denoted by SEQ ID NO. 134, or a variant thereof;

e. a monoclonal antibody comprising the CDRH1 denoted by SEQ ID NO. 105, CDRH2 denoted by SEQ ID NO. 106, CDRH3 denoted by SEQ ID NO. 107, and a CDRL1 denoted by SEQ ID NO. 135, a CDRL2 denoted by SEQ ID NO. 136, and a CDRL3 denoted by SEQ ID NO. 137, or a variant thereof;

f. a monoclonal antibody comprising the CDRH1 denoted by SEQ ID NO. 108, CDRH2 denoted by SEQ ID NO. 109, CDRH3 denoted by SEQ ID NO. 110, and a CDRL1 denoted by SEQ ID NO. 138, a CDRL2 denoted by SEQ ID NO. 139, and a CDRL3 denoted by SEQ ID NO. 140, or a variant thereof;

g. a monoclonal antibody comprising the CDRH1 denoted by SEQ ID NO. 111, CDRH2 denoted by SEQ ID NO. 112, CDRH3 denoted by SEQ ID NO. 113, and a CDRL1 denoted by SEQ ID NO. 141, a CDRL2 denoted by SEQ ID NO. 142, and a CDRL3 denoted by SEQ ID NO. 143, or a variant thereof;

h. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146, or a variant thereof;

i. a monoclonal antibody comprising the CDRH1 denoted by SEQ ID NO. 117, CDRH2 denoted by SEQ ID NO. 118, CDRH3 denoted by SEQ ID NO. 119, and a CDRL1 denoted by SEQ ID NO. 147, a CDRL2 denoted by SEQ ID NO. 148, and a CDRL3 denoted by SEQ ID NO. 149, or a variant thereof; and j. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152, or a variant thereof.

The term "ricin toxin" refers to a glycoprotein found in the seeds of *Ricinus communis* (*R. communis*, also known as castor oil plant). These seeds are also referred to herein as "castor beans". Ricin toxin is composed of two polypeptide chains, A and B, joined together by a disulfide bond. The ricin toxin may be prepared using any method known in the art, for example by extraction from seeds of *R. communis*, as described in the Examples below.

As indicated above, the present invention provides isolated monoclonal antibodies that bind to ricin toxin. The term "antibody" refers to a polypeptide encoded by an immunoglobulin gene or functional fragments thereof that specifically binds and recognizes an antigen, namely ricin toxin.

The term "monoclonal antibody", "monoclonal antibodies" or "mAb" as herein defined refers to a population of substantially homogenous antibodies, i.e., the individual antibodies comprising the population are identical except for possibly naturally occurring mutations that may be present in minor amounts. Monoclonal antibodies are directed against a single antigenic site (epitope).

Monoclonal antibodies may be prepared and purified by any method known in the art. For example, monoclonal antibodies may be prepared from B cells taken from the spleen or lymph nodes of immunized animals (e.g. rats, mice or monkeys), by fusion with immortalized B cells under conditions which favor the growth of hybrid cells.

Immunization of animals may be carried out by any method known in the art, for example by immunizing monkeys, as described below. The immunized monkeys are then sacrificed and samples are taken from their blood and lymphatic nodes in order to isolate mRNA that will be used for variable heavy and variable light (VH/VL) chain amplification and further used for example for constructing a phage display library, in order to select active antibodies. Based on the results obtained from a phage display library, full length antibodies are produced, as known in the art and as described below.

Purification of monoclonal antibodies may be performed using any method known in the art, for example by affinity chromatography, namely, by using an affinity column to which a specific epitope (or antigen) is conjugated. Alternatively purification of antibodies may be based on using protein A column chromatography, as described below.

An exemplary antibody structural unit comprises a tetramer, as known in the art. Each tetramer is composed of two identical pairs of polypeptide chains, each pair having one "light chain" and one "heavy chain". The N-terminus of each chain defines a variable region of about 100 to 110 or more amino acids primarily responsible for antigen (or epitope) recognition.

Thus, the terms "heavy chain variable region" ($V_H$) and "light chain variable region" ($V_L$) refer to these heavy and light chains, respectively. More specifically, the variable region is subdivided into hypervariable and framework (FR) regions. Hypervariable regions have a high ratio of different amino acids in a given position, relative to the most common amino acid in that position. Four FR regions which have more stable amino acids sequences separate the hypervariable regions. The hypervariable regions directly contact a portion of the antigen's surface. For this reason, hypervariable regions are herein referred to as "complementarity determining regions", or "CDRs", the CDRs are positioned either at the heavy chain of the antibody ("a heavy chain complementarity determining region") or at the light chain of the antibody (a "light chain complementarity determining region").

From N-terminal to C-terminal, both light and heavy chains comprise the domains FR1, CDR1, FR2, CDR2, FR3, CDR3 and FR4. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

Thus, the complementarity determining regions CDRH1, CDRH2 and CDRH3 refer to the three complementarity determining regions starting from the N-terminus of the antibody's heavy chain (also referred to herein as heavy chain complementarity determining region) and the complementarity determining regions CDRL1, CDRL2 and CDRL3 refer to the three complementarity determining regions starting from the N-terminus of the antibody's light chain (also referred to herein as light chain complementarity determining region).

For example, as demonstrated in FIG. 3 in the context of the heavy chain of the antibody referred to herein as "MH1", CDRH1, CDRH2 and CDRH3 appear as grey boxes in the amino acid sequence of the heavy chain of the antibody. The respective CDRL1, CDRL2 and CDRL3 of the antibody referred to herein as MH1, appear in FIG. 4 in the context of the light chain of the antibody.

Binding of antibodies or antigen-binding fragments thereof to ricin toxin may be determined using any method known in the art, for example using an ELISA assay as described below or BlAcore analysis.

In some embodiments the isolated monoclonal antibody according to the invention comprises the CDRH1 denoted by SEQ ID NO. 93, CDRH2 denoted by SEQ ID NO. 94, and CDRH3 denoted by SEQ ID NO. 95, and the CDRL1 denoted by SEQ ID NO. 123, CDRL2 denoted by SEQ ID NO. 124, and the CDRL3 denoted by SEQ ID NO. 125, or a variant thereof.

In other embodiments the isolated monoclonal antibody as herein defined comprises the CDRH1 denoted by SEQ ID NO. 96, CDRH2 denoted by SEQ ID NO. 97, and the CDRH3 denoted by SEQ ID NO. 98, and the CDRL1 denoted by SEQ ID NO. 126, CDRL2 denoted by SEQ ID NO. 127, and the CDRL3 denoted by SEQ ID NO. 128, or a variant thereof.

In further embodiments the isolated monoclonal antibody as herein defined comprises the CDRH1 denoted by SEQ ID NO. 99, CDRH2 denoted by SEQ ID NO. 100, and the CDRH3 denoted by SEQ ID NO. 101, and the CDRL1 denoted by SEQ ID NO. 129, CDRL2 denoted by SEQ ID NO. 130, and the CDRL3 denoted by SEQ ID NO. 131, or a variant thereof.

In still further embodiments the isolated monoclonal antibody as herein defined comprises the CDRH1 denoted by SEQ ID NO. 102, CDRH2 denoted by SEQ ID NO. 103, and the CDRH3 denoted by SEQ ID NO. 104, and the CDRL1 denoted by SEQ ID NO. 132, CDRL2 denoted by SEQ ID NO. 133, and the CDRL3 denoted by SEQ ID NO. 134, or a variant thereof.

In some embodiments the isolated monoclonal antibody as herein defined comprises the CDRH1 denoted by SEQ ID NO. 105, CDRH2 denoted by SEQ ID NO. 106, and the CDRH3 denoted by SEQ ID NO. 107, and the CDRL1 denoted by SEQ ID NO. 135, CDRL2 denoted by SEQ ID NO. 136, and the CDRL3 denoted by SEQ ID NO. 137, or a variant thereof.

In other embodiments the isolated monoclonal antibody as herein defined comprises the CDRH1 denoted by SEQ ID NO. 108, CDRH2 denoted by SEQ ID NO. 109, and the CDRH3 denoted by SEQ ID NO. 110, and the CDRL1 denoted by SEQ ID NO. 138, CDRL2 denoted by SEQ ID NO. 139, and the CDRL3 denoted by SEQ ID NO. 140, or a variant thereof.

In further embodiments the isolated monoclonal antibody according to the invention comprises the CDRH1 denoted by SEQ ID NO. 111, CDRH2 denoted by SEQ ID NO. 112, and the CDRH3 denoted by SEQ ID NO. 113, and the CDRL1 denoted by SEQ ID NO. 141, CDRL2 denoted by SEQ ID NO. 142, and the CDRL3 denoted by SEQ ID NO. 143, or a variant thereof.

In still further embodiments the isolated monoclonal antibody as herein defined comprises the CDRH1 denoted by SEQ ID NO. 114, CDRH2 denoted by SEQ ID NO. 115, and the CDRH3 denoted by SEQ ID NO. 116, and the CDRL1 denoted by SEQ ID NO. 144, CDRL2 denoted by SEQ ID NO. 145, and the CDRL3 denoted by SEQ ID NO. 146, or a variant thereof.

In yet further embodiments the isolated monoclonal antibody as herein defined comprises the CDRH1 denoted by SEQ ID NO. 117, CDRH2 denoted by SEQ ID NO. 118, and the CDRH3 denoted by SEQ ID NO. 119, and the CDRL1 denoted by SEQ ID NO. 147, CDRL2 denoted by SEQ ID NO. 148, and the CDRL3 denoted by SEQ ID NO. 149, or a variant thereof.

In some embodiments the isolated monoclonal antibody as herein defined comprises the CDRH1 denoted by SEQ ID NO. 120, CDRH2 denoted by SEQ ID NO. 121, and the CDRH3 denoted by SEQ ID NO. 122, and the CDRL1 denoted by SEQ ID NO. 150, CDRL2 denoted by SEQ ID NO. 151, and the CDRL3 denoted by SEQ ID NO. 152, or a variant thereof.

The CDRs of the antibodies referred to herein are presented in Table 4 as well as in the context of their respective heavy and light chain sequences, e.g. in FIG. 3 and in FIG. 4, respectively.

By the term "variant" it is meant sequences of amino acids or nucleotides that are different from the sequences specifically identified herein, namely, in which one or more amino acid residues or nucleotides are deleted, substituted or added.

It should be appreciated that by the term "added", as used herein it is meant any addition(s) of amino acid residues to the sequences described herein. For example, the variant antibodies of the invention may be extended at their N-terminus and/or C-terminus with various identical or different amino acid residues.

Variants also encompass various amino acid substitutions. An amino acid "substitution" is the result of replacing one amino acid with another amino acid which has similar or different structural and/or chemical properties Amino acid substitutions may be made on the basis of similarity in polarity, charge, solubility, hydrophobicity, hydrophilicity, and/or the amphipathic nature of the residues involved.

Variants further encompass conservative amino acid substitutions. Conservative substitution tables providing functionally similar amino acids are well known in the art. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

As used herein, the term "amino acid" or "amino acid residue" refers to naturally occurring and synthetic amino acids, as well as amino acid analogs and amino acid mimetics that function in a manner similar to the naturally occurring amino acids.

Variant sequences refer to amino acid or nucleic acids sequences that may be characterized by the percentage of the identity of their amino acid or nucleotide sequences, respectively, with the amino acid or nucleotide sequences described herein (namely the amino acid or nucleotide sequences of the heavy and light chains of the antibodies herein described).

Therefore in some embodiments, variant sequences as herein defined refer to nucleic acid sequences that encode the heavy and light chain variable regions, each having a sequence of nucleotides with at least 70% or 75% of sequence identity, around 80% or 85% of sequence identity, around 90%, 91%, 92%, 93%, 94%, 95%, 96%, 97%, 98% or 99% of sequence identity when compared to the sequences of the heavy and light chain variable regions described herein.

In some embodiments the isolated monoclonal antibody or any antigen-binding fragment thereof according to the invention is wherein said antibody comprises a heavy chain variable region and a light chain variable region, wherein said heavy chain variable region is encoded by a nucleic acid sequence which is at least 70% identical to the nucleic acid sequence denoted by SEQ ID NO. 60, SEQ ID NO. 61, SEQ ID NO. 62, SEQ ID NO. 53, SEQ ID NO. 54, SEQ ID NO. 55, SEQ ID NO. 56, SEQ ID NO. 57, SEQ ID NO. 58, or SEQ ID NO. 59 and wherein said light chain variable region is encoded by a nucleic acid sequence which is at least 70% identical to SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, or SEQ ID NO. 72.

In other embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 60 and wherein the light chain variable region of the antibody is encoded by a nucleic acid sequence which is at least 70% identical to SEQ ID NO. 63.

In further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 61 and wherein the light chain variable region of the antibody is encoded by a nucleic acid sequence which is at least 70% identical to SEQ ID NO. 64.

In still further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 62 and wherein the light chain variable region of the antibody is encoded by a nucleic acid sequence which is at least 70% identical to SEQ ID NO. 65.

In some embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 53 and wherein the light chain variable region of the antibody is encoded by a nucleic acid sequence which is at least 70% identical to SEQ ID NO. 66.

In other embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 54 and wherein the light chain variable region of the antibody is encoded by a nucleic acid sequence which is at least 70% identical to SEQ ID NO. 67.

In further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 55 and wherein the light chain variable region of the antibody is encoded by a nucleic acid sequence which is at least 70% identical to SEQ ID NO. 68.

In still further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 56 and wherein the light chain variable region of the antibody is encoded by a nucleic acid sequence which is at least 70% identical to SEQ ID NO. 69.

In some embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 57 and wherein the light chain variable region of the antibody is encoded by a nucleic acid sequence which is at least 70% identical to SEQ ID NO. 70.

In other embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 58 and wherein the light chain variable region of the antibody is encoded by a nucleic acid sequence which is at least 70% identical to SEQ ID NO. 71.

In further embodiments the isolated monoclonal antibody or any antigen-binding fragment thereof according to the invention is wherein the heavy chain variable region of the antibody is encoded by a nucleic acid sequence which is at least 70% identical to the nucleic acid sequence denoted by SEQ ID NO. 59 and wherein the light chain variable region of the antibody is encoded by a nucleic acid sequence which is at least 70% identical to SEQ ID NO. 72.

In further embodiments the isolated monoclonal antibody according to the invention is wherein said antibody comprises a heavy chain variable region comprising the amino acid sequence denoted by SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, SEQ ID NO. 82 or a variant thereof and a light chain variable region comprising the amino acid sequence denoted by SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, SEQ ID NO. 92, or a variant thereof.

In specific embodiments the isolated monoclonal antibody according to the invention comprises a heavy chain variable region comprising the amino acid sequence denoted by SEQ ID NO. 73 or a variant thereof and a light chain variable region comprising the amino acid sequence denoted by SEQ ID NO. 83, or a variant thereof.

In other embodiments the isolated monoclonal antibody according to the invention comprises a heavy chain variable region comprising the amino acid sequence denoted by SEQ ID NO. 74 or a variant thereof and a light chain variable region comprising the amino acid sequence denoted by SEQ ID NO. 84, or a variant thereof.

In further embodiments the isolated monoclonal antibody according to the invention comprises a heavy chain variable region comprising the amino acid sequence denoted by SEQ ID NO. 75 or a variant thereof and a light chain variable region comprising the amino acid sequence denoted by SEQ ID NO. 85, or a variant thereof.

In still further embodiments the isolated monoclonal antibody according to the invention comprises a heavy chain variable region comprising the amino acid sequence denoted by SEQ ID NO. 76 or a variant thereof and a light chain variable region comprising the amino acid sequence denoted by SEQ ID NO. 86, or a variant thereof.

In some embodiments the isolated monoclonal antibody according to the invention comprises a heavy chain variable region comprising the amino acid sequence denoted by SEQ ID NO. 77 or a variant thereof and a light chain variable region comprising the amino acid sequence denoted by SEQ ID NO. 87, or a variant thereof.

In other embodiments the isolated monoclonal antibody according to the invention comprises a heavy chain variable region comprising the amino acid sequence denoted by SEQ ID NO. 78 or a variant thereof and a light chain variable region comprising the amino acid sequence denoted by SEQ ID NO. 88, or a variant thereof.

In further embodiments the isolated monoclonal antibody according to the invention comprises a heavy chain variable region comprising the amino acid sequence denoted by SEQ ID NO. 79 or a variant thereof and a light chain variable region comprising the amino acid sequence denoted by SEQ ID NO. 89, or a variant thereof.

In still further embodiments the isolated monoclonal antibody according to the invention comprises a heavy chain variable region comprising the amino acid sequence denoted by SEQ ID NO. 80 or a variant thereof and a light chain variable region comprising the amino acid sequence denoted by SEQ ID NO. 90, or a variant thereof.

In yet further embodiments the isolated monoclonal antibody according to the invention comprises a heavy chain variable region comprising the amino acid sequence denoted by SEQ ID NO. 81 or a variant thereof and a light chain variable region comprising the amino acid sequence denoted by SEQ ID NO. 91, or a variant thereof.

In some specific embodiments the isolated monoclonal antibody according to the invention comprises a heavy chain variable region comprising the amino acid sequence denoted by SEQ ID NO. 82 or a variant thereof and a light chain variable region comprising the amino acid sequence denoted by SEQ ID NO. 92, or a variant thereof.

As demonstrated in FIG. 5, all of the monoclonal antibodies prepared as described herein showed high binding affinity to ricin toxin, five of which (namely the antibodies referred to herein as MH1, MH36, MH49, MH67 and MH74) were shown to bind the RTA subunit; five of which (namely the antibodies referred to herein as MH2, MH75, MH76 and MH77 and MH73) were shown to bind the RTB subunit.

As demonstrated in Example 4, antibodies of the invention exhibited a substantial efficacy with regard to protection from ricin intoxication, further resulting in very high percentages of mice survival after ricin intoxication (83% to 100% survival). Therefore, in a specific embodiment the invention provides an isolated monoclonal antibody or any antigen-binding fragment thereof which binds to ricin toxin, wherein administration of said antibody results in significant protection of the infected subjects against ricin intoxication. The protective effect can be measured for example in animal models of ricin intoxication as shown in Example 4 below. Significant protection is understood as survival of at least about 80%, or at least about 83%, or at least about 85%, or at least about 90% of infected animals. It should be noted that administration of certain antibodies results in between 95% and 100% survival of infected animals (namely, 95%, 96%, 97%, 98%, 99% or 100% survival of the animals).

Specifically, the antibodies designated MH73, MH36, MH75, MH1 and MH77 showed significant protection of infected mice against ricin intoxication in an in vivo protection model. All these antibodies showed protection percentage higher than 83%. More specifically, each of the antibodies MH36, MH75, MH1 and MH77 showed protection percentage higher than 95%.

Therefore, in a specific embodiment, the present invention provides an isolated monoclonal antibody or any antigen-binding fragment thereof which binds to ricin toxin, selected from the group consisting of the antibodies designated MH73, MH36, MH75, MH1 and MH77. In another specific embodiment, the present invention provides an isolated monoclonal antibody or any antigen-binding fragment thereof which binds to ricin toxin, selected from the group consisting of the antibodies designated MH36, MH75, MH1 and MH77. The amino acid sequences of the heavy chain variable region and the light chain variable region of each of these antibodies are specified below.

As indicated above, the ricin toxin is composed of two polypeptide chains, A and B, joined together by a disulfide bond.

Therefore the term "ricin A chain" as used herein and as known in the art, refers to the A chain of ricin (RTA), which is the catalytic subunit of the glycoprotein. RTA is approximately 30 kDa in size. In some embodiments RTA may be prepared for example by extracting the toxin from seeds of *R. communis* and subjecting the obtained extract to reducing conditions and further separation steps, thereby separating the A chain from the B chain, as described for example below.

Therefore in some embodiments the isolated monoclonal antibody according to the invention binds to ricin A chain.

In specific embodiments the isolated monoclonal antibody as herein defined comprises a heavy chain variable region comprising the amino acid sequence denoted by SEQ ID NO. 73, SEQ ID NO. 75, SEQ ID NO. 76, SEQ ID NO. 77, or SEQ ID NO. 79 and a light chain variable region comprising the amino acid sequence denoted by SEQ ID NO. 83, SEQ ID NO. 85, SEQ ID NO. 86, SEQ ID NO. 87, or SEQ ID NO. 89.

In other words, in some embodiments the isolated monoclonal antibody according to the invention is the antibody also referred to herein as "MH1", namely an antibody comprising a heavy chain variable region comprising the amino acid sequence denoted by SEQ ID NO. 73 and a light chain variable region comprising the amino acid sequence denoted by SEQ ID NO. 83.

In other embodiments the isolated monoclonal antibody according to the invention is the antibody also referred to herein as "MH36", namely an antibody comprising a heavy chain variable region comprising the amino acid sequence denoted by SEQ ID NO. 75 and a light chain variable region comprising the amino acid sequence denoted by SEQ ID NO. 85.

In further embodiments the isolated monoclonal antibody according to the invention is the antibody also referred to herein as "MH49", namely an antibody comprising a heavy chain variable region comprising the amino acid sequence denoted by SEQ ID NO. 76 and a light chain variable region comprising the amino acid sequence denoted by SEQ ID NO. 86.

In still further embodiments the isolated monoclonal antibody according to the invention is the antibody also referred to herein as "MH67", namely an antibody comprising a heavy chain variable region comprising the amino acid sequence denoted by SEQ ID NO. 77 and a light chain variable region comprising the amino acid sequence denoted by SEQ ID NO. 87.

In yet further embodiments the isolated monoclonal antibody according to the invention is the antibody also referred to herein as "MH74", namely an antibody comprising a heavy chain variable region comprising the amino acid sequence denoted by SEQ ID NO. 79 and a light chain variable region comprising the amino acid sequence denoted by SEQ ID NO. 89.

As indicated above, five antibodies, namely the antibodies referred to herein as MH2, MH73, MH75, MH76 and MH77 were shown to bind the RTB subunit.

As used herein, the term "ricin B chain" refers to the B chain of ricin (RTB), which is a galactose specific lectin. RTB is approximately 33 kDa.

In some embodiments RTB may be prepared for example by extracting the toxin from seeds of *R. communis*, and subjecting the extract to reducing conditions and to further separation steps, thereby separating the A chain from the B chain, for example as shown below.

Therefore in some embodiments the isolated monoclonal antibody according to the invention binds to ricin B chain.

In specific embodiments the isolated monoclonal antibody according to the invention comprises a heavy chain variable region comprising the amino acid sequence denoted by SEQ ID NO. 74, SEQ ID NO. 78, SEQ ID NO. 80, SEQ ID NO. 81, or SEQ ID NO. 82 and a light chain variable region denoted by SEQ ID NO. 84, SEQ ID NO. 88, SEQ ID NO. 90, SEQ ID NO. 91, or SEQ ID NO. 92.

In further embodiments the isolated monoclonal antibody according to the invention is the antibody also referred to herein as "MH2", namely an antibody comprising a heavy chain variable region comprising the amino acid sequence denoted by SEQ ID NO. 74 and a light chain variable region comprising the amino acid sequence denoted by SEQ ID NO. 84.

In further specific embodiments the isolated monoclonal antibody according to the invention is the antibody also referred to herein as "MH73", namely an antibody comprising a heavy chain variable region comprising the amino acid sequence denoted by SEQ ID NO. 78 and a light chain variable region comprising the amino acid sequence denoted by SEQ ID NO. 88.

In yet further embodiments the isolated monoclonal antibody according to the invention is the antibody also referred to herein as "MH75", namely an antibody comprising a heavy chain variable region comprising the amino acid sequence denoted by SEQ ID NO. 80 and a light chain variable region comprising the amino acid sequence denoted by SEQ ID NO. 90.

In some embodiments the isolated monoclonal antibody according to the invention is the antibody also referred to herein as "MH76", namely an antibody comprising a heavy chain variable region comprising the amino acid sequence denoted by SEQ ID NO. 81 and a light chain variable region comprising the amino acid sequence denoted by SEQ ID NO. 91.

In yet further embodiments the isolated monoclonal antibody according to the invention is the antibody also referred to herein as "MH77", namely an antibody comprising a heavy chain variable region comprising the amino acid sequence denoted by SEQ ID NO. 82 and a light chain variable region comprising the amino acid sequence denoted by SEQ ID NO. 92.

The isolated monoclonal antibody according to the invention may be a chimeric, a humanized or a human antibody.

As described in the appended Examples, chimeric macaque-human antibodies were raised against the ricin toxin, in which portions of the heavy and light chains were derived from rhesus macaque and the remainder of the chain(s) was derived from a human antibody sequence.

The term "chimeric" antibodies as herein defined refers to antibodies in which a portion of the heavy and/or light chain is derived from a particular species, while the remainder of the chain(s) is derived from another species, as well as fragments of such antibodies, which exhibit the same biological activity (namely biding to the ricin toxin). Chimeric antibodies may be prepared by any method known in the art, for example as described below.

Therefore in some embodiments the isolated monoclonal antibody according to the invention is a chimeric antibody.

It is appreciated that "humanized" forms of non-human (for example, murine) antibodies are antibodies that contain a human-derived immunoglobulin framework with minimal sequences derived from non-human immunoglobulin at the CDRs and optionally at additional relevant positions. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and activity.

The term "human antibody" as used herein refers to an antibody that possesses an amino acid sequence corresponding to that of an antibody produced by a human and/or has been made using any of the techniques for making human antibodies disclosed herein. This definition specifically excludes a humanized antibody that comprises non-human antigen-binding residues.

Preparation of humanized and human antibodies is well known in the art.

The present invention further encompasses any antigen-binding fragments of the isolated monoclonal antibody of the invention. Such antigen-binding fragments may be for example Fab and $F(ab')_2$, which are capable of binding antigen. Such fragments may be produced by any method known in the art, for example by proteolytic cleavage, using enzymes such as papain (to produce Fab fragments) or pepsin (to produce $F(ab')_2$ fragments).

Therefore in some embodiments the isolated monoclonal antibody according to the invention is wherein said antibody is an antibody fragment selected from the group consisting of Fv, single chain Fv (scFv), heavy chain variable region, light chain variable region, Fab, $F(ab)_2'$ and any combination thereof.

As exemplified below, the chimeric antibodies prepared in accordance with the present disclosure were shown to neutralize the ricin toxin using an in vitro neutralization assay in Hela Ub-FL cells. The amount of antibody required to neutralize 50% of the toxin is shown in Table 5 below.

Thus in some embodiments the isolated monoclonal antibody according to the invention is wherein said antibody is a neutralizing antibody.

The term "Neutralizing antibody" (or Nab) as herein defined refers to an antibody which defends a cell from an antigen or infectious body by inhibiting or neutralizing the biological effect of the antigen or infectious body. Neutralizing antibodies are mainly defined by their in vitro activity, which in the present case may be assessed for example by the antibody amount that is required to neutralize 50% of the ricin toxin. As used herein the term "highly neutralizing anti ricin antibody" refers to an antibody that is capable of neutralizing the toxin and protecting between about 95% and 100% of animals exposed to ricin toxin in an in vivo protection model, when the antibody is given post-exposure, for example, six hours post exposure.

In another one of its aspects the present invention provides a bispecific molecule comprising the antibody as herein defined.

By the term "bispecific molecule" as herein defined it is meant a molecule comprising a first entity being an antibody or any antigen binding fragment thereof as herein defined and a second entity. The second entity may be a second antibody or antigen binding fragment thereof that specifically binds to a different target, such as but not limited to an epitope in ricin toxin that is different from the epitope recognized by the antibodies in accordance with the invention. The second antibody or antigen binding fragment thereof may also target other toxins, any other protein of a pathogen, a host-related protein, or a host cell, as non-limiting examples. Bispecific antibodies include cross-linked or "heteroconjugate" antibodies and can be made using any convenient cross-linking or recombinant methods.

In yet another one of its aspects the present invention provides an isolated nucleic acid molecule comprising a nucleotide sequence encoding an antibody or any antigen-binding fragment thereof as herein defined.

The term "nucleic acid" or "nucleic acid molecule" as herein defined refers to polymer of nucleotides, which may be either single- or double-stranded, which is a polynucleotide such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA-dependent DNA polymerase).

In still another one of its aspects the present invention provides an expression vector comprising the isolated nucleic acid molecule as herein defined.

The term "Expression vector" sometimes referred to as "expression vehicle" or "expression construct", as used herein, encompass vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. The expression vector in accordance with the invention may be competent with expression in bacterial, yeast, or mammalian host cells, to name but few.

The present invention further provides a host cell transfected with the isolated nucleic acid molecule or with the expression vector as herein defined.

The term "host cells" as used herein refers to cells which are susceptible to the introduction of the isolated nucleic acid molecule according to the invention or with the expression vector according to the invention. Preferably, said cells are mammalian cells, for example CHO cells or HEK 293 (which were used in the present disclosure). Transfection of the isolated nucleic acid molecule or the expression vector according to the invention to the host cell may be performed by any method known in the art.

In yet another one of its aspects the present invention provides an immunoconjugate comprising the antibody or any antigen-binding fragment thereof as herein defined and an additional anti-ricin agent.

The term "immunoconjugate" as herein defined refers to an antibody or any antigen-binding fragment thereof according to the invention that is conjugated (linked or joined) to an additional agent Immunoconjugates may be prepared by any method known to a person skilled in the art, for example, by cross-linking the additional agent to the antibody according to the invention or by recombinant DNA methods.

The term "additional anti-ricin agent" as herein defined refers to any agent known in the art for the treatment of ricin poisoning. In some embodiments the additional anti-ricin agent in accordance with the invention is a sugar analogue (that prevents ricin binding to its target), an inhibitor of the catalytic subunit of ricin toxin (for example azidothymidine) and an additional antibody.

The term "additional antibody" as herein defined refers to an antibody, which is not the antibody according to the invention, which may be used in combination with any one of the antibodies of the invention. Such antibody may be directed against ricin, against a different antigen or toxin of *Ricinus communis*, against a different pathogen or against a host-related moiety.

The present invention further provides a pharmaceutical composition comprising as an active ingredient the isolated monoclonal antibody or any antigen-binding fragment thereof as herein defined, the bispecific molecule or the immunoconjugate according to the invention and a pharmaceutically acceptable carrier, excipient or diluent.

The "pharmaceutical composition" of the invention generally comprises the antibody or any antigen-binding fragment thereof as herein defined and a buffering agent, an agent which adjusts the osmolarity of the composition and optionally, one or more pharmaceutically acceptable carriers, excipients and/or diluents as known in the art. Supplementary active ingredients can also be incorporated into the compositions, e.g. antibiotics.

As used herein the term "pharmaceutically acceptable carrier, excipient or diluent" includes any and all solvents, dispersion media, coatings, antibacterial and antifungal agents and the like, as known in the art. The carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be both pharmaceutically and physiologically acceptable in the sense of being compatible with the other ingredients and not injurious to the subject. Except as any conventional media or agent is incompatible with the active ingredient, its use in the therapeutic composition is contemplated.

In some embodiments the pharmaceutical composition as herein defined further comprises an adjuvant.

An "adjuvant" as herein defined refers to a pharmacological and/or immunological agent that modifies the effect of other agents. Adjuvants are inorganic or organic chemicals, macromolecules or entire cells of certain killed bacteria, which enhance the immune response to an antigen. Examples of adjuvants include, but are not limited to Freund's adjuvant, aluminium hydroxide etc.

In some further embodiments the pharmaceutical composition according to the invention further comprises an additional anti-ricin agent.

In yet another one of its aspects, the present invention provides the isolated monoclonal antibody or any antigen-binding fragment thereof according to the invention, the bispecific molecule, the immunoconjugate or the pharmaceutical composition as herein defined for use in a method of prophylaxis, treatment or amelioration of ricin toxin poisoning.

Further provided is a method of prophylaxis, treatment or amelioration of ricin toxin poisoning comprising administering to a subject in need thereof a therapeutically effective amount of the isolated monoclonal antibody or any antigen-binding fragment thereof according to the invention, the bispecific molecule, the immunoconjugate or the pharmaceutical composition as herein defined.

By the term "prophylaxis" as herein defined it is meant to provide a preventive or prophylactic treatment, namely acting in a protective manner, to defend against or prevent ricin poisoning, namely before exposure to ricin toxin.

The terms "treatment", "treating", "treat" or forms thereof as used herein, mean preventing, ameliorating or delaying the onset of one or more clinical indications of poisoning or disease activity resulting from exposure to ricin toxin in a subject at risk of being poisoned by or exposed to ricin toxin or in a subject that was exposed to ricin toxin.

Administration according to the present invention may be performed by any of the following routes: oral administration, intravenous, intramuscular, intraperitoneal, intratechal or subcutaneous injection; intrarectal administration; intranasal administration, ocular administration or topical administration.

In specific embodiments administration according to the present invention may be performed intravenously.

In some embodiments the method according to the invention is further comprises administering to a subject in need thereof an additional anti-ricin agent.

The term "subject in need thereof" as herein defined means warm-blooded animals, such as for example rats, mice, dogs, cats, guinea pigs, primates and humans at risk of being exposed to ricin toxin or anyone who has come in contact with ricin toxin, for example mail handlers, military personnel, laboratory workers and people who may be exposed to ricin toxin during a bio-terror event.

The method according to the invention may be applied where the isolated monoclonal antibody or any antigen-binding fragment thereof, bispecific molecule, immunoconjugate or pharmaceutical composition as herein defined is administered to the subject prior to or after exposure to ricin toxin.

In some embodiments the isolated monoclonal antibody or any antigen-binding fragment thereof, bispecific molecule, immunoconjugate or pharmaceutical composition as herein defined is administered to the subject immediately after exposure to ricin toxin or between about 1 to about 72 hours after exposure to ricin toxin.

As used herein the term "immediately" encompasses the instant time frame following detection of ricin poisoning, e.g. minutes after detection.

By way of a non limiting example, the isolated monoclonal antibody or any antigen-binding fragment thereof, bispecific molecule, immunoconjugate or pharmaceutical composition as herein defined is administered to the subject about 1, 6, 12, 18, 24, 30, 36, 42, 48, 54, 60, 66 or about 72 hours after exposure to ricin toxin.

The term "therapeutically effective amount" for purposes herein defined is determined by such considerations as are known in the art in order to cure, arrest or at least alleviate or ameliorate the medical conditions associated with ricin poisoning. For any preparation used in the methods of the invention, the dosage or the therapeutically effective amount can be estimated initially from in vitro cell culture assays or based on animal models known in the art.

In the above and other embodiments the isolated monoclonal antibody or any antigen-binding fragment thereof is administered at a therapeutically effective amount. The treating physician would be able to determine the appropriate therapeutic dosage depending on various clinical parameters of the patient as is well known in the art. A therapeutically effective amount of the antibody is for example between about 10 μg/kg to about 50 mg/kg. Non-limiting examples of dosage forms include 1 mg/kg, 2 mg/kg, 3 mg/kg, 3.3 mg/kg, 5 mg/kg, 10 mg/kg, 20 mg/kg, 30 mg/kg, 40 mg/kg and 50 mg/kg.

It should be appreciated that the therapeutically effective amount as herein defined refers to the isolated monoclonal antibody or any antigen-binding fragment per se, as the active ingredient of a pharmaceutical composition, or as a component of a bispecific molecule or an immunoconjugate.

In some further embodiments the isolated monoclonal antibody or any antigen-binding fragment thereof, bispecific molecule, immunoconjugate or pharmaceutical composition as herein defined is administered to the subject as a single dose or as multiple doses.

As demonstrated in the appended examples, the antibodies described herein, in particular the antibodies referred to as MH75, MH1, MH77, MH73, MH2, MH76, MH49, MH36, MH67 and MH74 were shown to neutralize the ricin toxin in an in vitro assay, by measuring the translation capacity of a cell that was exposed to ricin toxin.

Specifically, using mice in vivo protection model the antibodies designated MH73, MH36, MH75, MH1 and MH77 yielded extremely high survival rates of 83%, 95%, 96%, 100% and 100%, respectively.

Thus in still another one of its aspects the present invention provides a method of neutralizing ricin poisoning comprising administering to a subject in need thereof a therapeutically effective amount of the isolated monoclonal antibody or any antigen-binding fragment thereof, the bispecific molecule, the immunoconjugate or the pharmaceutical composition as herein defined.

By the term "neutralizing" it is meant blocking, preventing or at least reducing the biological activity of ricin toxin, namely blocking, preventing or at least reducing its ability to inactivate the 28S ribosomal subunit.

The ability of the antibody to neutralize the toxicity of ricin toxin may be monitored by any method known in the art, in particular, using the neutralization assay described herein below or using a viability assay, for example by following the survival of cells that were exposed to ricin toxin and incubated in the presence of the antibody as herein defined, or using a standard animal model, for example as shown in the examples.

The present invention further provides a method of detecting ricin toxin in a biological sample obtained from a subject, said method comprising:

(a) contacting said biological sample with the isolated monoclonal antibody or any antigen-binding fragment thereof according to the invention, wherein said monoclonal antibody is labeled with a detectable marker; and (b) detecting said isolated monoclonal antibody or any antigen-binding fragment thereof;

wherein the presence of said isolated monoclonal antibody or any antigen-binding fragment thereof indicates the presence of ricin toxin in said biological sample.

Detecting the isolated monoclonal antibody may be performed by any method known to a person skilled in the art based on the detectable marker present on the antibody.

The term "detectable marker" refers to any atom, molecule or a portion thereof, the presence, absence or level of which is directly or indirectly monitorable. Labeling of the antibodies as herein defined may be performed by any method known in the art.

The term "biological sample" as herein defined encompasses fluids, solids and tissues obtained from the subject. The term biological sample also refers to forensic samples.

In another one of its aspects the present invention provides a kit for detecting ricin toxin comprising:

(a) at least one labeled isolated monoclonal antibody or any antigen-binding fragment thereof according to the invention;

(b) means for detection of said labeled isolated monoclonal antibody; and optionally (c) instructions for use of said kit.

It is appreciated that the term "purified" or "isolated" refers to molecules, such as amino acid or nucleic acid sequences, peptides, polypeptides or antibodies that are removed from their natural environment, isolated or separated. An "isolated antibody" is therefore a purified antibody. As used herein, the term "purified" or "to purify" also refers to the removal of contaminants from a sample.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

EXAMPLES

Without further elaboration, it is believed that one skilled in the art can, using the preceding description, utilize the present disclosure to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook & Russell, 2001.

Standard medicinal chemistry methods known in the art not specifically described herein are generally followed essentially in the series "Comprehensive Medicinal Chemistry" by various authors and editors, published by Pergamon Press.

Experimental Procedures

Immunization

Crude ricin was prepared from seeds of endemic *Ricinus communis* (*R. communis*) that were homogenized in a Waring blender in 5% acetic acid/phosphate buffer ($Na_2HPO_4$, pH 7.4). The homogenate was centrifuged and the clarified supernatant containing the toxin was subjected to ammonium sulphate precipitation (60% saturation). The precipitate was dissolved in PBS and dialyzed extensively against the same buffer. The crude ricin preparation was loaded onto a gel-filtration column (Superdex 200HR 16/60 Hiload) and washed out with PBS to yield two well-separated protein peaks corresponding to RCA (*Ricinus communis* agglutinin, another toxic protein found in the castor bean) and ricin. Ricin was further reduced in the presence of DTT in pH 9.0 followed by the addition of Iodoacetamide (IAA, added in order to block cysteines and prevent disulfide bond formation) and dialysis in PBS.

Two rhesus macaques (*Macaca Mulata*) were used for eliciting antibodies against ricin. The first rhesus macaque was injected with 100 μg of reduced ricin, prepared as described above, mixed with complete Freund's adjuvant followed by two monthly booster injections of 100 μg reduced ricin mixed with incomplete Freund's adjuvant. The second rhesus macaque was injected with 2 μg of purified ricin mixed with complete Freund's adjuvant followed by three monthly booster injections of 5, 80 and 80 μg purified ricin mixed with incomplete Freud adjuvant. Seven days after the last boost, the monkeys were sacrificed and samples were taken from their blood and lymphatic nodes in order to isolate mRNA that was subsequently used for variable heavy and variable light (VH/VL) chain amplification.

Phage Library Construction mRNA was extracted from lymph nodes and peripheral blood of the immunized Macaques, and was reverse-transcribed into cDNA. The heavy and light chains variable regions (VH and VL, respectively) were amplified from the cDNA, using a set of primers designed to cover all known antibody families of Monkeys. The nucleic acid sequences of these primers (synthesized by Integrated DNA Technologies, IDT) are detailed in Table 1 below (SEQ ID NO. 1 to SEQ ID NO. 52). VH and VL were randomly assembled by PCR to construct a combinatorial single-chain (scFv) library, which was then cloned into phagmid vector to create a phage-display library.

TABLE 1

Primers designed for the amplification of antibodies variable regions

| SEQ ID NO. | Primer | Sequence |
|---|---|---|
| 1 | Lib-H1 F | CAGGAGCAGCTGGTGCAGTC |
| 2 | Lib-H2 F | CAGGTCCAGCTGGTGSAGWC |

TABLE 1-continued

Primers designed for the amplification of antibodies variable regions

| SEQ ID NO. | Primer | Sequence |
|---|---|---|
| 3 | Lib-H3 F | CAGGTSCAGCTCGAGSAGTC |
| 4 | Lib-H4 F | CAGGTGCAGCTGCAGGAGTC |
| 5 | Lib-H5 F | CAGCTGCAGCTGCAGSAGTC |
| 6 | Lib-H6 F | CAGGTGCAGCTRCTCGAGTS |
| 7 | Lib-H7 F | CAGGTSCAGCTGGTGCAGTY |
| 8 | Lib-H8 F | CAGGTSACCTTGAAGGAGTC |
| 9 | Lib-H9 F | CAGGTCCAGCTGCAGGAAAG |
| 10 | Lib-H10 F | GAGGTGCAGYTGGTGGAGWC |
| 11 | Lib-H11 F | GAGGTTCAGYTGGTKGAATC |
| 12 | Lib-H12 F | GAGGTGCAGCTGGTGSARTC |
| 13 | Lib-H13 F | GAGGTGCAGCTGGYRGAGTC |
| 14 | Lib-H14 F | GAAGTGCAGYTGGTGGAGTC |
| 15 | Lib-H15 F | GAGGTGCAGCTCGAGGAGTC |
| 16 | Lib-H16 F | GAGGTGCAGCTGCTCGAGTC |
| 17 | VH Rev1 | CTGARGAGRCTGTGACC |
| 18 | VH Rev2 | CTGAGGACACGGCAACC |
| 19 | Lib-K1 F | GATATTGTGATGAYCCAGAC |
| 20 | Lib-K2 F | GATACTGTGATGACCCAGAC |
| 21 | Lib-K3 F | GATATYGAGCTCACBCAGTC |
| 22 | Lib-K4 F | GATGTTGYRATGACTCAGTC |
| 23 | Lib-K5 F | GACATTCAGMTGWCCCAGTC |
| 24 | Lib-K6 F | GACGTTCAGATGACCCAGTC |
| 25 | Lib-K7 F | GACATCCAGATGACCCAGTC |
| 26 | Lib-K8 F | GAGCTCCWGATGACMCAGTC |
| 27 | Lib-K9 F | GAAATWGTRATGACGCAGTC |
| 28 | Lib-K10 F | GAAATCGAGCTCACRCAGTC |
| 29 | Lib-K11 F | CAAGTTATATTGACTCAGTC |
| 30 | Lib-K12 F | GACATCGAGCTCACCCAGTC |
| 31 | Lib-K13 F | GAGCTCGTGTTGACACAGTC |
| 32 | Lib-K1 Rev | YTTGAKATCCAGTTTGGTCCCGGG |
| 33 | Lib-K2 Rev | TTTGAYCTCCACCYTGGTCCCTCC |
| 34 | Lib-K3 Rev | TTTGATSTCCACTTTGGTCCCCTG |
| 35 | Lib-K4 Rev | TYTGATTTCCACCYTGGTCCCTTG |
| 36 | Lib-K5 Rev | CTTGATGTCCACCTTGGTCCCGTG |
| 37 | Lib-K6 Rev | TTTTAGTACCACCTTGGTCCCTTG |
| 38 | Lib-L1 F | CAGCCAGKGCTGACTCAGCC |
| 39 | Lib-L2 F | CAGCCTGKGCTGACTCAGYC |

TABLE 1-continued

Primers designed for the amplification of antibodies variable regions

| SEQ ID NO. | Primer | Sequence |
|---|---|---|
| 40 | Lib-L3 F | CAGTCTGTGYTGACKCAGCC |
| 41 | Lib-L4 F | CAGTCTGCCCTGACTCAGCC |
| 42 | Lib-L5 F | CAGTCTGCCCCGAYTCAGYC |
| 43 | Lib-L6 F | CAGGCTGCCCYGACTCAGYC |
| 44 | Lib-L7 F | CAGGCAGGGCTGACTCAGCC |
| 45 | Lib-L8 F | CAGACTGTGGTGACCCAGGA |
| 46 | Lib-L9 F | AAGCCTATGCTGACTCAGCC |
| 47 | Lib-L10 F | TCTTCTGRGCTGACTCAGGA |
| 48 | Lib-L11 F | TCCTATGAGCTGACWCAGCC |
| 49 | Lib-L12 F | CAGSCTGTGCTGACTCAGCC |
| 50 | Lib-L13 F | CWGCCTGTGCTGACTCARYC |
| 51 | Lib-L1 Rev | TAGRACGGTSAGCCGGGTC |
| 52 | Lib-L2 Rev | GAGGAYGGTCAAYTTGGTG |

Phage Particle Amplification

The *E. coli* TG1 strain (Lucigen #60502) was infected with the desired phages, in the presence of a helper phage, M13K07 (NEB #NO315S). The infected culture was centrifuged and the pellet was eluted with 2YT medium containing Ampicilin (100 μg/ml) and Kanamicin (50 μg/ml), and incubated over-night (o.n.) in 30° C. Following a further centrifugation step, the supernatant was passed over 0.45 μm filter and the phage particles were incubated in the presence of 2.5M NaCl, 20% PEG 6000 for 2 hours on ice. After an additional centrifugation step of 1 hr at 9000 g, the pellet containing the phage particles was eluted with PBS and stored at 4° C.

Panning

The process of selecting antibodies against a specific antigen from a phage display library is called “panning”. In one cycle of panning, the library is incubated with the antigen, to allow binding. The unbound phages are then eliminated by washing, while those phages displaying scFv that is bound to the antigen are eluted and enriched. The eluted and enriched phages obtained in the first panning cycle may be subjected to additional panning cycles for screening of specific clones. Several consecutive panning cycles usually allow the selection of high affinity antibodies.

Biotinylated ricin, namely pure ricin that was biotinylated using a commercial kit (EZ-Link sulfo-NHS-biotin, pierce) was first incubated with Streptavidin (SA) beads (Dynabeads M-280, Invitrogen #11206D) for 30 minutes (min). The phage display library was added to the beads and the mixture was incubated for an additional 90 min The beads were then washed with 3% bovine serum albumin (BSA) in phosphate buffered saline (PBS), followed by washing with phosphate buffered saline Tween-20 (PBST) and PBS. The bound phages were eluted from the beads by incubation in 100 mM Triethylamine for 30 min, followed by neutralization with 200 μl Tris-HCl pH 7.5 (1M). The resulting phages were used to infect TG1 cells and grown over night for phage enrichment. The culture was then collected and 100 μl were used for phage rescue, to prepare the input for the next round of panning. In total, three rounds of selection were used for isolating the anti-ricin antibodies.

Screening

Individual clones were obtained by performing three rounds of selection (three panning cycles) as described above and grown in 96-well plates. Each clone was then tested for its ability to specifically bind ricin, and each of its subunits, namely ricin chain A and ricin chain B in an ELISA assay as described below. Maxisorp 96-well microtiter plates were coated overnight with 5 μg/ml of ricin (50 μl/well) in $NaHCO_3$ buffer (50 mM, pH 9.6), then washed and blocked with PBST buffer (0.05% Tween 20, 2% BSA in PBS) at room temperature for one hour. Clone samples were added to the ricin-coated plates for an incubation of one hour, the plates were then washed with PB ST, incubated with the detecting horseradish peroxidase (HRP)-conjugated anti-M13 antibody and then developed using Tetramethylbenzidine (TMB/E). Single-stranded DNA of phage clones was prepared using Big Dye (Applied Biosystems) and the PCR products were analyzed with ABI PRISM 310 Genetic Analyzer (Applied Biosystems).

Producing Full Length antibodies

Each single chain variable fragment (scFv) isolated from the phage display library was cloned into a mammalian full-length Immunoglobulin expression vector, providing each chain with the corresponding signal-peptide and constant gene, and resulting in IgG1/κ/λ chimeric macaque-human antibody expression.

Antibody Sequencing

The plasmids encoding the chimeric antibodies were sequenced using ABI PRISM 310 Genetic Analyzer (Applied Biosystems). The plasmids were transiently transfected to HEK293 cells, and antibodies were purified from the culture media using Protein A columns In Vitro Neutralization Assay Hela Ub-FL cells (7) were cultured in Dulbecco's modified Eagle's medium (DMEM, Biological Industrial, Beit Haemek, Israel) supplemented with 10% fetal calf serum (FCS). For cytotoxicity studies (i.e. the neutralization assays), cells were seeded in 96-well plates ($1\times10^5$ cells/well) in medium containing ricin (at 2 ng/ml, prepared as described above) and incubated at 37° C. in the presence or absence of the anti-ricin antibodies prepared as discussed above. Sixteen hours later the medium was removed, and the cells were subjected to a protein translation assay, in order to determine the neutralizing effect of the antibody. Briefly, the cells were lysed and the residual intracellular ubiquitin-luciferase fusion protein activity was determined using D-luciferin as a substrate (measured in luminometer; Victor3, PerkinElmer) and expressed as percent activity determined for untreated cells.

In Vivo Protection Assay

Female out bred ICR mice (Charles River Laboratories) were maintained at 20-22° C. and a relative humidity of 50±10% on a 12-h light/dark cycle, fed with commercial rodent chow (Koffolk Inc.) and provided with tap water ad libitum. Treatment of animals was in accordance with regulations outlined in the USDA Animal Welfare Act and the conditions specified in Guide for Care and Use of Laboratory Animals (National Institute of Health, 1996) Animal studies were approved by the local ethical committee on animal experiments.

Mice, 27-32 gr, were intranasaly intoxicated with $2LD_{50}$ of ricin (5 μg/Kg, 50 μl/mice) and six hours later were treated with 100 μg of anti-ricin antibody which was injected intravenously. The mice were monitored for 14 days and the protection conferred by each antibody was calculated as percent of surviving mice. Mice intoxicated with ricin without antibody treatment, were used as control.

Example 1

Preparation of Chimeric Antibodies Directed to Ricin

Rhesus macaques were immunized against ricin and mRNA was extracted from the immunized macaques and reverse-transcribed into cDNA, as described above. The cDNA was further used for construction of a phage-display library and individual phage clones were selected as described above.

After panning and screening of the phage display library, 10 different antibodies, termed MH1, MH2, MH36, MH49, MH67, MH73, MH74, MH75, MH76 and MH77, were isolated and sequenced, as described above. The nucleic acid sequences of the heavy and the light chains of the antibodies are shown in Table 2 below. A sequence alignment of the nucleic acid sequences of the above isolated antibodies is shown in FIG. 1 for the heavy chain sequences and in FIG. 2 for the light chain sequences of the above antibodies.

TABLE 2

Nucleic acid sequences of the antibodies heavy and light chains

| SEQ ID NO. | Sequence | Description |
|---|---|---|
| 53 | GAGGCGCAGCTCGAGGAGTCGGGCCCAGGACTGGTGAAGCCTTCGGAGACC CTGTCCCTCAGTTGCGCTGTCTCTGGTGGCTCCTTCAGGAGTTACTGGTGG GGCTGGATCCGCCAGCCCCCAGGGAAGGGCCTGGAGTGGATTGGGAGTATC TATGGCAGTAGTGGGAGCACCGAATACAACCCCTCCCTCAAAAGTCGAGCC ACCATTTCAAGAGACACGTCCAAGAACCAGTTCTCCCTGAAGCTGAGCTCT GTGACCGCCGCGGACACGGCCGTCTATTACTGTGCGAGGCAGATACAATTT TTGACTGATGCTTTTGATTTCTGGGGCCAAGGGCTCAGGGTCACAGTCTCC TCA | Heavy chain of MH49 |
| 54 | CAGGTGCAGCTCGAGCAGTCGGGCCCAGGACTGGTGAAGCCTTCGGAGACC CTGTCCCTCAGTTGCGCTGTCTCTGGTGGCTCCTTCAGGAGTTACTGGTGG GGCTGGATCCGCCAGCCCCCAGGGAAGGGCCTGGAGTGGATTGGGAGTATC TATGGCAGTAGTGGGAGCACCGAATACAACCCCTCCCTCAAAAGTCGAGCC ACCATTTCAAGAGACACGTCCAAGAACCAGTTCTCCCTGAAGCTGAGCTCT GTGACCGCCGCGGACACGGCCGTCTATTACTGTGCGAGGCAGATACAATTT TTGACTGATGCTTTTGATTTCTGGGGCCAAGGGCTCAGGGTCACAGCCTCC TCA | Heavy chain of MH67 |

TABLE 2-continued

Nucleic acid sequences of the antibodies heavy and light chains

| SEQ ID NO. | Sequence | Description |
|---|---|---|
| 55 | CAGGTGCAGCTGCAGGAGTCGGGCCCAGGACTGGTGAAGCCTTCGGAGACC CTGTCCCTCACCTGCGCTGTCTCTGGTGGCTCCCTCAGCAGTAACTACTGG AGCTGGATCCGCCAGGCCCCAGGGAAGGGACTGGAGTGGATTGGACATATC TTTGGTGGTGGTGGGGGCACCGACTACAACCCCTCCCTCAAGAGTCGAGTC ACCATTTCAACAGACACGTCCAAGAACCAGTTCTCCCTGAAGCTGAGCTCT CTGGCCGCCGCGGACACGGCCGTGTATTACTGTGCGAGAGCTGCAATAATG TACCCCAACCGGTTCGATGTCTGGGGCCCGGGAGTCCTGGTCACAGCCTCT AGC | Heavy chain of MH73 |
| 56 | GAGGTGCAGCTGGTGCAATCTGGAGCAGAGGTGAAAAGGCCCGGGGAGTCA CTGAAGATCTCCTGTAAGACTTCTGGATACAGCTTTACCAGCTACTGGATC AGCTGGGTGCGCCAGATGCCCGGGAAAGGCCTGGAGTGGATGGGGGCGATT GATCCTACTGATTCTGATACCAGATACAACCCGTCCTTCCAAGGCCAGGTC ACCATCTCCGCCGACAAGTCCATCAGCACCGCCTACCTGCAGTGGAGCAGG CTGAAGGCCTCGGACACCGCCACGTATTACTGTGCGAAATCAGACTGGAGT GATTATTATGGCAACTCATTGGATGTCTGGGGCCGGGGAGTTCTGGTCACA GCCTCTTCA | Heavy chain of MH74 |
| 57 | CAGGAGCAGCTGGTGCAGTCTGGGGGCGGCTTGGCAAAGCCTGGGGGGTCC CTGAGACTCTCCTGCGCAGACTCCGGATTCACCTTCAGTGACCACTACATG GACTGGGTCCGCCAGGCTCCAGGGAAGGGGCTGGAGTGGGTCTCACGTATT AGTACTGGTGGTGGAACCACATGGTACGCAGACTCCGTGAAGGGCAGATTC ACCATCTCCAGAGAGAACGCCAACAACACACTGTATCTTCAAATGAACAGC CTGAGAGGTGAGGACACGGCTGTCTATTACTGTGCGAAAGTTCCCACGGGA TACAGTCAAGGGGTCTGGGGGCCGGGAGTCCTGGTCACAGCCTCCTCA | Heavy chain of MH75 |
| 58 | CAGGTGCAGCTGCAGGAGTCTGGGGGCGGCTTGGCAAAGCCTGGGGGGTCC CTGAGACTCTCCTGCGCAGCCTCCGGATTCACCTTCAGTGACTACTACATG GACTGGGTCCGCCAGGCTCCAGGGAAGGGGCTGGATTGGGTCTCACGCATT AGTAATGGTGGTGGTACCACATGGTACGCAGACTCCGTGAAGGGCAGATTC ACCATCTCCAGAGAGAACGCCAAGAACACACTGTATCTTCAAATGAACAGC CTGAGACCTGAGGACACGGCTGTCTATTACTGTGCGACGGTGCCCACAGCG ACATCTGGAATAGGCAACTGGGGCCAGGGAGTCCTGGTCACAGCCTCCTCA | Heavy chain of MH76 |
| 59 | CAGGTGCAGCTGCTCGAGTCGGGCCCAGGACTGGTGAAGCCTTCAGAGACC CTGTCCCTCACCTGCACTGTCTCTGGTGGCTCTTTCAGTAGTAGTCATTGG TGGAACTGGATCCGCCAGGCCCCAGGGAAAGGGCTGGAGTGGATTGGCTAT ATCACCACTAGTAATGGTGCCACCTACTACAACCCCTCCCTCAAGAGTCGA GTCACCATTTCAACAGACACGTCCAAGAACCAGTTCTCCCTGAAACTGAGC TCTGTGACCGCCGCGGACTCGGCCGTGTATTTCTGTGCGAGGGGATACAGT AACTGGGACAACTGGTTCGATGTCTGGGGCCCGGGAGTCCTGGTCACAGTC TCCTCA | Heavy chain of MH77 |
| 60 | CAGCTGCAGCTGCAGGAGTCGGGCCCAGGACTGGTGAAGCCTTCAGAGACC CTGTCCCTCACTTGCGCTGTCTCTGGTGGCTCCATCAGCGGTGGTTATGGC TGGGGCTGGATCCGCCAGCCCCCAGGGAAGGGGCTGGAGTGGGTTGGGAGT ATCTATGGTAGTACTGGGAACACCTACTACAACCCCTCCCTCAAGAGTCGA GTCACCATTTCAACAGACACGTCCAAGAACCAGCTCTCCCTGAAGGTGAGC TCTGTGACCGCCGCGGACACGGCCATCTACTACTGTGCGAGAGCCCGCAGT GGTACTTTGTGGTTCCTCGAGTTCTGGGGCCAGGGCGCCCCGGTCACAGCA TCCTCA | Heavy chain of MH1 |
| 61 | GAGGTTCAGTTGGTGGAATCTGGGGGCGGCTTGGCAAAGCCTGGGGGGTCC CTGAGACTCTCCTGCGCAGCCTCCGGATTCACCTTCAGTGACTACTACATG GACTGGGTCCGCCAGGCTCCAGGGAAGGGGCTGGAGTGGGTCTCACGTATT AGTAATGGTGGTGGTAGTAAATGGTACGCAGACTCCGTGAAGGGCAGATTC ACCATCTCCAGAGAGAACGCCAAGAACACACTGTATCTTCAAATGAACAGC CTGAGAGCTGAGGACACGGCTGTATATTACTGTGCGGAAGTTCCCACGGGA TACAGTCAAGGTGTCTGGGGCCCGGGAGTCCTGTTCACAGTCTCCTCA | Heavy chain of MH2 |
| 62 | GAAGTGCAGCTGGTGGAGTCTGGGGGAGGCTTGGTCCAGCCTGGGGGGTCC CTGAGGCTCTCCTGTGCAGCCTCTGGATTCACCTTCAGTAACGTCTGGATG AACTGGGTCCGCCAGACTCCAGGGAAGGGGCTAGAGTGGGTTGCCCGTATT AAAGTCAAAGCTGACGGTGGAACAGCAGATTACGCCGCGTCTGTGAAAGGC AGATTCACCATCTCAAGAGACGATTCAAAGAACACACTGTATCTGCAAATG AACAGTCTGAAAACCGAGGACACGGCCGTGTATTACTGCACCACAGAGGAG ATTACAGTGGCCCGTTATGACTACTGGGGCCAGGGAGTCCTGGTCACAGTC TCCTCA | Heavy chain of MH36 |
| 63 | CAGCCTGTGCTGACTCAGCCACGCTCAGTGTCCGTGTCCCCAGGACAGACG GCCAGGATCACCTGTGGGGGAGACAACATTGGAAGTAAAAGTGTGCAGTGG TACCAGCAGAAGCCACCGCAGGCCCCTGTGCTGGTCATCTATGCTGATAGC GAACGGCCCTCAGGAATCCCTGAGCGATTCTCTGGCTCCAACTCAGGGAAC ACCGCCACCCTGACCGTCAGCGGGGTCGAGGCCGGGGATGAGGCTGACTAT | Light chain of MH1 |

TABLE 2-continued

Nucleic acid sequences of the antibodies heavy and light chains

| SEQ ID NO. | Sequence | Description |
|---|---|---|
| | TACTGTCAGGTGTGGGACAGTAGTAGTGATCATGTGTTATTCGGAGGAGGG ACCCGGCTGACCGTCCTA | |
| 64 | CAGTCTGTGTTGACTCAGCCACAATCGGTGTCGGTGTCCCCAGGACAGACG GCCAGGATCTCCTGTGGGGGAGACAACATTGGAAGTAAAAATGTGCACTGG TACCAGCAGAAGCCACCGCAGGCCCCTGTGCTGGTCATCTATGCTGGAACC GAACGGCCCTCAGGGATCCCTGAGCGATTCTCTGGCTCCAACTCCGGGAAC ACGGCCACCCTGACCATCAGCGGGGTCGAGGCCGGGGATGAGGCGGACTAT TACTGTCAGGTGTGGGACGGTACCCGTGAGCATGTATTATTCGGAGGAGGG ACCCGGCTCACCGTCCTA | Light chain of MH2 |
| 65 | CAGTCTGTGTTGACTCAGCCACCCTCAGCGTCTGGGGCTCCCGGGCAGAGT GTCACCATCTCTTGCTCTGGAAGCAGCTCCAACATCAGAGGTAATGGTGTA CACTGGTACCAGCAGCTCTCAGGAATGGCCCCCAAACTCCTCATCTATAAT AATAATCAGCGACCCTCAGGGGTCCCTGACCGATTCTCTGGCTCCAAGTCT GGCACGTCAGCCTCCCTGGCCATCACTGGTCTCCAGTCTGAGGATGAGGCC GATTATTACTGCGAGGCATGGGATAACAGCCTGAGCGGTGGCTTATTCGGA GGAGGGACCCGGCTGACCGTCCTA | Light chain of MH36 |
| 66 | CAGCCAGGGCTGACTCAGCCTCCCTCAGCGTCTGGGGCTCCCGGGCAGAGT GTCACCATCTCTTGCTCTGGAAGCAGCTCTGACATTGGAAGTCATGACGTC TACTGGTACCAGCAGCTCCCAGGGACGGCCCCCAAGCTCCTCATCTACTAC AGTAATCAGCGACCCTCAGGGGTCCCTGACCGAATCTCTGGCTCCAAGTCT GGCACGTCAGCCTCCCTGACCATCAGCGGTCTCCGGTCCGAGGATGAGGCT GATTATTACTGTGAAACATGGGAAAACAGCCTGAGCGGTCCGGTCTTCGGC GGAGGGACCCGGCTCACCGTCCTA | Light chain of MH49 |
| 67 | GACATTCAGCTGACCCAGTCTCCATCCTCCGTGTCTGCTTCTGTGGGAGAC AGAGTCACCATCACTTGTCGGGCGAGTCAGGCCATCAGTACTTATTTAGCC TGGTATCTACAGAGGCCGGGGAAAGCCCCTGAACTCCTGATCTATTATGCA ACCACTTTACACACTGGGGTCGCTTCAGGTCTCACTGGCAGTGGATCTGGG ACGGATTTCACTCTCACCCTCAGTGCCCTGCAACCTGTAGATGTTGGAACT TACTACTGTCAACAGTTTAAAACTTTACCGTACACTTTTGGCCAGGGGACC AAAGTGGACATCAAA | Light chain of MH67 |
| 68 | GAGCTCCTGATGACACAGTCTCCATCCTCCCTGTCTGCATCTGTAGGAGAC AGAGTCACCATCTCTTGCCGGGCAAGTCAGAACATTTATAGTAATTTAGCG TGGTATCAGCAGAAACCAGGGAAAACTCCTAAGCTCCTGATCTATGCTGCA TCCATCTTGCAGAGTGGGATTCCCTCTCGGTTCAGCGGCAGCGGATCTGGG ACAGATTACACTCTCACCATCACCAACCTGCAGCCTGAAGATTTTGGAACT TATTACTGTCAGCAAGGTTTTGGTATCCCCTACACTTTTGGCCAGGGGACC AAAGTGGAGTTCAAA | Light chain of MH73 |
| 69 | CAGTCTGTGTTGACTCAGCCGCCCTCAGTGTCTGGGGCGCCAGGACAGAGG GTCACCATCTCCTGCACTGGGAGTAATTCCAACATCGGGGCGGGTTATTAT GTGCAGTGGTACCAGCAGCTTCCAGGAACGGCCCCCAAACTCCTCATCTAT GAAAATAATAAGCGACCCTCAGGGGTTTCTGATCGATTCTCTGGCTCCAAG TCTGGTACCTCAGCCTCCCTGACCATCACTGGACTTCAGTCTGAGGATGAG GCTGACTATTACTGCCAGTCCTATGACAGCAGCCTGAGTGTTGTGTTATTC GGAGGAGGGACCCGGCTCACCGTCCTA | Light chain of MH74 |
| 70 | CAGTCTGTGTTGACTCAGCCACAATCGGTGTCGGTGTCCCCAGGACAGACG GCCAGGATCACCTGTGGGGGAGACAACATTGGAAGTAAAAATGTGCACTGG TACCAGCAGAAGCCACCGCAGGCCCCTGTGCTGGTCATCTATGCTGAAACC GAGCGGCCCTCAGGGATCCCTGAGCGATTCTCTGGCTCCAACTCCGGGAAC ACGGCCACCCTGACCATCAGCGGAGTCGAGGCCGGGGATGAGGCGGACTAT TACTGTCAGGTGTGGGACGGTAGCAGTGCACATGTATTATTCGCAGGAGGG ACCCGGCTGACCGTCCTA | Light chain of MH75 |
| 71 | CAGCCAGGGCTGACTCAGCCACACTCGGTGTCGGTGTCCCCAGGACAGACG GCCAGGATCACCTGTGGGGGAGACAACATTGGAAGTAAAAATGTGCACTGG TACCAGCAGAAGCCACCGCAGGCCCCTGTGCTGGTCATCTATGCTGATAGC GAACGGCCCTCAGGGATCCCTGAGCGATTCTCTGGCTCCAACTCCGGGAAC ACGGCCACCCTGACCATCAGCGGGGTCGAGGCCGGGGATGAGGCTGACTAT TACTGTCAGGTGTGGGACAGTAGCAGTAATCATGTGTTATTCGGAGGAGGG ACCCGGCTCACCGTACTA | Light chain of MH76 |
| 72 | GACATTCAGATGTCCCAGTCTCCTTCCTCCCTGTCTGCATCTGTGGGAGAC AAAGTCACCATCACTTGCCAGGCAAGTCAGAGTGTTAGCAGCTGGTTAGCC TGGTATCGGCAGAAACCAGGGAAGGCCCCTAAGCCCCTGATCTATAAGGCA TCCAGTTTGGAAGGTGGGGTCCCCTCAAGGTTCAGCGGCAGTGGATCTGGG | Light chain of MH77 |

TABLE 2-continued

| Nucleic acid sequences of the antibodies heavy and light chains | | |
|---|---|---|
| SEQ ID NO. | Sequence | Description |
| | ACAGATTTCACTCTCACCATCAACAGCCTGCAGCCTGAAGATTTTGCAACT<br>TATTACTGTCAACAGTATAACAGTGTGCCGTACAGTTTTGGCCACGGGACC<br>AAGGTGGACATCAAG | |

The amino acid sequences of the heavy and the light chains of the antibodies MH1, MH2, MH36, MH49, MH67, MH73, MH74, MH75, MH76 and MH77 are shown in Table 3 below. The complementarity determining regions (CDRs) are shown in underline. A sequence alignment of the amino acid sequences of the above isolated antibodies is shown in FIG. 3 for the heavy chain and in FIG. 4 for the light chain of the antibodies.

| SEQ ID NO. | Sequence | Description |
|---|---|---|
| 73 | QLQLQESGPGLVKPSETLSLTCAVSGGSI<br>SGGYGWGWIRQPPGKGLEWVG<br>SIYGSTGNTYYNPSLKSRVTISTDTSKNQLSLKV<br>SSVTAADTAIYYCARARSGTLWFLE<br>FWGQGAPVTASS | Heavy chain of MH1 |
| 74 | EVQLVESGGGLAKPGGSLRLSCAASGFTF<br>SDYYMDWVRQAPGKGLEWVS<br>RISNGGGSKWYADSVKGRFTISRENAKNTLYL<br>QMNSLRAEDTAVYYCAEVPTGYSQG<br>VWGPGVLFTVSS | Heavy chain of MH2 |
| 75 | EVQLVESGGGLVQPGGSLRLSCAASGFTF<br>SNVWMNWVRQTPGKGLEWVA<br>RIKVKADGGTADYAASVKGRFTISRDDSK<br>NTLYLQMNSLKTEDTAVYYCTTEEIT<br>VARYDYWGQGVLVTVSS | Heavy chain of MH36 |
| 76 | EAQLEESGPGLVKPSETLSLSCAVSGGSFR<br>SYWWGWIRQPPGKGLEWIG<br>SIYGSSGSTEYNPSLKSRATISRDTSKNQFSLKLSSVT<br>AADTAVYYCARQIQFLTDAFDFWG<br>QGLRVTVSS | Heavy chain of MH49 |
| 77 | QVQLEQSGPGLVKPSETLSLSCAVSGGSF<br>RSYWWGWIRQPPGKGLEWIG<br>SIYGSSGSTEYNPSLKSRATISRDTSKNQFSLKLSSV<br>TAADTAVYYCARQIQFLTDAFDFWG<br>QGLRVTASS | Heavy chain of MH67 |
| 78 | QVQLQESGPGLVKPSETLSLTCAVSGGSLS<br>SNYWSWIRQAPGKGLEWIG<br>HIFGGGGGTDYNPSLKSRVTISTDTSKNQFSLKLSS<br>LAAADTAVYYCARAAIMYPNRFD<br>VWGPGVLVTASS | Heavy chain of MH73 |
| 79 | EVQLVQSGAEVKRPGESLKISCKTSGYSFTS<br>YWISWVRQMPGKGLEWMG<br>AIDPTDSDTRYNPSFQGQVTISADKSISTAYLQWSR<br>LKASDTATYYCAKSDWSDYYG<br>NSLDVWGRGVLVTASS | Heavy chain of MH74 |
| 80 | QEQLVQSGGGLAKPGGSLRLSCADSGFTF<br>SDHYMDWVRQAPGKGLEWVS<br>RISTGGGTTWYADSVKGRFTISRENANNTLYL<br>QMNSLRGEDTAVYYCAKVPTGYSQG<br>VWGPGVLVTASS | Heavy chain of MH75 |
| 81 | QVQLQESGGGLAKPGGSLRLSCAASGFTF<br>SDYYMDWVRQAPGKGLDWVS<br>RISNGGGTTWYADSVKGRFTISRENAKNTLYL | Heavy chain of MH76 |

-continued

| SEQ ID NO. | Sequence | Description |
|---|---|---|
| | QMNSLRPEDTAVYYCATVPTATSGIG<br>NWGQGVLVTASS | |
| 82 | QVQLLESGPGLVKPSETLSLTCTVSGGSF<br>SSSHWWNWIRQAPGKGLEWIG<br>YITTSNGATYYNPSLKSRVTISTDTSKNQFSLKL<br>SSVTAADSAVYFCARGYSNWDN<br>WFDVWGPGVLVTVSS | Heavy chain of MH77 |
| 83 | QPVLTQPRSVSVSPGQTARITCGGDNI<br>GSKSVQWYQQKPPQAPVLVIYADSERPSG<br>IPERFSGSNSGNTATLTVSGVEAGDEADYYC<br>QVWDSSSDHVLFGGGTRLTVLA | Light chain of MH1 |
| 84 | QSVLTQPQSVSVSPGQTARISCGGDN<br>IGSKNVHWYQQKPPQAPVLVIYAGTERPS<br>GIPERFSGSNSGNTATLTISGVEAGDEADYYC<br>QVWDGTREHVLFGGGTRLTVLA | Light chain of MH2 |
| 85 | QSVLTQPPSASGAPGQSVTISCSGS<br>SSNIRGNGVHWYQQLSGMAPKLLIYNNN<br>QRPSGVPDRFSGSKSGTSASLAITGLQSEDEADYYC<br>EAWDNSLSGGLFGGGTRLTVL<br>A | Light chain of MH36 |
| 86 | QPGLTQPPSASGAPGQSVTISCSGS<br>SSDIGSHDVYWYQQLPGTAPKLLIYYSNQ<br>RPSGVPDRISGSKSGTSASLTISGLRSEDEADYYC<br>ETWENSLSGPVFGGGTRLTVLA | Light chain of MH49 |
| 87 | DIQLTQSPSSVSASVGDRVTITCRASQ<br>AISTYLAWYLQRPGKAPELLIYYATTLHT<br>GVASGLTGSGSGTDFTLTLSALQPVDVGTYYC<br>QQFKTLPYTFGQGTKVDIKA | Light chain of MH67 |
| 88 | ELLMTQSPSSLSASVGDRVTISCRASQ<br>NIYSNLAWYQQKPGKTPKLLIYAASILQSG<br>IPSRFSGSGSGTDYTLTITNLQPEDFGTYYC<br>QQGFGIPYTFGQGTKVEFKA | Light chain of MH73 |
| 89 | QSVLTQPPSVSGAPGQRVTISCT<br>GSNSNIGAGYYVQWYQQLPGTAPKLLIY<br>ENNKRPSGVSDRFSGSKSGTSASLTITGLQSEDEADY<br>YCQSYDSSLSVVLFGGGTRLTV<br>LA | Light chain of MH74 |
| 90 | QSVLTQPQSVSVSPGQTARITCGGDN<br>IGSKNVHWYQQKPPQAPVLVIYAETERPS<br>GIPERFSGSNSGNTATLTISGVEAGDEADYYC<br>QVWDGSSAHVLFAGGTRLTVLA | Light chain of MH75 |
| 91 | QPGLTQPHSVSVSPGQTARITCGGDN<br>IGSKNVHWYQQKPPQAPVLVIYADSERPS<br>GIPERFSGSNSGNTATLTISGVEAGDEADYYC<br>QVWDSSSNHVLFGGGTRLTVL | Light chain of MH76 |
| 92 | DIQMSQSPSSLSASVGDKVTITCQAS<br>QSVSSWLAWYRQKPGKAPKPLIYKASSLE | Light chain |

-continued

| SEQ ID NO. | Sequence | Description |
|---|---|---|
| | GGVPSRFSGSGSGTDFTLTINSLQPEDFATYYC QQYNSVPYSFGHGTKVDIKA | of MH77 |

CDRs are shown in underline.

Table 3Amino acid sequences of antibodies'heavy and light chains

The amino acid sequences of the complementarity determining regions (CDRs) of the heavy and the light chains of the antibodies MH1, MH2, MH36, MH49, MH67, MH73, MH74, MH75, MH76 and MH77 are presented in Table 4 below. The sequences of CDRH1, CDRH2 and CDRH3 are identical in antibodies 49 and 67. These two antibodies have the same heavy chain CDRs with a different light chain, as a result of the combinatorial arrangement of the scFv's. Therefore, the sequences denoted by SEQ ID NO. 102, 103, and 104, are identical to SEQ ID NO. 105, 106, and 107, respectively.

TABLE 4

Amino acid sequences of the antibodies heavy and light chain CDRs

| SEQ ID NO. | Sequence | Description |
|---|---|---|
| 93 | SGGYGWG | MH1 heavy chain CDRH1 |
| 94 | SIYGSTGNTYYNPSLKS | MH1 heavy chain CDRH2 |
| 95 | ARSGTLWFLEF | MH1 heavy chain CDRH3 |
| 96 | SDYYMD | MH2 heavy chain CDRH1 |
| 97 | RISNGGGSKWYADSVKG | MH2 heavy chain CDRH2 |
| 98 | VPTGYSQGV | MH2 heavy chain CDRH3 |
| 99 | SNVWMN | MH36 heavy chain CDRH1 |
| 100 | RIKVKADGGTADYAASVKG | MH36 heavy chain CDRH2 |
| 101 | EEITVARYDY | MH36 heavy chain CDRH3 |
| 102 | RSYWWG | MH49 heavy chain CDRH1 |
| 103 | SIYGSSGSTEYNPSLKS | MH49 heavy chain CDRH2 |
| 104 | QIQFLTDAFDF | MH49 heavy chain CDRH3 |
| 105 | RSYWWG | MH67 heavy chain CDRH1 |
| 106 | SIYGSSGSTEYNPSLKS | MH67 heavy chain CDRH2 |
| 107 | QIQFLTDAFDF | MH67 heavy chain CDRH3 |
| 108 | SSNYWS | MH73 heavy chain CDRH1 |
| 109 | HIFGGGGGTDYNPSLKS | MH73 heavy chain CDRH2 |
| 110 | AAIMYPNRFDV | MH73 heavy chain CDRH3 |
| 111 | TSYWIS | MH74 heavy chain CDRH1 |
| 112 | AIDPTDSDTRYNPSFQG | MH74 heavy chain CDRH2 |
| 113 | SDWSDYYGNSLDV | MH74 heavy chain CDRH3 |
| 114 | SDHYMD | MH75 heavy chain CDRH1 |
| 115 | RISTGGGTTWYADSVKG | MH75 heavy chain CDRH2 |

TABLE 4-continued

Amino acid sequences of the antibodies heavy and light chain CDRs

| SEQ ID NO. | Sequence | Description |
|---|---|---|
| 116 | VPTGYSQGV | MH75 heavy chain CDRH3 |
| 117 | SDYYMD | MH76 heavy chain CDRH1 |
| 118 | RISNGGGTTWYADSVKG | MH76 heavy chain CDRH2 |
| 119 | VPTATSGIGN | MH76 heavy chain CDRH3 |
| 120 | SSSHWWN | MH77 heavy chain CDRH1 |
| 121 | YITTSNGATYYNPSLKS | MH77 heavy chain CDRH2 |
| 122 | GYSNWDNWFDV | MH77 heavy chain CDRH3 |
| 123 | GDNIGSKSVQ | MH1 light chain CDRL1 |
| 124 | ADSERPS | MH1 light chain CDRL2 |
| 125 | QVWDSSSDHVLFGG | MH1 light chain CDRL3 |
| 126 | GDNIGSKNVH | MH2 light chain CDRL1 |
| 127 | AGTERPS | MH2 light chain CDRL2 |
| 128 | QVWDGTREHVLFGG | MH2 light chain CDRL3 |
| 129 | GSSSNIRGNGVH | MH36 light chain CDRL1 |
| 130 | NNNQRPS | MH36 light chain CDRL2 |
| 131 | EAWDNSLSGGLFGG | MH36 light chain CDRL3 |
| 132 | GSSSDIGSHDVY | MH49 light chain CDRL1 |
| 133 | YSNQRPS | MH49 light chain CDRL2 |
| 134 | ETWENSLSGPVFGG | MH49 light chain CDRL3 |
| 135 | ASQAISTYLA | MH67 light chain CDRL1 |
| 136 | YATTLHT | MH67 light chain CDRL2 |
| 137 | QQFKTLPYTFGQ | MH67 light chain CDRL3 |
| 138 | ASQNIYSNLA | MH73 light chain CDRL1 |
| 139 | AASILQS | MH73 light chain CDRL2 |
| 140 | QQGFGIPYTFGQ | MH73 light chain CDRL3 |
| 141 | GSNSNIGAGYYVQ | MH74 light chain CDRL1 |
| 142 | ENNKRPS | MH74 light chain CDRL2 |
| 143 | QSYDSSLSVVLFGG | MH74 light chain CDRL3 |
| 144 | GDNIGSKNVH | MH75 light chain CDRL1 |
| 145 | AETERPS | MH75 light chain CDRL2 |
| 146 | QVWDGSSAHVLFAG | MH75 light chain CDRL3 |
| 147 | GDNIGSKNVH | MH76 light chain CDRL1 |
| 148 | ADSERPS | MH76 light chain CDRL2 |
| 149 | QVWDSSSNHVLFGG | MH76 light chain CDRL3 |
| 150 | ASQSVSSWLA | MH77 light chain CDRL1 |

TABLE 4-continued

| Amino acid sequences of the antibodies heavy and light chain CDRs | | |
|---|---|---|
| SEQ ID NO. | Sequence | Description |
| 151 | KASSLEG | MH77 light chain CDRL2 |
| 152 | QQYNSVPYSFGH | MH77 light chain CDRL3 |

Example 2

Binding of the Chimeric antibodies to Ricin

An Elisa assay, or Biolayer Interferometry (Octate$^{red}$; Fortebio) were used in order to assess the binding ability of the various antibodies prepared as described above to ricin and to each of its two subunits, namely the A chain (RTA) and the B chain (RTB). As demonstrated in FIG. 5A, all of the antibodies showed high affinity to ricin and were able to bind variable epitopes on the antigen.

Figure 5B:
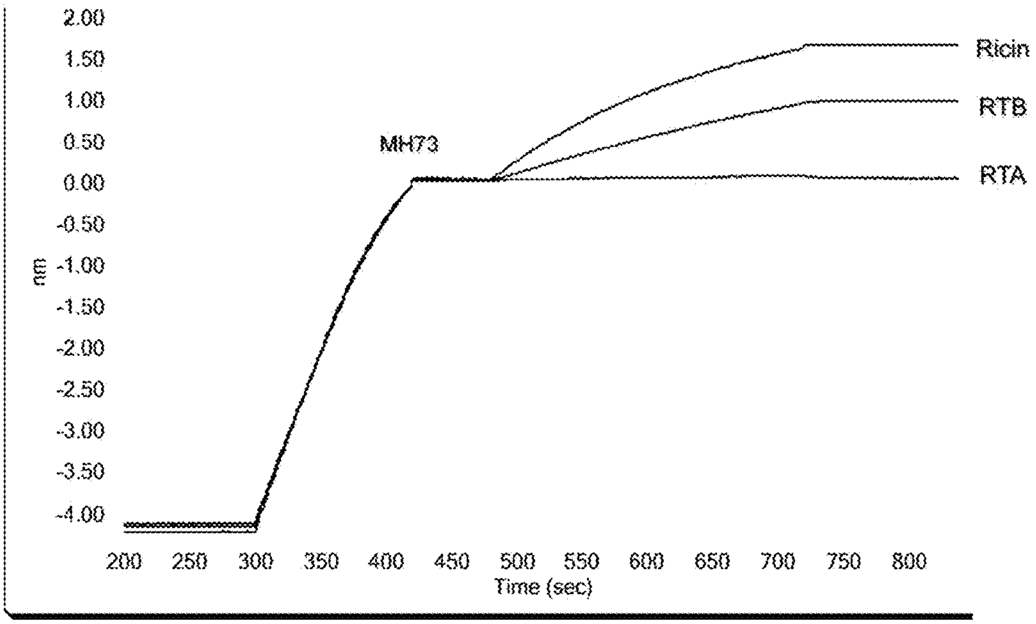

Interestingly, five of the antibodies, namely the antibodies MH1, MH36, MH49, MH67 and MH74 bind the RTA subunit; five antibodies, namely the antibodies MH2, MH73, MH75, MH76 and MH77 bind the RTB subunit. The results concerning MH73 were inconclusive in the ELISA assay but the antibody clearly binds the RTB subunit as measured using Biolayer Interferometry as shown in FIG. 5B.

Example 3

The Chimeric Antibodies Neutralize the Ricin Toxin In Vitro

The capability of each of the antibodies MH1, MH2, MH36, MH49, MH67, MH73, MH74, MH75, MH76 and MH77 to neutralize the ricin toxin was studied using an in vitro neutralization assay in Hela Ub-FL cells, as described above.

The amount of antibody required to neutralize 50% of the toxin is shown in Table 5 below for each of the assayed antibodies (ED=effective dose). As demonstrated in the Table, all of the antibodies were capable of neutralizing the toxin.

TABLE 5

| Concentration of antibody required to neutralize 50% of the toxin | |
|---|---|
| Antibody | $ED_{50}$ (ng/ml) |
| MH1 | 200 |
| MH2 | 5,200 |
| MH36 | 27,000 |
| MH49 | 1,200 |
| MH67 | 52,000 |
| MH73 | 11,000 |
| MH74 | 83,000 |
| MH75 | 150 |
| MH76 | 10,500 |
| MH77 | 500 |

Remarkably, the antibodies MH75, MH1, MH77 and were highly effective in neutralizing the toxin as compared to the other antibodies. Without wishing to be bound by theory, the differences in neutralization efficiency may result from differences in the affinity of each one of the antibodies to the epitope it binds, and also from differences in the epitopes, where some may be more affective for neutralization than others.

Example 4

The capability of each of the anti-ricin antibodies to neutralize the ricin toxin was studied using an in vivo protection assay, as described above.

Several anti ricin antibodies of the invention were tested for their ability to neutralize ricin in vivo. The antibodies MH1 and MH36 were chosen as representatives of the anti-RTA group, MH73, MH75 and MH77 for the anti-RTB group and MH2 and MH76 as representatives of antibodies showing lower affinity.

TABLE 6

| Post exposure treatment efficacy | |
|---|---|
| Antibody | Survival proportions (%) |
| — | 0% |
| MH1 | 100 |
| MH2 | 40 |
| MH36 | 95 |
| MH73 | 83 |
| MH75 | 96 |
| MH76 | 60 |
| MH77 | 100 |

Table 6 shows the survival proportions of mice treated with the different antibodies six hours after intranasal intoxication with $2LD_{50}$ of ricin. Upon intranasal exposure of mice to $2LD_{50}$ of ricin, untreated control animals succumb within 5-9 days (mean time to death of 6.5 days). At six hours post intoxication, mice were treated by intravenous administration of 100µg of the tested antibody and were monitored for 14 days. It was found that treatment with MH1, MH36, MH75 or MH77 yielded extremely high survival rates of 95-100%. Treatment with antibody MH73 resulted with 83% survival while in those groups treated with MH2 or MH76, 40% and 60%, respectively, have survived.

The invention claimed is:

1. An isolated monoclonal antibody or any antigen-binding fragment thereof which binds to ricin toxin, wherein said antibody is selected from a group consisting of:

a. a monoclonal antibody comprising a heavy chain complementarity determining region (CDRH) 1 denoted by SEQ ID NO. 93, CDRH2 denoted by SEQ ID NO. 94, CDRH3 denoted by SEQ ID NO. 95, and the light chain complementarity determining region (CDRL) 1 denoted by SEQ ID NO. 123, a CDRL2 denoted by SEQ ID NO. 124, and a CDRL3 denoted by SEQ ID NO. 125 b. a monoclonal antibody comprising a CDRH1 denoted by SEQ ID NO. 96, CDRH2 denoted by SEQ ID NO. 97, CDRH3 denoted by SEQ ID NO. 98, and a CDRL1 denoted by SEQ ID NO. 126, a CDRL2 denoted by SEQ ID NO. 127, and a CDRL3 denoted by SEQ ID NO. 128;

c. a monoclonal antibody comprising the CDRH1 denoted by SEQ ID NO. 99, CDRH2 denoted by SEQ ID NO. 100, CDRH3 denoted by SEQ ID NO. 101, and a CDRL1 denoted by SEQ ID NO. 129, a CDRL2 denoted by SEQ ID NO. 130, and a CDRL3 denoted by SEQ ID NO. 131;

d. a monoclonal antibody comprising the CDRH1 denoted by SEQ ID NO. 102, CDRH2 denoted by SEQ ID NO. 103, CDRH3 denoted by SEQ ID NO. 104, and a CDRL1 denoted by SEQ ID NO. 132, a CDRL2 denoted by SEQ ID NO. 133, and a CDRL3 denoted by SEQ ID NO. 134;

e. a monoclonal antibody comprising the CDRH1 denoted by SEQ ID NO. 105, CDRH2 denoted by SEQ ID NO. 106, CDRH3 denoted by SEQ ID NO. 107, and a CDRL1 denoted by SEQ ID NO. 135, a CDRL2 denoted by SEQ ID NO. 136, and a CDRL3 denoted by SEQ ID NO. 137;

f. a monoclonal antibody comprising the CDRH1 denoted by SEQ ID NO. 108, CDRH2 denoted by SEQ ID NO. 109, CDRH3 denoted by SEQ ID NO. 110, and a CDRL1 denoted by SEQ ID NO. 138, a CDRL2 denoted by SEQ ID NO. 139, and a CDRL3 denoted by SEQ ID NO. 140;

g. a monoclonal antibody comprising the CDRH1 denoted by SEQ ID NO. 111, CDRH2 denoted by SEQ ID NO. 112, CDRH3 denoted by SEQ ID NO. 113, and a CDRL1 denoted by SEQ ID NO. 141, a CDRL2 denoted by SEQ ID NO. 142, and a CDRL3 denoted by SEQ ID NO. 143;

h. a monoclonal antibody comprising the CDRH1 denoted by SEQ ID NO. 114, CDRH2 denoted by SEQ ID NO. 115, CDRH3 denoted by SEQ ID NO. 116, and a CDRL1 denoted by SEQ ID NO. 144, a CDRL2 denoted by SEQ ID NO. 145, and a CDRL3 denoted by SEQ ID NO. 146;

i. a monoclonal antibody comprising the CDRH1 denoted by SEQ ID NO. 117, CDRH2 denoted by SEQ ID NO. 118, CDRH3 denoted by SEQ ID NO. 119, and a CDRL1 denoted by SEQ ID NO. 147, a CDRL2 denoted by SEQ ID NO. 148, and a CDRL3 denoted by SEQ ID NO. 149; and j. a monoclonal antibody comprising the CDRH1 denoted by SEQ ID NO. 120, CDRH2 denoted by SEQ ID NO. 121, CDRH3 denoted by SEQ ID NO. 122, and a CDRL1 denoted by SEQ ID NO. 150, a CDRL2 denoted by SEQ ID NO. 151, and a CDRL3 denoted by SEQ ID NO. 152.

2. An isolated monoclonal antibody or any antigen-binding fragment thereof which binds to ricin toxin, wherein said antibody comprises a heavy chain variable region and a light chain variable region, wherein said heavy chain variable region is encoded by a nucleic acid sequence which is at least 70% identical to the nucleic acid sequence denoted by SEQ ID NO. 60, SEQ ID NO. 61, SEQ ID NO. 62, SEQ ID NO. 53, SEQ ID NO. 54, SEQ ID NO. 55, SEQ ID NO. 56, SEQ ID NO. 57, SEQ ID NO. 58, or SEQ ID NO. 59 and wherein said light chain variable region is encoded by a nucleic acid sequence which is at least 70% identical to SEQ ID NO. 63, SEQ ID NO. 64, SEQ ID NO. 65, SEQ ID NO. 66, SEQ ID NO. 67, SEQ ID NO. 68, SEQ ID NO. 69, SEQ ID NO. 70, SEQ ID NO. 71, or SEQ ID NO. 72.

3. The isolated monoclonal antibody according to claim 2, wherein said antibody comprises a heavy chain variable region comprising the amino acid sequence denoted by SEQ ID NO. 73, SEQ ID NO. 74, SEQ ID NO. 75, SEQ ID NO. 76, SEQ ID NO. 77, SEQ ID NO. 78, SEQ ID NO. 79, SEQ ID NO. 80, SEQ ID NO. 81, or SEQ ID NO. 82 and a light chain variable region comprising the amino acid sequence denoted by SEQ ID NO. 83, SEQ ID NO. 84, SEQ ID NO. 85, SEQ ID NO. 86, SEQ ID NO. 87, SEQ ID NO. 88, SEQ ID NO. 89, SEQ ID NO. 90, SEQ ID NO. 91, or SEQ ID NO. 92.

4. The isolated monoclonal antibody according to claim 2, wherein said antibody is selected from a group consisting of:

a. a monoclonal antibody comprising a heavy chain variable region comprising the amino acid sequence denoted by SEQ ID NO. 73 and a light chain variable region comprising the amino acid sequence denoted by SEQ ID NO. 83;

b. a monoclonal antibody comprising a heavy chain variable region comprising the amino acid sequence denoted by SEQ ID NO. 74 and a light chain variable region comprising the amino acid sequence denoted by SEQ ID NO. 84;

c. a monoclonal antibody comprising a heavy chain variable region comprising the amino acid sequence denoted by SEQ ID NO. 75 and a light chain variable region comprising the amino acid sequence denoted by SEQ ID NO. 85;

d. a monoclonal antibody comprising a heavy chain variable region comprising the amino acid sequence denoted by SEQ ID NO. 76 and a light chain variable region comprising the amino acid sequence denoted by SEQ ID NO. 86;

e. a monoclonal antibody comprising a heavy chain variable region comprising the amino acid sequence denoted by SEQ ID NO. 77 and a light chain variable region comprising the amino acid sequence denoted by SEQ ID NO. 87;

f. a monoclonal antibody comprising a heavy chain variable region comprising the amino acid sequence denoted by SEQ ID NO. 78 and a light chain variable region comprising the amino acid sequence denoted by SEQ ID NO. 88;

g. a monoclonal antibody comprising a heavy chain variable region comprising the amino acid sequence denoted by SEQ ID NO. 79 and a light chain variable region comprising the amino acid sequence denoted by SEQ ID NO. 89;

h. a monoclonal antibody comprising a heavy chain variable region comprising the amino acid sequence denoted by SEQ ID NO. 80 and a light chain variable region comprising the amino acid sequence denoted by SEQ ID NO. 90;

i. a monoclonal antibody comprising a heavy chain variable region comprising the amino acid sequence denoted by SEQ ID NO. 81 and a light chain variable region comprising the amino acid sequence denoted by SEQ ID NO. 91; and j. a monoclonal antibody comprising a heavy chain variable region comprising the amino acid sequence denoted by SEQ ID NO. 82 and a light chain variable region comprising the amino acid sequence denoted by SEQ ID NO. 92.

5. The isolated monoclonal antibody according to claim 1, wherein said antibody binds to ricin A chain and wherein said antibody comprises a heavy chain variable region comprising the amino acid sequence denoted by SEQ ID NO. 73, SEQ ID NO. 75, SEQ ID NO. 76, SEQ ID NO. 77 or SEQ ID NO. 79 and a light chain variable region denoted by SEQ ID NO. 83, SEQ ID NO. 85, SEQ ID NO. 86, SEQ ID NO. 87 or SEQ ID NO. 89.

6. An isolated monoclonal antibody, wherein said antibody binds to ricin B chain and wherein said antibody comprises a heavy chain variable region comprising the amino acid sequence denoted by SEQ ID NO. 74, SEQ ID NO. 78, SEQ ID NO. 80, SEQ ID NO. 81 or SEQ ID NO. 82 and a light chain variable region denoted by SEQ ID NO. 84, SEQ ID NO. 88, SEQ ID NO. 90, SEQ ID NO. 91 or SEQ ID NO. 92.

7. The isolated monoclonal antibody according to claim 1, wherein said antibody is a highly neutralizing anti ricin antibody selected from the group consisting of a. the monoclonal antibody comprising a heavy chain variable region comprising the amino acid sequence denoted by SEQ ID NO. 73 and a light chain variable region denoted by SEQ ID NO. 83;

b. the monoclonal antibody comprising a heavy chain variable region comprising the amino acid sequence denoted by SEQ ID NO. 75 and a light chain variable region denoted by SEQ ID NO. 85;

c. the monoclonal antibody comprising a heavy chain variable region comprising the amino acid sequence denoted by SEQ ID NO. 80 and a light chain variable region denoted by SEQ ID NO. 90; and d. the monoclonal antibody comprising a heavy chain variable region comprising the amino acid sequence denoted by SEQ ID NO. 82 and a light chain variable region denoted by SEQ ID NO. 92.

8. An immunoconjugate comprising the antibody or any antigen-binding fragment thereof according to claim 1 and an additional anti-ricin agent.

9. A pharmaceutical composition comprising as an active ingredient the isolated monoclonal antibody or any antigen-binding fragment thereof according to claim 1 and a pharmaceutically acceptable carrier, excipient or diluent.

10. The pharmaceutical composition according to claim 9, wherein said composition further comprises an additional anti-ricin agent.

11. A method of prophylaxis, treatment or amelioration of ricin toxin poisoning comprising administering to a subject in need thereof a therapeutically effective amount of the isolated monoclonal antibody or any antigen-binding fragment thereof according to claim 1.

12. The method according to claim 11, wherein said method further comprises administering to a subject in need thereof an additional anti-ricin agent.

13. The method according to claim 11, wherein said isolated monoclonal antibody or any antigen-binding fragment thereof is administered to said subject immediately after exposure to ricin toxin or between about 1 to about 72 hours after exposure to ricin toxin.

14. The method according to claim 11, wherein said antibody is administered at a therapeutically effective amount of 10 μg/kg to about 50 mg/kg.

15. A method of neutralizing ricin poisoning comprising administering to a subject in need thereof a therapeutically effective amount of the isolated monoclonal antibody or any antigen-binding fragment thereof according to claim 1.

16. A method of detecting ricin toxin in a biological sample obtained from a subject, said method comprising:

(a) contacting said biological sample with the isolated monoclonal antibody or any antigen-binding fragment thereof according to claim 1, wherein said monoclonal antibody is labeled with a detectable marker; and (b) detecting said isolated monoclonal antibody or any antigen-binding fragment thereof;

wherein the presence of said isolated monoclonal antibody or any antigen-binding fragment thereof indicates the presence of ricin toxin in said biological sample.

17. A kit for detecting ricin toxin comprising:

(a) at least one labeled isolated monoclonal antibody or any antigen-binding fragment thereof according to claim 1;

(b) instructions for use of said kit.

* * * * *